US012062456B2

(12) United States Patent
Gopalakrishnan et al.

(10) Patent No.: US 12,062,456 B2
(45) Date of Patent: Aug. 13, 2024

(54) HYPOTHETICAL SCENARIO EVALUATION IN INFECTIOUS DISEASE DYNAMICS BASED ON SIMILAR REGIONS

(71) Applicant: Merative US L.P., Ann Arbor, MI (US)

(72) Inventors: Vishrawas Gopalakrishnan, Cambridge, MA (US); Ajay Ashok Deshpande, Pleasantville, NY (US); Sayali Navalekar, Westford, MA (US); James H. Kaufman, San Jose, CA (US); Simone Bianco, San Francisco, CA (US); Kun Hu, Santa Clara, CA (US); Xuan Liu, Yorktown Heights, NY (US); Jacob Ora Miller, Traverse City, MI (US); Raman Srinivasan, Plano, TX (US); Pan Ding, New York, NY (US)

(*) Notice: Subject to any disclaimer, the term of this patent is extended or adjusted under 35 U.S.C. 154(b) by 377 days.

(21) Appl. No.: 17/332,356

(22) Filed: May 27, 2021

(65) Prior Publication Data
US 2022/0384056 A1    Dec. 1, 2022

(51) Int. Cl.
*G16H 50/80*    (2018.01)
*G06F 40/40*    (2020.01)
(Continued)

(52) U.S. Cl.
CPC ............. *G16H 50/80* (2018.01); *G06F 40/40* (2020.01); *G16H 15/00* (2018.01); *G16H 50/20* (2018.01)

(58) Field of Classification Search
CPC ........ G16H 50/20; G16H 40/67; G16H 10/60; G16H 15/00; G16H 50/70; G16H 70/20; G16H 20/17; G16H 10/40; G06F 3/14
See application file for complete search history.

(56) References Cited

U.S. PATENT DOCUMENTS 8,234,129 B2    7/2012 Michon et al.
8,498,879 B2    7/2013 Michon et al.
(Continued)

FOREIGN PATENT DOCUMENTS

CN    106709252 A    5/2017
CN    111445997 A    7/2020
(Continued)

OTHER PUBLICATIONS

N. A. Samat Mathmatical Models for Vector Borne Infectious Disease Mapping With Application to Dengue Disease in Malaysia. Ph.D. Thesis. 2012. (Year: 2012).*
(Continued)

*Primary Examiner* — Jason S Tiedeman
*Assistant Examiner* — Tristan Isaac Evans
(74) *Attorney, Agent, or Firm* — Stephen J. Walder, Jr.

(57) ABSTRACT

Mechanisms are provided to hypothetical scenario evaluations with regard to infectious disease dynamics based on similar regions. A user definition of a hypothetical scenario for a target region is received which specifies scenario features affecting an infectious disease spread amongst a population within the target region. Other predefined regions, in the set of predefined regions, having similar region characteristics to the target region are identified and attributes of the other predefined regions corresponding to the scenario features are identified. Modified model parameter(s) for an infectious disease computer model are derived based on the identified attributes. An instance of the infectious disease computer model is configured with the modified model parameter(s) and the instance is executed on case report data for the target region to generate a prediction for an infectious disease spread in the target region according to the hypothetical scenario, which is then output.

20 Claims, 12 Drawing Sheets

(51) Int. Cl.
  *G16H 15/00* (2018.01)
  *G16H 50/20* (2018.01)

(56) References Cited

U.S. PATENT DOCUMENTS

| | | | |
|---|---|---|---|
| 10,444,235 B2 | 10/2019 | Donovan et al. | |
| 11,504,011 B1* | 11/2022 | Jain | G06N 5/04 |
| 2003/0009239 A1* | 1/2003 | Lombardo | G16H 10/60 700/67 |
| 2007/0229290 A1* | 10/2007 | Kahn | G16H 50/80 702/19 |
| 2008/0208813 A1* | 8/2008 | Friedlander | G16H 50/80 |
| 2010/0138160 A1* | 6/2010 | Jacquez | G16H 50/50 702/19 |
| 2011/0093249 A1 | 4/2011 | Holmes et al. | |
| 2017/0103172 A1 | 4/2017 | Fink et al. | |
| 2017/0300657 A1 | 10/2017 | Barrett et al. | |
| 2017/0316324 A1 | 11/2017 | Barrett et al. | |
| 2018/0366221 A1 | 12/2018 | Crehore et al. | |
| 2019/0131018 A1 | 5/2019 | Sones | |
| 2021/0050116 A1 | 2/2021 | Sabeti et al. | |
| 2022/0013241 A1 | 1/2022 | Meyerson et al. | |
| 2022/0033446 A1 | 2/2022 | Burk et al. | |
| 2022/0199266 A1 | 6/2022 | Achin et al. | |
| 2022/0280621 A1 | 9/2022 | van Buuren et al. | |

FOREIGN PATENT DOCUMENTS

| | | | |
|---|---|---|---|
| CN | 111968751 A | 11/2020 | |
| CN | 112163705 A | 1/2021 | |
| WO | WO-2006116455 A2 * | 11/2006 | B01L 3/5027 |
| WO | WO-2008013553 A2 * | 1/2008 | G06Q 10/1095 |

OTHER PUBLICATIONS

Desai. Real Time Epidemic Forecasting: Challenges and Opportunities. Health Security vol. 17, No. 4, 2019 ª Mary Ann Liebert, Inc. (Year: 2019).*
Dublin, Sacha. NAtural Language Processing to Identify Pneumonia from Radiology Reports. Pharmaceutical Drug Sta. Aug. 2013. (Year: 2013).*
Hogan, Larry. Maryland Targeting Plan for Areas at Risk for Childhood Lead Poisoning. 2015. (Year: 2015).*
Halder. Analysis of the Effectiveness of Interventions Used During the 2009 A/H1N1 Influenza Pandemic. BMC Public Health. 2010. (Year: 2010).*
Samat, Dissertation, Mathematical Models for Vector-Borne Infectious Disease Mapping With Application to Dengue Disease in Malaysia, Centre for Operations Management, Management Science & Statistics, University of Salford, Manchester, UK, 240 pages (Year: 2012).*
List of IBM Patents or Patent Applications Treated as Related, Jul. 29, 2021, 2 pages.
"2019 novel Corona Virus Model", Eclipse Foundation, https://wiki.eclipse.org/2019_novel_Corona_Virus_Model, last modified Sep. 20, 2020, Accessed Feb. 25, 2021, 23 pages.
Anonymous, "A System and a Method for Governing a Big Data-Centric Environment", IP.com Prior Art Database Technical Disclosure, IP.com No. IPCOM000241368D, Apr. 21, 2015, 6 pages.
Anonymous, "Machine Learning Algorithms for Smart Meter Diagnostics", IP.com Prior Art Database Technical Disclosure, IP.com No. IPCOM000242462D, Jul. 16, 2015, 53 pages.
Anonymous, "System and Method for Modeling and Controlling the Spread of Infectious Agents", IP.com Prior Art Database Technical Disclosure, IP.com No. IPCOM000264158D, Nov. 17, 2020, 9 pages.
Baek, Jackie et al., "The Limits to Learning an SIR Process: Granular Forecasting for Covid-19", https://arxiv.org/abs/2006.06373, Submitted on Jun. 11, 2020, 24 pages.
Bird, Alexander, "A simple introduction to epidemiological modelling—the SIR model", King's College London, Peter Sowerby Philosophy & Medicine Project, 2020, 10 pages.
DGHT, "Using Data to Drive Better Programs", U.S. Centers for Disease Control and Prevention (CDC), Division of Global HIV & TB, Dec. 2018, 2 pages.
Gopalakrishnan, Vishrawas et al., U.S. Appl. No. 17/318,027, filed May 12, 2021, titled "Controlling Compartmental Flows in Epidemiological Modeling Based on Mobility Data", 49 pages.
Gopalakrishnan, Vishrawas et al., U.S. Appl. No. 17/332,219, filed May 27, 2021, titled "Hyperlocal Prediction of Epidemic Dynamics and Risks", 126 pages.
Gopalakrishnan, Vishrawas et al., U.S. Appl. No. 17/332,485, filed May 27, 2021, titled "Adapting Computer Modeling of Infectious Disease Based on Noisy Data", 125 pages.
Gopalakrishnan, Vishrawas et al., U.S. Appl. No. 17/332,587, filed May 27, 2021, titled "Automatic Intervention Detection in Infectious Disease Case Reports", 124 pages.
Gopalakrishnan, Vishrawas et al., U.S. Appl. No. 17/332,674, filed May 27, 2021, titled "Automated Monitoring and Retraining of Infectious Disease Computer Models", 126 pages.
Gopalakrishnan, Vishrawas et al., "Globally Local: Hyper-Local Modeling for Accurate Forecast of COVID-19", MedRxiv preprintdoi: https://www.medrxiv.org/content/10.1101/2020.11.16.20232686v1.full, posted Nov. 18, 2020, 31 pages.
Kefayati, Sarah et al., "On Machine Learning-Based Short-Term Adjustment of Epidemiological Projections of COVID-19 in US", medRxiv preprint doi: https://www.medrxiv.org/content/10.1101/2020.09.11.20180521v1, posted Sep. 13, 2020, 8 pages.
Miller, Andrew C. et al., "Mobility trends provide a leading indicator of changes in SARS-CoV-2 transmission", medRxiv, May 11, 2020, 41 pages.
Prem, Kiesha et al., "The effect of control strategies to reduce social mixing on outcomes of the COVID-19 epidemic in Wuhan, China: a modelling study", www.thelancet.com/public-health, v. 5, n. 5, Lancet Public Health, e261-e270, Published Online Mar. 25, 2020, 10 pages.
Rodríguez, Alexander et al., "DeepCOVID: An Operational Deep Learning-driven Framework for Explainable Real-time COVID-19 Forecasting", medRxiv preprint doi: https://www.medrxiv.org/content/10.1101/2020.09.28.20203109v2, Dec. 24, 2020, 8 pages.
Sharov, Konstantin S., "Creating and applying SIR modified compartmental model for calculation of COVID-19 lockdown efficiency", Elsevier, Chaos, Solitons and Fractals, Sep. 24, 2020, 14 pages.
Srivastava, Ajitesh et al., "Fast and Accurate Forecasting of COVID-19 Deaths Using the SIkJα Model", https://arxiv.org/abs/2007.05180, Submitted on Jul. 10, 2020 (v1), last revised Jul. 13, 2020 (this version, v2), 12 pages.
Yang, Hyun M. et al., "Mathematical modeling of the transmission of SARS-CoV-2—Evaluating the impact of isolation in São Paulo State (Brazil) and lockdown in Spain associated with protective measures on the epidemic of covid-19", medRxiv preprint doi: https://www.medrxiv.org/content/10.1101/2020.07.30.20165191v1, Posted Aug. 1, 2020, 54 pages.
Zou, Difan et al., "Epidemic Model Guided Machine Learning for COVID-19 Forecasts in the United States", medRxiv preprint doi: https://www.medrxiv.org/content/10.1101/2020.05.24.20111989v1, posted May 25, 2020, 15 pages.
Zugarini, Andrea et al., "An Optimal Control Approach to Learning in SIDARTHE Epidemic model", arXiv:2010.14878v1 [cs.LG], Oct. 28, 2020, 11 pages.
Chae, Sangwon et al., "Predicting Infectious Disease Using Deep Learning and Big Data", International Journal of Environmental Research and Public Health, 20 pages, Jul. 2018.
Cooper, Ian et al., "A Sir Model Assumption for the Spread of Covid-19 in Different Communities", Chaos Solitons Fractals, doi:10.1016/j.chaos.2020.110057, Oct. 2020, 15 pages.
Haushofer, Johannes et al., "Which Interventions Work Best in a Pandemic?", Science, vol. 368, No. 6495, 9 Pages, May 2020.

(56) References Cited

OTHER PUBLICATIONS

Matzinger, Polly et al., "Strong Impact of Closing Schools, Closing Bars and Wearing Masks During the Covid-19 Pandemic: Results from a Simple and Revealing Analysis", Science AAAS, 15 Pages, Sep. 2020.

Anonymous, "Compartmental Models in Epidemiology", Wikipedia, May 26, 2021, 25 pages.

Anonymous, "Segmented Regression", Wikipedia, May 4, 2021, 6 pages.

Jawa, Taghreed M., "Statistical Methods of Detecting Change Points for the Trend of Count Data", Thesis submitted to the University of Strathclyde, Glasgow, UK, for the degree of Doctor of Philosophy in the Faculty of Science, Jul. 2017, 415 pages.

\* cited by examiner

HYPOTHETICAL SCENARIO EVALUATION IN INFECTIOUS DISEASE DYNAMICS BASED ON SIMILAR REGIONS

BACKGROUND

The present application relates generally to an improved data processing apparatus and method and more specifically to mechanisms for leveraging cognitive computing and artificial intelligence mechanisms to evaluate hypothetical scenarios with regard to infectious disease dynamics based on similar regions.

The present state of the art with regard to making predictions as to the spread of diseases, especially epidemics, is to use a compartmental computing model to represent populations with regard to the infectious diseases. With such compartmental models, a population is assigned to compartments with labels corresponding to different states of the persons with regard to the disease, e.g., susceptible (S), infections (I), or recovered (R). With such modeling, people may progress between compartments with the order of the labels usually showing the flow patterns between the compartments, e.g., a "SEIS" model refers to a flow of persons from a susceptible state (S), exposed state (E), infections state (I), then susceptible (S) again.

The compartmental models are used to predict how a disease spreads, the total number of infected, or the duration of an epidemic, and to estimate various epidemiological parameters, such as the reproductive number. Such models can also show how different public health interventions may affect the outcome of the epidemic, e.g., what the most efficient technique is for issuing a limited number of vaccines in a given population.

The SIR model is one example of a compartmental model, with many other models being derivatives of this SIR model. The model consists of three compartments, the number of Susceptible individuals, the number of Infectious individuals, and the number of Removed (and immune) or recovered individuals. The Susceptible compartment comprises the persons that are susceptible to the infectious disease and if brought into infections contact with an infected infections individual, will contract the disease, at which point the susceptible individual transitions to the Infectious compartment. The Infections compartment comprises the individuals who have been infected and are capable of infecting susceptible individuals. The Removed compartment comprises the individuals that have been removed either because they have become immune (recovered) or have died.

These compartments S, and R represent the number of people in each compartment at a particular time and thus, the number of people in each compartment may change over time even if the total population size remains constant. Each compartment may be modeled as a set of differential equations with functions being defined for the specific disease of interest. Transitions between the compartments have associated transition rates. For example, the transition rate between compartment S and compartment I is a function of the total population, the average number of contacts per person per time, multiplied by the probability of disease transmission in a contact between as susceptible and infections individual. The transmission rate between compartment I and compartment R is proportional to the number of infectious individuals such that the probability of an infectious individual recovering y in any time interval dt is simply ydt, e.g., if an individual is infectious for an average time period D, then y=1/D.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory coupled to the at least one processor and having instructions executed by the at least one processor to specifically configure the at least one processor to execute the method. The method comprises receiving, via a user interface, a user definition of a hypothetical scenario for a target region, in a set of predefined regions. The definition of the hypothetical scenario specifies one or more scenario features affecting an infectious disease spread amongst a population within the target region. The method further comprises identifying one or more other predefined regions, in the set of predefined regions, having second region characteristics similar to first region characteristics of the target region, and identifying one or more attributes of the one or more other predefined regions corresponding to the one or more scenario features. The method also comprises deriving at least one modified model parameter for an infectious disease computer model based on the identified one or more attributes. Moreover, the method comprises configuring an instance of the infectious disease computer model with the at least one modified model parameter, executing the instance of the infectious disease computer model on case report data for the target region to generate at least one prediction for an infectious disease spread in the target region according to the hypothetical scenario, and outputting the at least one prediction in a report output to a user computing device.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
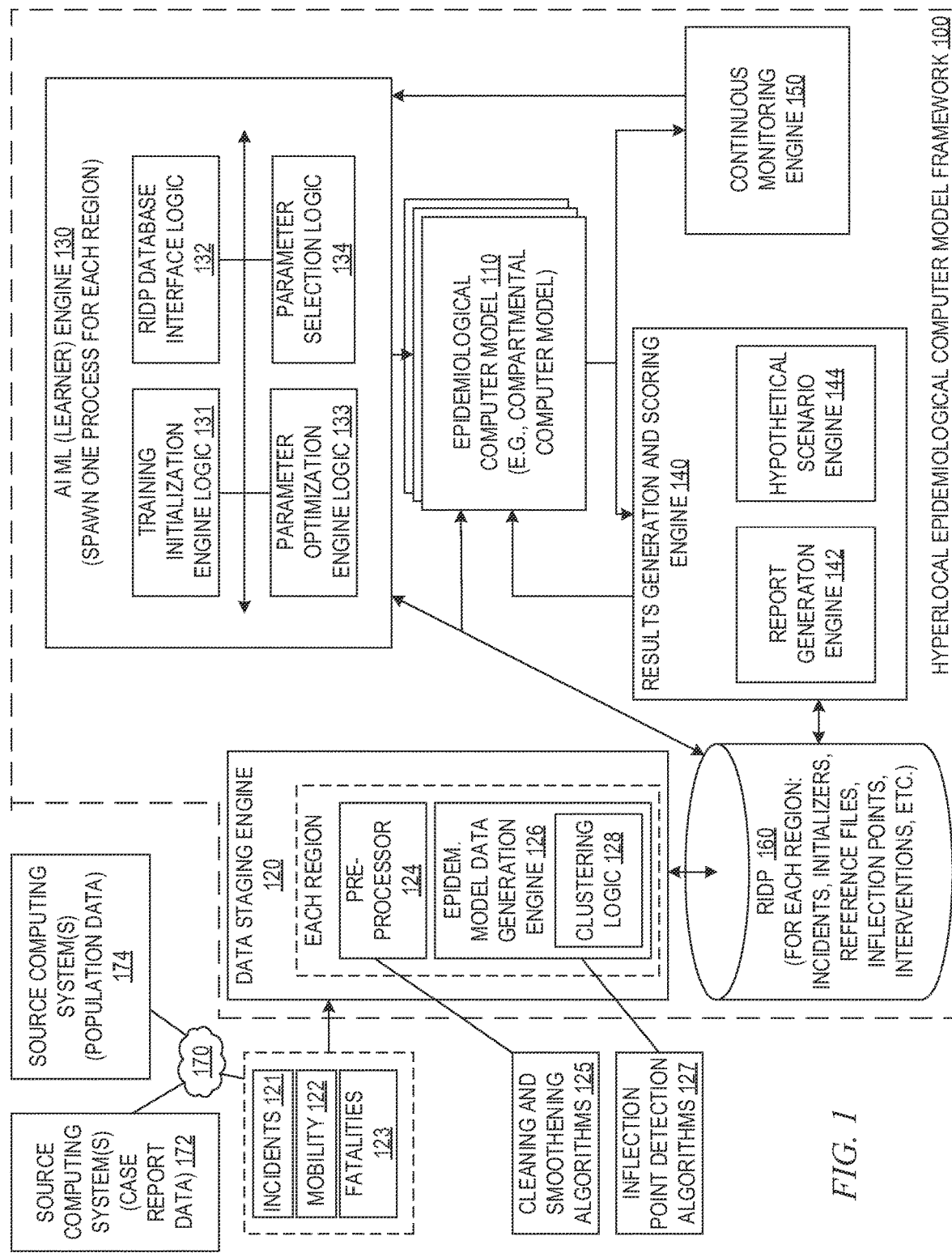
FIG. 1 is an example block diagram of the primary operational elements of a hyperlocal epidemiological computer model framework in accordance with one illustrative embodiment.

Control measures, such as lock-down, restrictions on restaurants and gatherings, social distancing, and the like, for controlling the spread of an infectious disease have shown to be effective. For example, such measures have shown effectiveness in curtailing the spread of the Corona Virus Disease 2019 (COVID-19). However, sustained enforcement of such control measures has negative economic and psychological effects. To craft strategies and policies that reduce the hardship on the population and the economy, while being effective against the spread of the infectious disease, authorities need to understand the disease dynamics at the right level of geospatial granularity commensurate with the decision-making being made, e.g., at the city, county, state, or national levels. Considering factors, such as the hospitals' ability to handle the fluctuating demands, evaluating various reopening scenarios, and accurate forecasting of cases are vital to decision making.

Thus, having the ability to predict the dynamics of infectious diseases, especially in the case of epidemics or pandemics, and characterize risks for populations and risks of changes in governmental and private organization policies with regard to the disease, is of utmost importance from a health safety and economics perspective. That is, being able to predict such dynamics and risks allows decision makers to have accurate information and forecasts upon which to make policy decisions, e.g., whether to enact lockdowns, whether to lift lockdowns, whether to implement mask mandates, or the like, as well as make decisions for preparedness, e.g., activating appropriate healthcare personnel for responding to the dynamics and predictions of the disease spread, ordering equipment that may be needed by healthcare personnel, or the like.

As noted above, the prediction of the dynamics of an infectious disease is primarily accomplished through the use of compartmental computer models, such as SIR and SEIR compartmental computer models, for example. These compartmental computer models capture, with each compartment, the disease dynamics using a set of differential equations and leverage available spatiotemporal disease evolution case data, e.g., positive incidences, deaths, etc., to find unknown hyperparameters and parameters of the underlying computer model. The Eclipse Foundation's Spatiotemporal Epidemiologic Modeler (STEM) is an example of an open-source framework that allows a user to build compartmental models and conduct modeling exercises with data, providing an interactive user interface for modeling. Other model libraries that include SIR and SEIR type compartmental models are also available, such as models from the Massachusetts Institute of Technology (MIT), Institute for Health Metrics and Evaluation (IHME), Imperial College, Columbia University, John Hopkins University (JHU), and the like.

While various compartmental computer models are available, there are a number of limitations on these computer models. For example, known compartmental computer models use incidences and fatality information to model the spread of an infectious disease. These compartmental computer models also focus on long term predictions over large populations, such as on the state or nation level, and do not provide accurate predictions at a lower geospatial or geopolitical regional resolution, such as at the county, town, and district zone level. One reason for this is that modeling at lower granularities during the early stages of an infectious disease spread, such as a pandemic, is prone to data sparsity issues.

In addition, while these compartmental computer models are adept in modeling seasonality of an infectious disease spread, they do not explicitly model localized information that adds contextual knowledge vital to modeling the spread of the disease through the population. What is meant by contextual knowledge is the context of a particular locality relative to other neighboring localities. For instance, existing models do not evaluate or take into consideration that in the early days of the infectious disease spread, e.g., a pandemic, people may be treated in major adjacent regions for want of local hospital capabilities (a contextual knowledge) and thus, the models will incorrectly attribute cases to these adjacent regions.

Another drawback is that existing compartmental computer models fail to recognize and incorporate similarities between infectious disease case data among disparate geospatial or geopolitical regions. That is, certain geospatial or geopolitical regions, which may be geographically remote to one another in terms of geographic distance, may exhibit similarities in spatio-demographic patterns and thus, information from those regions may be pooled together to allow collaborative learning from the patterns of infectious disease behavior exhibited in the various regions, especially in response to interventions implemented in these similar, but different, regions. For example, two different regions may have similar percentages of population in various age groups, ethnic groups, economic groups, numbers of individuals having particular preexisting conditions, such as obesity and respiratory problems, or the like. These similar regions should have similar statistics with regard to the infectious disease, e.g., numbers of incidents and numbers of fatalities, and thus, can be used together to improve predictions generated by epidemiological computer models, such as the compartmental computer models. Moreover, similarities in regions may be used to evaluate hypothetical scenarios using knowledge gained from a similar region where interventions were implemented, so as to determine a likely effect in a target region. However, existing compartmental computer models do not allow for such pooling, collaborative learning, or hypothetical scenario evaluation based on similarities of regions.

As yet another drawback of existing compartmental computer models, these models require a cumbersome process of model parameter tuning. Hyperparameters of the compartmental computer model, i.e., parameters set before machine learning of the model is performed based on various assumptions and which are a basis by which parameters of the computer model are learned, often shift due to various types of interventions, such as government policy (e.g., shelter in place orders), people behavior change (e.g., mask wearing), or therapeutic usage, and these changes or shifting in hyperparameters often tend to be localized. The hyperparameter tuning for compartmental computer models is presently performed using manual effort and thus, the frequent shifting due to such changes requires a considerable expenditure of human and computational resources to modify the existing compartmental computer models manually.

To address these, and other, drawbacks of existing compartmental computer models for modeling the dynamics of an infectious disease, the illustrative embodiments provide mechanisms for hyperlocal prediction of infectious disease dynamics and risks which leverages compartmental computer model technology and artificial intelligence for automatic learning of hyperparameters and parameters of the compartmental computer model. The compartmental computer model framework of the illustrative embodiments uses machine learning training and scoring where the compartmental computer model parameters are learned through the training process from available data and then scored using a prediction approach.

The illustrative embodiments provide mechanisms for implementing an automatic denoising framework to address multiple different types of sources of noise in the infectious disease data. This denoising may be applied both to case report data used for training the epidemiological computer model and to case report data upon which the trained epidemiological computer model operates to generate predictions during runtime operation. Examples of these different types of noise include a first noise type arising from failings in accurate updating of case report data, a second noise type that is due to movement of persons between regions to obtain testing/treatment, e.g., if a major hospital exists in one region, individuals from neighboring regions may go to the major hospital for testing/treatment, and a third noise type that is due to imported cases, e.g., the infectious disease has not spread to the region, but noisy instance data is present due to transient individuals. It should be appreciated that any of these types of noise in the input data may cause an epidemiological computer model to generate incorrect predictions or results and, prior to the automated mechanism of the illustrative embodiments, would require highly trained subject matter experts (SMEs) to manually investigate the sources of the error in the results of the model and make adjustments to the model to compensate for noise. This is unrealistic and impractical especially when one takes into account that such epidemiological computer models are operating on case report and fatality data for thousands of regions, with each set of data potentially having different sources of noise. Moreover, these epidemiological computer models are being executed on a daily basis such that there is not enough time for a human being to be able to adjust the model for noise for each region that is being modeled after manually investigating the sources of error in the model.

The illustrative embodiments provide mechanisms to automatically compensate for such sources of noise based on the type of noise. For example, in order to automatically address the first type of noise, the illustrative embodiments provide mechanisms to automatically smooth input data, such as statistical data from infectious disease case reporting and fatality reports, using filtering procedures which address case reporting irregularities. To address the second type of noise, the illustrative embodiments provide mechanisms for performing clustering of hyperlocal regions into aggregate cluster regions for compartmental computer modeling, which not only addresses the concentration of case reporting in regions from neighboring regions, but also addresses data sparsity issues. To address the third type of noise, the illustrative embodiments provide mechanisms for evaluating the input data with an epidemiological computer model that assumes a community spread of the infectious disease, and a second model that assumes no community spread, or a fixed number of instances of the infectious disease, and determining which hypothesis is most accurate to the real-world data to thereby eliminate modeling assuming community spread when the data points are merely noise due to imported cases.

The clustered and/or smoothed input data may be used to train an epidemiological computer model, such as a compartmental computer model, using an artificial intelligence and machine learning training based hyperparameter and parameter optimization framework. The clustered and/or smoothed input data may also be used as a basis for executing the trained machine learning computer model on new case report and population (e.g., mobility) data. The illustrative embodiments also provide mechanisms for monitoring the resulting trained epidemiological computer model with regard to differences between results generated by the epidemiological computer model and a ground truth, which may be, for example, case reports obtained from source computing systems, such as the Centers for Disease Control (CDC) databases or the like. Thus, for example, the epidemiological computer model may be used to predict incidents and fatalities at time X, and then the case report data gathered by the source computing systems for time X may then be used as the ground truth to determine how well the epidemiological computer model predicted the incidents and fatalities. If there is a statistically significant difference in the prediction from the ground truth, mechanisms are provided to automatically explore alternative sets of model parameters for the epidemiological computer model (also referred to as "hypotheses"), and to automatically select a hypothesis from the set of hypotheses through a pruning process, as described hereafter.

It should be appreciated that the concept of a "statistically significant difference", or a difference that is "statistically significant", will be used throughout this description and is intended to mean that a statistical test of significance, such as a t-test whose corresponding p-value would indicate if the result of the test is significant or not for a threshold, e.g., 95% or 99%, or other known (F-test or variance ratio test, Fisher's Z-test, Chi-Square Test, or the like) or later developed test of significance, is executed and the results evaluated to determine if the difference is statistically significant. The thresholds may be set to any desirable level depending on the desired implementation. The data upon which the statistical significance test is executed will vary depending on what is being tested, however the statistical test will operate similarly.

In addition to the above, the continuous monitoring mechanisms of the illustrative embodiments may operate to compare results of subsequent executions of the epidemiological computer model to previous executions of the epidemiological computer model so as to determine if the results have statistically significant differences, which may indicate a possible change in assumptions and hyperparameter settings. In such a case, the continuous monitoring automatically triggers retraining of the epidemiological computer model to take into account the potential shifting of the assumptions and corresponding hyperparameter values.

For example, the artificial intelligence (AI) based framework of the illustrative embodiments may automatically detect changes in infectious disease transmission dynamics and derive new compartmental computer model hyperparameters based on the detected changes in the disease transmission dynamics. For example, early on in the spread of an infectious disease, it may be assumed that the infectious disease has a transmission rate of TR, such as based on observation of other similar type infectious diseases, e.g., an initial TR may be set for a model of COVID-19 based on previous observations of other Corona Virus transmission rates. While this initial assumption may operate well while the infectious disease has little spread, as additional data is gathered and processed by the epidemiological computer model, the predictions generated may be less and less accurate compared to a ground truth of the actual data that is reported, such as by the CDC or other authoritative source, and the predictions may be less like previous predictions for the disease, where the predictions are predictions of numbers of new incidents (individuals found to have the infectious disease) per unit of time, cumulative numbers of incidents over a predetermined window of time, number of fatalities per unit of time, and/or cumulative number of fatalities. When the differences become statistically significant, model parameters need to be adjusted to address inaccuracies in the previous assumptions and corresponding hyperparameters and/or operational parameters of the epidemiological computer model. It is expected that as the epidemiological computer model is adjusted over time and the amount of available data regarding the infectious disease spread increases, the number of times that such differences are determined to be statistically significant will fall.

With regard to adjustment of hyperparameters, the AI based framework, in some illustrative embodiments, may set the hyperparameters to new values by identifying an uncertainty in predictions generated by the trained compartmental computer model and readjusts the compartmental computer model based on the uncertainty of the prediction and an optimization process applied to the derived new hyperparameters based on observations made from analysis of data and epidemiological computer model results for similar regions, where the similar regions may be similar in terms of infectious disease dynamics and/or population characteristics even though the regions may be geographically distant from one another. In this way, the framework of the illustrative embodiments is able to determine and adjust for shifting of hyperparameter assumptions over time by looking at the relative differences between executions of the trained compartmental computer model. Moreover, grid search or other mechanism for generating alternative sets of hyperparameter values, or "initializers", may be used generate instances of the epidemiological computer model, evaluate the results of these instances to determine the best performing, e.g., least error, alternative, and select the best performing alternative as a new set of initializers for the epidemiological computer model, i.e. configure the epidemiological computer model with the new set of hyperparameter values.

As noted above, the mechanisms of the illustrative embodiments configure the AI based framework and compartmental computer model to operate on hyperlocal geospatial or geopolitical regions with regard to the infectious disease dynamics data received from source case reporting computing systems, and provides mechanisms for denoising this data at the hyperlocal level as well as clustering hyperlocal regions into aggregate cluster regions. In some illustrative embodiments, these geospatial regions may be associated with political boundaries and thus, may be considered geopolitical regions. The geopolitical region(s) may be defined in terms of a corresponding geographical area defined by the political boundary, within which governmental or private organizations have authority to make decisions and policies that apply to the population of that geographical area, especially with regard to interventions for addressing spread of an infectious disease, such as an epidemic or pandemic. The geospatial/geopolitical regions may have varying sizes and configurations and may be at different levels of granularity, e.g., city, county, state, country, political union, or the like. While the illustrative embodiments will be described in terms of a geopolitical region, the illustrative embodiments are not limited to such and may be implemented with regard to any grouping of a population of individuals that have the potential to be affected by, and spread, an infectious disease. The example of geopolitical regions is used in the description of the illustrative embodiments because the illustrative embodiments are especially well suited to assist community leaders, political leaders, healthcare authorities, and the like, in decision making for the geopolitical regions in which they have authority. However, it should be appreciated that the illustrative embodiments may be applied to any desired region comprising a designated population that has affiliations with a geospatial area. The regions and/or clusters or groupings of regions may be referenced herein as "geo-units" for simplicity.

Due to the mechanisms of the illustrative embodiments and their operations with regard to hyperlocal geopolitical region-based evaluations of infectious disease dynamics, the resulting compartmental computer model of the illustrative embodiments is able to generate community level risk predictions based on current and predicted data. For example, the illustrative embodiments may provide measures of risk using an established scale, such as a 1 to 6 risk level scale, where 1 indicates a safe state while 6 indicates an epidemic within the community that is not controlled.

These evaluations of risk on a hyperlocal level allow community leaders, political leaders, healthcare authorities, or the like, to make more informed decisions regarding the populations over which they have authority based on local needs. This is especially useful when one takes into consideration the differences in characteristics of geopolitical regions with regard to infectious disease dynamics and the demographics and mobility of the corresponding population, e.g., stricter measures may be needed in areas of dense population, e.g., New York city, as opposed to more sparsely populated areas, e.g., Purcell, Oklahoma or populations having demographics indicating a higher number of individuals in older age brackets and/or having more incidents of co-morbidities, e.g., obesity, respiratory issues, and the like.

The mechanisms of the illustrative embodiments provide a number of advantages over known compartmental computing models. These advantages include hyperlocal level accurate predictions of infectious disease state, dynamics, and predicted risk. In addition, the illustrative embodiments provide mechanism for automatic intervention detection to detect changes in disease dynamics, such as due to government policies, changes in human behavior, and changes in therapeutic usage. The illustrative embodiments provide mechanism for automatically learning and tuning parameters and hyperparameters of the compartmental computer model, performing error monitoring of the trained compartmental computer model, and automatic triggering of retraining of the compartmental computer model using the mechanisms of the illustrative embodiments. In addition, the illustrative embodiments provide mechanism for uncertainty prediction and community risk prediction using the hyperlocal region capabilities of the illustrative embodiments.

Before beginning the discussion of the various aspects of the improved computing tool of the illustrative embodiments, and the improved computer operations performed by the improved computing tool of the illustrative embodiments, in greater detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software executing on computer hardware, specialized computer hardware and/or firmware, or any combination thereof that performs the specified functions including, but not limited to, any use of a general and/or specialized processor in combination with appropriate software loaded or stored in a machine readable memory and executed by the processor to thereby specifically configure the processor to perform the specific functions of the illustrative embodiments. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Epidemiological Computer Model Framework Architecture and Flow

The illustrative embodiments provide an improved epidemiological computer model artificial intelligence (AI) framework and framework operation. It should be appreciated that the illustrative embodiments are specifically directed to an improved computer tool. The present invention may be a specifically configured computing system, configured with hardware and/or software that is itself specifically configured to implement the particular mechanisms and functionality described herein, a method implemented by the specifically configured computing system, and/or a computer program product comprising software logic that is loaded into a computing system to specifically configure the computing system to implement the mechanisms and functionality described herein. Whether recited as a system, method, of computer program product, it should be appreciated that the illustrative embodiments described herein are specifically directed to an improved computing tool and the methodology implemented by this improved computing tool. In particular, the improved computing tool of the illustrative embodiments specifically provides an improved AI framework for epidemiological computer modeling that provides mechanisms for automatically and dynamically modify the configuration of the epidemiological computer model to maintain or improve the predictions generated by the epidemiological computer model based on the real-world data. The improved computing tool implements mechanism and functionality, such as an epidemiological computer model, a data staging engine, a learner engine, a report generation and scoring engine, and a continuous monitoring engine, which cannot be practically performed by human beings either outside of, or with the assistance of, a technical environment, such as a mental process or the like.

Functions of the illustrative embodiments as described herein are intended to be performed using automated processes without human intervention. While a human being, e.g., a user such as a community leader, healthcare authority, political leader, or the like, may make use of results generated by the improved computing tool of the illustrative embodiments, the illustrative embodiments of the present invention are not directed to actions performed by the user, but rather logic and functions performed specifically by the improved computing tool. Even though the present invention may provide an output that ultimately assists human beings in evaluating and predicting the spread of infectious diseases and provides assistance for evaluating various interventions that may be implemented and predictions of their efficacy in reducing the spread of the infectious disease, the illustrative embodiments of the present invention are not directed to actions performed by the human being viewing the results of the processing performed by the improved computing tool of the illustrative embodiments, but rather to the specific operations performed by the specific improved computing tool. Thus, the illustrative embodiments are not organizing any human activity, but are in fact directed to the automated logic and functionality of an improved computing tool.

The illustrative embodiments described herein implement, and make use of, artificial intelligence (AI) and/or cognitive systems. The purpose of these AI and/or cognitive systems is to augment, not replace, human intelligence. These AI and/or cognitive systems are designed to enhance and extend human capabilities and potential through specific improved computer tools and improved computer tool operations. These improved computer tools perform operations at a speed, complexity, and volume that is not practically able to be performed by human intelligence. While such AI and/or cognitive systems may emulate achieving similar results to that of human intelligence, they do so using different methodologies and mechanisms specific to computer tools that are not the same as any mental processes or manual efforts of human beings due, at least in part, to the inherent differences in the way that computing devices operate from the way that human minds operate.

The AI and/or cognitive systems implemented by the illustrative embodiments may operate on various types of data, which may include personal or private information of individuals. While the AI and/or cognitive systems may operate on such personal or private information, the AI and/or cognitive computing systems implement various mechanisms (not specifically shown in the figures) for maintaining the privacy and security of individual's personal or private information and implement a principle of trust and transparency with regard to the security of such personal or private information. This principle of trust and transparency recognizes that any person whose data is tracked and shared should always be given the option to opt-in or opt-out of such tracking and sharing of their personal or private data. This principle of trust and transparency recognizes that a person whose data is tracked and shared should always have control over the use of the data, what entities have access to that data, and the ability to have that data deleted. Moreover, this principle of trust and transparency recognizes that a person's personal or private data should be kept secure from cyber threats and that such data should not be used for purposes, such as government tracking and surveillance, which are not specifically approved by the individual who again, is the ultimate owner of this personal and/or private data.

Thus, where the AI and/or cognitive systems operate on any such personal or private information, these AI and/or cognitive system mechanisms implement functionality for individuals to opt-in or opt-out of usage of their personal/private data, authorize entities to access their personal/private data, and provide security mechanisms to ensure that the individual's personal/private data is secure from cyber threats. These mechanisms do not require individuals to relinquish ownership rights in their personal/private data or insights derived from the personal/private data in order to have benefit of the illustrative embodiments. While the illustrative embodiments may promote and utilize free movement of data across one or more data networks which may span organizational and geopolitical borders, such free movement of data is done so using mechanisms that promote security of the personal/private data flows.

The improved epidemiological computer model AI framework, hereafter simply referred to as the "framework", of the illustrative embodiments provides an end-to-end epidemiological computer model framework that is built on a plug-and-play architecture. The plug-and-play architecture allows for the core epidemiological computer model and the data pre-processing engines to be easily substituted. The framework is data source agnostic and can easily scale across different types of core models and different data sources. The framework provides mechanism to perform hypothetical "what-if" scenario and/or counter-factual experimentation in a high-level descriptive fashion rather than requiring users to know detailed parameter settings of the epidemiological computer model being used. The framework further provides mechanisms for monitoring of multiple hypotheses and determining which is the closest to the real-world data so that the epidemiological computer model hyperparameters (those that are not tuned by machine learning) and/or operational parameters (those tuned by machine learning) may be adjusted/maintained to represent as close as possible the real-world data. The framework provides mechanism that include, detect, and adapt to external intervention response to the infectious disease being modeled, such that realistic predictions of infectious disease dynamics are provided for various types of interventions.

FIG. 1 is an example block diagram of the primary operational elements of a hyperlocal epidemiological computer model AI framework (or simply "framework") in accordance with one illustrative embodiment. As shown in FIG. 1, the framework 100 comprises an epidemiological computer model 110 that is configured to model dynamic characteristics of an infectious disease, such as the Corona Virus Disease 2019 (COVID-19), influenza, or the like. In the depicted example, the epidemiological computer model 110 is assumed to be a compartmental computer model and thus, may be referred to herein interchangeably as an epidemiological computer model or a compartmental computer model. While a compartmental computer model is used as an example of the epidemiological computer model 110 in the present description of the illustrative embodiments, it should be appreciated that the illustrative embodiments may be implemented with any suitable infectious disease or epidemiological computer model that is currently known or later developed. The framework 100 is a plug-and-play type framework and thus, different types of epidemiological computer models may be used in an easily changeable manner with models being plugged-into the framework 100, their configuration information provided to the framework 100, and the interfaces between the framework 100 and the computer models 110 being configured based on this configuration information so as to facilitate data communication between the framework 100 and the computer models 110. Moreover, while the depicted example shows a single instance of the epidemiological computer model 110, there may be multiple instances of the epidemiological computer model 110 to facilitate parallel processing with regard to different sets of initial hyperparameters (initializers), such as with regard to a grid search or the like, and/or evaluation of different potential interventions or other hypothetical "what-if" scenario predictions, as described hereafter.

The epidemiological computer model 110, in one illustrative embodiment, is a compartmental computer model that is specifically modified to take into consideration the mobility and isolation characteristics of a population of interest by providing mechanisms for collecting and processing mobility information from mobility devices, e.g., mobile smartphones or the like, associated with a portion of the population, and countermeasure, or intervention, information, e.g., governmental mask mandates, bar/restaurant shutdowns, shelter in place orders, etc., from source computing systems, such as governmental computing systems, health organizations, such as the Centers for Disease Control (CDC), or the like. An example of an augmented compartmental computer model 110 that may be implemented as part of the hyperlocal infectious disease model framework 100 is described in co-pending, and commonly assigned, U.S. patent application Ser. No. 17/318,027, filed May 12, 2021, which is hereby incorporated herein by reference, and described in greater detail hereafter. The mobility data may be obtained from a mobility data tracking and collection service and the databases and computing systems associated with that mobility data tracking and collection service. The countermeasure or intervention information may be obtained from various source computing systems associated with governmental, healthcare, or other organizations that maintain information about countermeasures or interventions implemented by various authorities to try to control the spread of an infectious disease. It should be appreciated that the interventions may be countermeasures, i.e., actions taken to curtail the spread of the disease, or may be lifting of countermeasures or restrictions on a population, such as lifting mobility restrictions, lifting closures or occupancy restrictions on businesses, lifting of mask mandates, or the like.

It should be appreciated that while the illustrative embodiments will be described in terms of the augmented compartmental computer model being implemented as the epidemiological computer model 110 of the hyperlocal infectious disease model framework 100, the illustrative embodiments are not limited to such. To the contrary, other known or later developed compartmental computer models, such as SIR or SEIR based compartmental computer models, may be used without departing from the spirit and scope of the present invention. Moreover, other types of epidemiological computer models 110, other than compartmental computer models, which may implement machine learning based training of model parameters, may be used without departing from the spirit and scope of the present invention. For example, various convolutional neural networks (CNNs), deep learning neural networks (DNNs), Random Forest models, Support Vector Machine (SVM) models, or the like, may be used to provide the epidemiological computer model 110 without departing from the spirit and scope of the present invention.

Again, as shown in FIG. 1, the framework 100 further comprises a data staging engine 120, an artificial intelligence (AI) machine learning (ML) engine 130 (or simply "learner engine" 130), a results generation and scoring engine 140, and a continuous monitoring engine 150, in addition to the epidemiological computer model 110. These elements 110-150 operate in conjunction with a regional infectious disease and population (RIDP) database 160 which receives infectious disease state information, e.g., case reports specifying incident (new infections being detected) data and fatality data, and population data, such as mobility data, demographic data, etc., and provides this data to the various elements 110-150. In addition, the data in the RIDP database 160 may be updated with best initializer range parameters and/or parameter settings, i.e., initial hyperparameter and parameter settings for the epidemiological computer model 110, for the particular infectious disease state, and inflection point tuning data, as described hereafter. The RIDP database 160 organizes data according to predefined geospatial or geopolitical regions (or simply "regions"), and/or clusters of such regions, where the individual regions and/or clusters of regions may be generally referred to as "geo-units".

In accordance with one or more of the illustrative embodiments, these regions are defined on a level smaller than country or national levels of geographic size and thus, facilitate a local evaluation of infectious disease dynamics. The regions may be predetermined according to geographic and/or political borders, e.g., counties, cities, states, territories, or the like. By organizing the data according to predetermined local region, hyperlocal infectious disease modeling is made possible that facilitates identifying similarities between relatively smaller populations, evaluation of infectious diseases based on clustering of similar regions to leverage, in the machine learning, similarities in infectious disease dynamics from potentially geographically distant regions, and evaluation of the impact of interventions, e.g., countermeasure options, lifting of restrictions, or the like, on local regions based on similar interventions being employed in other similar local regions.

To understand the "hyperlocal" nature of the modeling performed by the mechanisms of the illustrative embodiments, it should be considered that the backbone of epidemiological computer modeling is the assumption of uniform population mixing, however such assumptions do not take into account the differences in population and population intermixing in different regions. For example, consider a sparsely populated state in the United States of America, such as North Dakota, which contains pockets of towns and rural areas. If the state of North Dakota reports 500 cases, it is not an accurate picture for the epidemiological computer model because it is not taking into account the fact that these 500 cases are spread out over a vast sparsely populated land mass and that the population actually has a much lower interaction rate than other more densely populated states. For example, New York is not as sparsely populated and in fact has centers of very high intermixing population, such as New York City, such that 500 cases reported by the state of New York conveys a different magnitude because of the population interaction percentage. The point is that the geo-spatial granularity needs to be the right level (geo-level) so as to properly account for infectious disease transmission for the particular region(s) being modeled. After modeling at the correct geo-level, one can further drill down by approaches like population based division.

Hyper-local modeling, in accordance with the illustrative embodiments, is modeling the infectious disease at the lowest possible granularity, or geo-level. In some illustrative embodiments, this hyper-local modeling is performed at a county level, but can also be performed at other higher or lower granularities, such as a particular zip-code area or the like. Because of issues with data availability, as well as the sparsity of data issue, especially during the early stages of infectious disease spread, such as in the case of a pandemic, modeling at the lowest geo-level gives high error due to various sources of noise. However, with the clustering approach of the illustrative embodiments, the mechanisms of the illustrative embodiments are able to automatically find the correct level of granularity for hyper-local modeling that does not dilute infectious disease characteristics and at the same time provides sufficient information to accurately model the infectious disease dynamics. That is, a lowest or default geo-level may initially be assumed, but then clustering may automatically adjust this geo-level up to include other neighboring regions in order to obtain a level of data needed to accurate model the infectious disease spread during early spread, and then may operate on lower levels of granularity that do not require such clustering, such as during later stages of the infectious disease spread.

That data staging engine 120 receives infectious disease data from one or more infectious disease source computing systems 172 via one or more data networks 170. These infectious disease source computing systems 172 may comprise various data sources including publicly available infectious disease databases, government computing systems and health organization computing systems, e.g., state government computing systems, natural government computing systems, government and/or private health organization computing systems, such as computing systems associated with the CDC, National Institutes of Health (NIH), World Health Organization (WHO), hospital associations, health insurance companies, and/or the like. The data staging engine 120 may also receive population data from population data source computing systems 174, such as mobility data indicating the mobility of the population based on location and/or movement information, such as may be obtained from monitoring mobile computing devices associated with individuals of the population.

Such mobility data may be obtained from global positioning system (GPS) services, various cellular or other wireless location services, or the like. For example, various location services collect and maintain databases regarding locations of individuals' portable computing devices, e.g., smartphones, health tracker and activity tracker devices, and the like, and these databases may be mined for population mobility information. It should be appreciated that this mobility data is infectious disease agnostic and the collection of such mobility data from the portable computing devices may not be initially tied to the infectious disease modeling but may be collected and maintained for different purposes other than infectious disease modeling. That is, the mobility data may be based on existing location services collecting the mobility data for other uses other than the infectious disease modeling of the illustrative embodiments, e.g., fitness tracking, "find my friends" information, navigation purposes, etc., or in some illustrative embodiments, may be mobility data that is specifically collected for infectious disease modeling, such as via infectious disease tracing applications on mobile devices and corresponding Internet or cloud services that provide functionality for tracing interactions between individuals of a population to monitor the potential spread of a disease.

It is assumed, for purposes of the illustration in FIG. 1, that the data processing system(s) upon which the elements 110-160 are implemented, have other interfaces, hardware, and software logic to facilitate accessing such infectious disease source computing systems 172 and population data source computing systems 174 via wired and/or wireless data communication links, communication sessions, and the like. Such interfaces, hardware, and software logic may employ various communication protocols and security mechanism as are generally known in the art. In short, the data processing system(s) are configured to be able to communicate data, request data messages, responsive data messages, and the like, to and from these source computing systems 172 and 174 via the one or more data networks 170.

It should be appreciated that the data staging engine 120 accesses data and processes data from the various source computing systems 172 and 174 on a regional basis. Similarly, the learner engine 130 and results generation and scoring engine 140 may also operate on data for each separate predefined region. What is meant by the data being accesses and processed on a regional basis is that case reports, fatality data, and population data such as mobility data and demographic data, are gathered and correlated with particular regions based on location information in the data to thereby associate the data with particular predefined regions, e.g., counties. For example, particular case reporting source computing systems may be associated with particular regions, e.g., a county hospital is associated with that county, and thus, data reported from that source computing system will be associated with that predefined region, e.g., Cooke County Hospital's data is associated with Cooke County. Location data may be stored in association with reported data and used to correlate that data with a region in other source computing systems that collect the data from various regional sources, e.g., the CDC maintains databases of case reports and fatalities reported from other sources and when those other sources report the data, it is associated with location information and a predefined region. Thus, the mechanisms of the illustrative embodiments may operate on this data on a regional basis so as to provide a hyperlocal prediction of infectious disease dynamics. It should be appreciated that since the illustrative embodiments may operate on data on a regional basis, while a single instance of the elements of the framework 100 is shown, the framework 100 may in fact implement multiple instances of these elements to facilitate predictions for various regions, clusters of regions, or to implement various other functions such as grid searches, hypothetical scenario evaluations, and the like.

As mentioned previously, the region may be defined as any geographical, geospatial, or geopolitical portion of a geographical area, such as a county, territory, state, or the like. The region is preferably defined as being a sub-portion of a larger geographical area, such that a geographical area is composed of a plurality of regions. Each region has an associated population which as the potential of being exposed to the infectious disease being modeled. Thus, if the infectious disease spreads to the population, the reported cases (incidents and fatalities) are reported in association with that region. It should be appreciated that the population is modeled in the epidemiological computer model with regard to the spread of the infectious disease through this population, but the population itself may be greater than the members of any compartment in the epidemiological computer model, as not all of the population are susceptible to the infectious disease, may not become infected, or the like. The population of a region may coincide with where the individuals have their domicile, work, or the like, but this is not required, as the illustrative embodiments operate on case reports and what region from which the case reports originate or which the case reports indicate is the corresponding region for the case report, e.g., a patient location specified in the case report.

In one illustrative embodiment, the data staging engine 120 receives case report information comprising incident information 121 and fatality information 122 from the various infectious disease source computing systems 172. For example, this information may comprise numbers of incidents, e.g., infections per predetermined period of time (e.g., daily, weekly, etc.), cumulative infections over a predetermined period of time (e.g., daily, weekly, etc.), as well as numbers of deaths per predetermined period of time, as specified in the case reports of the various source computing systems 172. Incident information, in one illustrative embodiment, refers to results of testing indicating that an individual has contracted the infectious disease. However, incident information may include other occurrences related to the infectious disease, such as hospitalizations, or the like. Fatality information refers to deaths of individuals that are attributed, at least in part, to the individual contracting the infectious disease.

The data staging engine 120 may further receive population data, which in the depicted example is population mobility data 123, for a predetermined period of time, although the population data may include other demographic information that may be helpful in modeling the spread of the infectious disease using the compartmental computer model 110, identifying similar regions in terms of population demographics, or the like, e.g., age statistics for the population, gender statistics, ethnicity statistics, income level statistics, or the like. The mobility data 123 may comprise statistical measures of how much of the population of the corresponding region is considered mobile and how much of the population is essentially isolated, whether due to their own self-isolation measures, or through governmental or other organization interventions, i.e., implementing of countermeasure mandates such as mask mandates, shelter-in-place orders, shut-downs of bars/restaurants or restricting occupancy limits of such establishments, for example. The obtaining and processing of mobility data 123 is described in the above incorporated commonly assigned and co-pending U.S. patent application Ser. No. 17/318,027, and described hereafter in connection with the more detailed description of the augmented compartmental computing model illustrative embodiment.

The received input data regarding the infectious disease and population state 121-123 is processed via a pre-processor 124 and epidemiological computer model data generation engine 126 of the data staging engine 120. The data stating engine 120 operates on the raw data 121-123 from the source computing systems 172, 174 to remove noise in the data, identify inflection points in the trends of the data, correlate these inflection points with intervention data, cluster regions to address noise and sparsity of data issues, as well as determine initializers (hyperparameter values) for the epidemiological computer model based on the correlations and clustering. This information is then stored in the RIDP database 160 on a regional basis for use by other elements of the framework 100.

The pre-processor 124 of the data staging engine 120 applies data cleaning and data smoothening algorithms 125 to the input data 121-123 in order to address a first source of noise in the raw input data 121-123. To address a second source of noise, the epidemiological computer model data generation engine 126 may implement clustering logic 128. With regard to a third source of noise in the data, logic in the learner engine 130 is provided, as will be described hereafter.

With regard to the first source of noise, the input data 121-123 has a number of potential sources of discontinuity and erroneous data, which may result due to inconsistencies in the reporting of data causing positive/negative spikes in the data, and other discontinuities, that need to be rectified before being able to generate a set of data usable by the compartmental computer model 110. The data cleaning and data smoothening algorithms 125 operate to create an approximating function that captures important patterns in the input data 121-123 while eliminating noise. Data cleaning is a process of fixing or removing incorrect, duplicate, or incomplete data within a dataset. Smoothening is a statistical technique that reduces data points higher than their neighboring data points and increases data points lower than their neighboring data points in accordance with a smoothening function or algorithm. Data cleaning and smoothening algorithms are generally known in the art and thus, a more detailed description of these operations are not presented herein. An example of data smoothening will be shown in conjunction with the description of inflection point identification hereafter.

There are a variety of different reasons why the input data 121-123 may comprise incorrect, duplicate, incomplete, and noisy data which requires cleaning and smoothening. For example, it is often the case that more reporting is done during different time periods than others, e.g., there are more reports of incidents during weekdays, when more doctor offices, clinics, pharmacies, and the like, are open and patients have appointments, than there are on weekends. Moreover, data is reported differently from different sources, e.g., hospitals may report incidents and deaths on the weekends and holidays while doctor's offices, emergency clinics, pharmacies, and the like, may not. Furthermore, a patient may be diagnosed as having the disease at a hospital in one region, but the patient lives in another region and thus, the incident is reported as being present in the first region when it should be reported in the region where the patient lives and has a higher likelihood of spreading the infection. In addition, a patient may be tested for an infectious disease in multiple locations within the same or different regions and, as a result, the number of incidents reported may be inflated due to duplicate data. These inconsistencies in reporting may cause the data to seem spikey and disjointed, i.e., noisy and incomplete.

Data cleaning and smoothening algorithms 125 are applied by the pre-processor 124 to the input data 121-123 to remove the spurious data and make the data more consistent by identifying the trends in the data, thereby lessening the effects of the variability of the case reporting from the source computing systems 172. In some illustrative embodiments, the data cleaning and smoothening algorithms 125 include one or more of an adaptive degree polynomial filter (ADPR), a Savitzky-Golay filter, or the like, to smoothen the data.

In addition, the pre-processor 124 also may apply algorithms to handle negative data, such as source data corrections. Such negative data refers to corrections in data reported based on subsequent modifications of the data. For example, a source may report 500 cases of an infectious disease on day 1, but then on day 2 indicates that this previous number was incorrect and that the actual number was 300 cases. However, data sources avoid making retrospective changes to correct reporting errors and thus, the data may not be monotonically increasing. Models that operate on cumulative totals of incidents do not permit the cumulative totals to decrease and hence, negative corrections are not easily integrated into these types of models. The negative data algorithms comprise logic to identify such corrections in source data and adjusts the data through the pre-processing to make the data consistent. In some illustrative embodiments, these negative data algorithms comprise applying an isotonic regression that finds a weighted least-squares fit to a vector with a weights vector subject to a set of non-contradictory constraints, which ensures that cumulative numbers of incidents are monotonically increasing.

Thus, through data cleaning and smoothening as well as negative data corrections, the pre-processor 125 addresses sources of noise due to irregularities in reporting. The second source of noise addressed by the illustrative embodiments arises from the mobile nature of the population and the sparsity of case report and fatality data. That is, often individuals of a population travel between regions, e.g., for work, to visit friends/family, to obtain treatments, engage in commerce, or the like. As a result, incidents may be reported in one region, but the individuals live/work or otherwise may expose individuals in a different region. Moreover, many geographical areas may have sparse data due to the rural nature of the geographical area. Furthermore, in some areas, centers of healthcare may be located in a different region from where individuals live and thus, they may travel from their home region to the region where there is a center of healthcare where they can receive testing and treatment for the infectious disease. These various situations may cause noise in the data in terms of spikes in one region's incidents/fatalities which are in essence a cumulative total from neighboring regions due to the mobile nature of the individuals in the neighboring regions.

The illustrative embodiments provide clustering logic 128 for clustering neighboring regions into a cluster or group of regions, as a single geo-unit, for epidemiological computer modeling. This clustering addresses the noise by spreading the incidents/fatalities across a large population comprising a larger number of regions, thereby reducing the spikiness of the data and providing a trend in the data.

The third source of noise, which is actually addressed via the learner engine 130, occurs as a result of transient individuals in the population. For example, a target region may not have experienced a community spread of the infectious disease but may have incidents reported due to individuals from other regions temporarily traveling to the target region, e.g., vacationers, individuals "just passing through", or the like. These incidents will get reported in the target region but will not represent a community spread. Thus, it is important to detect such cases by evaluating not only hypotheses assuming a community spread (e.g., assuming an exponential growth in the spread of the infectious disease), but also the null hypothesis that assumes no community spread (e.g., a flat curve with no growth of the spread of the infectious disease). These mechanisms will be described in greater detail hereafter.

The data cleaning and smoothening, as well as clustering, performed by the pre-processor 124 and the epidemiological computer model data generation engine 126 also allows the epidemiological computer model data generation engine 126 to perform identification of inflection points in the data that are more representative of actual changes in the dynamics of the infectious disease spread, which may correspond to instituted policies, lifting of restrictions, distribution of a vaccine, implementation of other types of interventions, or other outside influences that change the number of incidents and/or fatalities. Such changes are more abrupt than other influences on the spread of an infectious disease, such as seasonal weather, natural immunity, and the like. Such changes indicate points at which parameters of the compartment computer model 110 may need to be modified in order for the model 110 to provide useful and accurate results. That is, after data cleaning and smoothening algorithms 125 are applied by the preprocessor 124 to the raw input data 121-123 to generate smoothened input data, and clustering is performed by the clustering logic 128, the epidemiological computer model data generation engine 126 applies one or more inflection point detection algorithms 127 to the cleaned/smoothened/clustered input data to determine points at which trends in the data change appreciably.

In particular, the inflection point detection algorithms 127 operate on the pre-processed input data to identify "knee" and "elbow" points in the smoothened input data. A "knee" in the data is a point along a curve representing the input data where the curve initially has a positive or upward direction trend and has an abrupt change in the opposite direction, i.e., changes to a negative or downward direction trend. That is, a "knee" is an abrupt transition from a positive trend to a negative trend in the curve of the smoothened input data. An "elbow" is an abrupt transition from a negative trend to a positive trend in the curve of the smoothened input data.

The knee and elbow points represent discontinuities in the input data which are indicative of external influences on case reporting. These discontinuities may specify changes in numbers of incidents, changes in cumulative numbers of incidents within a window of time, changes in fatalities, changes in cumulative fatalities within a window of time, changes in population mobility, etc. that appear to have been caused by some other outside influence other than the infectious disease itself, such as the introducing of an intervention, the lifting of restrictions, or the like. For example, an abrupt reduction in incidents and/or mobility of the population may coincide with government mandates being imposed that restrict movement of the population, e.g., shelter in place orders, requiring the wearing of masks, or the like. Moreover, a change in incidents may be due to imposing/lifting of closure requirements for bars/restaurants, restrictions/lifting of restrictions on occupancy of business establishments, or other gatherings of individuals. Thus, by identifying inflection points in the cleaned/smoothened data, and correlating those inflection points with data specifying interventions and/or other outside influences, such as may be obtained from other knowledge databases, publicly available computing systems, or the like, the correlations may indicate which of the operational hyperparameters of the epidemiological computer model 110 may need to be modified and corresponding dynamic updating of the hyperparameters of the epidemiological computer model 110 may be performed in an automated manner.

For example, the epidemiological computer model 110 may utilize a transmission rate parameter $\beta$, and this value may be set for different sections of the input data based on the identified inflection points, e.g., the transmission rate parameter may be higher during times when mobility data indicates that the mobility of the population is less restricted, e.g., an inflection point at which time a lifting of occupancy limits in restaurants from 25% to 50% of maximum occupancy was performed, and may be lower during times when the mobility data indicates that the mobility of the population is more restricted. This may coincide with government mandates, self-isolation of the population, or any other interventions or outside influences, e.g., seasonal climate changes, or the like. Moreover, there may be time periods determined from historical data and/or heuristic analysis, which indicate when, and for how long, certain interventions have efficacy with regard to the spread of the infectious disease, e.g., lag times between interventions and indications of efficacy of the interventions, lag times between when a "patient zero" enters a region and when additional incidents are reported, lag times between when an intervention occurs and a change in incidents results in the data, etc. These time periods may be correlated with the particular inflection points and interventions so as to identify when hyperparameters of the epidemiological computer model 110 need to be modified to reflect real-world conditions and generate accurate predictions.

Initial configuration of the epidemiological computer model data generation engine 126 may specify the number of inflection points to maintain for epidemiological modeling as well as heuristic rules for filtering out and/or maintaining inflection points. For example, even though there may be 10 inflection points identified of a period of time, the configuration information may specify that only 5 inflection points are to be maintained. The number of inflection points to maintain may be based on a desired implementation since each inflection point may represent a re-execution of the epidemiological computer model 110 to perform predictions of disease state information, e.g., numbers of new cases (incidents), fatalities, or the like, based on changes in hyperparameters of the epidemiological computer model 110. Moreover, restricting the number of inflection points may help in avoiding spurious inflection points that are not the result of interventions. The particular number of inflection points, as well as criteria for selecting which inflection points to maintain, may be specified in configuration information.

The identified inflection points that are maintained may also be adjusted according to epidemiologically curated heuristic rules specifying lag times for interventions, e.g., a lag time from when cases are first reported to when interventions have actual efficacy, and other periods of observed temporal conditions on the interventions, for example, changes in transmission rate may be sustained for three weeks, interventions do not occur in the early stages of the infectious disease spread, or the like, so as to make the assumptions and hyperparameter values more epidemiologically reasonable to what is actually observed. For example, heuristic rules may be defined in the configuration of the inflection point detection algorithms 127 that specify that inflection points that are within 21 days of the assume start date of the infectious disease are not maintained and that each inflection point is considered to be effective for at least 30 days.

The setting of the various initial values for the hyperparameters of the compartmental computer model 110 for the various portions of the input data may be reflected in a set of "initializers" or initializer ranges. These initializers or initializer ranges are hyperparameter and/or operational parameter value ranges for specifying hyperparameter/operational parameter values to use to configure the epidemiological computer model 110. Hyperparameters are parameters that are not learned by the epidemiological computer model 110 through the machine learning training of the epidemiological computer model 110, while operational parameters are parameters whose values are trained and learned through the machine learning training of the epidemiological computer model 110. These initializers may be initially specified by a subject matter expert (SME) based on their own experience and expertise and according to a set of assumptions. However, the illustrative embodiments provide automated mechanisms for updating the hyperparameter values within these ranges as needed and to automatically determine when these initializers or initializer ranges need to be modified because the assumptions and resulting initializer boundaries, i.e., the minimum and/or maximum values in the ranges, are no longer accurate to the real-world data. For example, characteristics regarding the initial infected population, susceptible population, and disease characteristics may be assumed and specified in terms of the initializer ranges. Thereafter, the sets of initializer ranges may be automatically modified based on historical analysis of previously observed trends in case reports/fatalities and corresponding initializer ranges found to generate accurate compartmental computer model predictions, as will be described in greater detail hereafter.

As noted above, the epidemiological computer model data generation engine 126, in some illustrative embodiments, comprises clustering logic 128. This clustering logic 128 may operate to cluster region case report data, inflection point data, population data, and/or intervention data to thereby identify similar regions and make determinations as to whether or not the epidemiological computer model 110 should be executed for a given region or for the cluster/group of regions. That is, the epidemiological computer model data generation engine 126, in accordance with some illustrative embodiments, comprises logic 128, such as in the form of one or more statistical analysis computer models or the like, that determine whether the pre-processed input data from pre-processor 124 for a region indicates sufficient mobility of the population of a region to warrant execution of the epidemiological computer model 110 on the regions' data to generate predictive outputs for the region or that clustering of the region with neighboring regions is to be performed.

In some illustrative embodiments, this analysis is based on sources of population data, such as the U.S. Census Bureau's databases indicating home/work locations and commuting information of the population, to generate an adjacency matrix where each node is a region or geo-unit, such as a county, and edges represent the strength of a commute between the regions or geo-units, e.g., counties. The adjacency matrix is symmetrized to reflect the commute to and from the home/work locations. The adjacency matrix is then used as a basis to cluster/group counties (regions) based on this commute information. In this way, clustering of regional data may be performed on sparsely populated regions or regions with sparsely occurring cases, based on workplace to residence, and vice versa, transit data, mobility data, based on statistical area evaluations such as measurement statistical analysis (MSA) or core-based statistical area (CBSA), or the like.

It should be appreciated that clustering of regions may also be applied based on similarity of characteristics of the disparate regions, which may be geographically local or remote to each other. For example, the clustering logic 128 may apply clustering algorithms to identify similar regions in terms of demographics of the population, characteristics of the infectious disease spread, interventions implemented/lifted, and the like. This data may be used to generate numerical representation of the characteristics of a region which may then be evaluated using clustering logic and distance evaluation algorithms to identify similar characteristic regions and cluster/group them for later use, such as when evaluating hypothetical scenarios or the like, as discussed hereafter. Thus, in addition to addressing noisy data using the data cleaning and smoothing of the input data via the pre-processor 124, and clustering/grouping of regions based on mobility of the population between regions, the clustering logic 128 of the epidemiological computer model data generation engine 126 may also be used to evaluate geo-spatial, population, and infectious disease characteristics to cluster/group the regions together.

Thus, the epidemiological computer model data generation engine 126 of the data staging engine 120 obtains the cleaned/smoothened input data from the preprocessor 124 comprising, for example, the daily incidents and fatality information, and daily population data changes, e.g., daily mobility/isolation change data, and generates inflection point data representing the discontinuities in the input data. These inflection points may be correlated with intervention data, e.g., data specifying governmental policies, countermeasures, and other environmental and influential factors outside the infectious disease itself, that have correspondence to the timeframe of the inflection points. In addition, the epidemiological computer model data generation engine 126 also receives/generates combinations of initializers for the epidemiological computer model parameters. Hence, the epidemiological computer model data generation engine 126 provides the cleaned/smoothened input data comprising incident information, fatality information, mobility information, and the like, as well as the determined inflection points and corresponding initializer combinations to the RIDP database 160. This may be performed with regard to each predefined region such that the RIDP database 160 stores such information according to corresponding predefined region. Moreover, the epidemiological computer model data generation engine 126 may further cluster regions based on the data and determine if and when epidemiological computer model 110 execution is appropriate.

It should be appreciated that while the data staging engine 120 operations, e.g., with regard to the pre-processor 124 and epidemiological model generation engine 126, are described in terms of staging data for storage in the RIDP 160 which is then used to train the epidemiological computer model 110 using a regional machine learning training operation, the operation of these elements may also be used during runtime operation after training the epidemiological computer model 110, such as when new case report data is received. That is, data cleaning and smoothening may still be performed, inflection point detection may still be performed, etc., during runtime operation and such smoothened data and inflection point data may be used executed the epidemiological computer model 110 to generate predictions of infectious disease state or dynamics, e.g., incidents and fatalities, for the target region.

As shown in FIG. 1, the hyperlocal epidemiological computer model framework 100 further comprises an artificial intelligence (AI) machine learning (ML) engine 130 (or simply "learner engine" 130) that serves to train and/or retrain the epidemiological computer model 110, e.g., the compartmental computer model 110 in the depicted example. The learner engine 130 comprises training initialization engine logic 131 for determining whether or not to perform training of the model 110. The training initialization engine logic 131 first is set to perform training of the epidemiological computer model 110 and once training has been determined to be completed, e.g., a convergence of the epidemiological computer model 110 is achieved through a machine learning process, then the training initialization engine logic 131 may be set to not perform continued training of the epidemiological computer model 110. However, the training initialization engine logic 131 may be reset to retrain the epidemiological computer model 110 if later logic in the results generation and scorer engine 140 determines that hyperparameter shifting has occurred, that assumptions used to set initializer ranges are no longer accurate, training of additional instances of the epidemiological computer model 110 is to be performed, such as for evaluating alternative sets of initializers or hyperparameter values, or the like. There may be multiple instances of the logic of the learner engine 130 for different associated epidemiological computer model 110 instances.

Assuming that training of the epidemiological computer model 110 is to be performed, the learner engine 130 comprises RIDP database interface logic 132 that retrieves initializer ranges, and regional input data, population data, inflection point data, and the like, from the RIDP database 160 for a corresponding region or cluster of regions, hereafter referred to as the target region/cluster. The learner engine 130 further includes parameter optimization engine logic 133 that interfaces with the epidemiological computer model 110 to perform model parameter optimization, with regard to hyperparameters, such as by performing a grid search or other epidemiological computer model parameter optimization, to select a setting for the hyperparameters for the epidemiological computer model 110 for the target region, where the hyperparameter values, e.g., transmission rate hyperparameter $\beta$, are selected from within the range of possible values specified by the initializers, i.e., the initializer ranges, where there may be a different range for a plurality of different hyperparameters. The parameter optimization engine logic 133 may instantiate different instances of the epidemiological computer model 110 for parallel execution, configuring each instance with a different setting of hyperparameter values, bounded by the ranges of the initializers, for performing the grid search or other optimization selection of hyperparameter values. Each instance is executed on the region's data to generated results and the performance of the instances of the epidemiological computer model 110 are evaluated, such as with regard to precision, recall, or other performance metrics, both with regard to the original setting of hyperparameter values and each of the alternative hyperparameter value settings.

The predictions, e.g., numbers of incidents and number of fatalities, generated by the various instances of the epidemiological computer model 110 may be compared to a ground truth to determine performance measures for these various instances. For example, historical data, numbers of incidents, number of fatalities, etc., may be maintained for the region in the RIDP database 160 and may be used to perform training and/or retraining of the epidemiological computer model 110 by executing the epidemiological computer model 110 on the historical data a predetermined time period in the past, e.g., four weeks in the past, and generating predictions for the current disease state. Thus, the predictions may then be compared to the current disease state, which is used as the ground truth, to determine an error, such as the normalized root mean square error (RMSE) of daily incident, cumulative incident, and cumulative deaths with respect to the corresponding ground truth. The determined error may then drive modifications to the operating parameters, i.e., the machine learning based learnable parameters, of the epidemiological computer model, to thereby reduce this error. This process may be repeated through a plurality of epochs of machine learning training of the epidemiological computer model 110 until convergence is reached, i.e., the error has been reduced to equal or below a predetermined threshold, or a predetermined number of epochs have occurred. Such a process may be performed with regard to each instance and the best performing hyperparameter values, i.e., the values providing the lowest error, are used to update the RIDP database 160 via best initializer and parameter selection logic 134. The best performing instance of the epidemiological computer model 110 may then be retained for performing predictions.

As shown in FIG. 1, the training initialization engine logic 121 may determine that further training may be required if continuous monitoring engine 150 determines that assumptions/hyperparameter range shifting has occurred or if the continuous monitoring engine 150 determines that the predictions have significantly (determined by a test for significance) deviated from the real-world data (which is used as a ground truth). That is, the initializers, or range of hyperparameter values, are set based on assumptions regarding population state, infectious disease state, and certain dynamics of the infectious disease, e.g., hyperparameters specifying transmission rates, initial population of infected individuals, initial population of recovered or removed individuals, initial population of susceptible individuals, etc. However, these assumptions may change over time, or may be shown to have been inaccurate, due to various effects. For example, the initial assumptions are based on a relatively small amount of data about the infectious disease and as more data is obtained, it may be determined that the additional demonstrates that the initial assumptions were incorrect. Moreover, as another example, the introduction of interventions, where "interventions" are any purposeful manipulations of the infectious disease state or characteristics of the population, e.g., mobility, to change the dynamics of the infectious disease, e.g., government mandates, self-isolation measures, distribution of a vaccine, or the like, may cause previously accurate assumptions to no longer be accurate. Thus, as these effects on the assumptions become present in the real-world data, it is important to re-evaluate the assumptions, and corresponding initializer ranges, to determine if they still hold or if updates to the assumptions and the initializer ranges and hyperparameter values for the epidemiological computer model 110 need to be implemented.

The continuous monitoring engine 150 of the illustrative embodiments evaluates the predictions generated by the epidemiological computer model 110 to determine if hyperparameter shifting has likely occurred, at which point the continuous monitoring engine 150 updates the logic 121 of the learner engine 130 to cause the logic 121 to initiate retraining of the epidemiological computer model 110 on the current data for the region as stored in the RIDP database 160. The continuous monitoring engine 150 also evaluates these predictions to determine if statistically significant deviations from the real-world observed data has occurred, such that retraining of the epidemiological computer model 110 is warranted.

During runtime operation, assuming the epidemiological computer model 110 has been trained and thus, additional training by the learner engine 130 is not needed at that time, the epidemiological computer model 110 may be invoked to generate predictions as to infectious disease state, population state, and the like. For example, in some illustrative embodiments, the epidemiological computer model 110 operates to generate predictions as to numbers of individuals classified into different compartments, e.g., susceptible (S), infected (I), recovered/removed (R), deceased (D), worsening (W), or the like, of the epidemiological computer model 110 and thus, can report numbers of infected individuals and numbers of fatalities. These predictions may be made on input data based on hyperparameter values and machine learning learned operational parameter values, which may be tailored to particular intervention conditions, e.g., given that there is a lock-down and mobility is restricted, a particular set of parameter values, such as including an isolation rate parameters and/or transmission rate parameters, may be used to configure the instance of the epidemiological computer model 110 to generate predictions for the region knowing that it is in a lock-down state. Such predictions may also be used to assist decision makers with performing decisions such as what interventions to implement to modify, and hopefully reduce, the spread of an infectious disease through a population corresponding to a region of interest, or cluster of regions of interest. That is, hypothetical scenarios may be explored to evaluate the predicted effects of interventions/lifting of restrictions so that decision makers can make more informed decisions.

The results generation and scorer engine 130 comprises report generation logic 142 to obtain predictions regarding infectious disease dynamics from the model 110 and generate reports specifying the predictions for use in decision support operations. The report generation logic 142 may provide a user interface through which the reports generated by the report generation logic 142 may be presented to a user for viewing and assisting with decision making. Various textual, graphical, and/or audible outputs may be provided via the user interface to present the results of the report generation, e.g., graphical representations of the various predictions with regard to portions of the population of infected, susceptible, deceased, or the like, at various future time points based on predictions from current and historical data for the region. The reports generated provide information regarding the current state of the infectious disease, such as the number of individuals classified into the various compartments of a compartmental computer model being used to model the infectious disease, at specified time points, such as future time points, as well as the predictions of the dynamics of the infectious disease, e.g., changes in infection rate and fatality rate, and population risks based on a modeling of the infectious disease spread within the corresponding region or cluster of regions.

In viewing the reports generated based on the predictions generated by the epidemiological computer model 110, a user may wish to evaluate potential changes in interventions, or lifting of restrictions, that may help achieve a desired infectious disease and/or population state. For example, a user may wish to determine what the predicted disease state and population state may be if particular interventions are implemented and/or lifted, e.g., implementing a shelter-in-place order, lifting a restriction on bar/restaurant capacity, increasing a roll-out of a vaccine, or the like. The results generation and scorer engine 140 may provide a hypothetical scenario engine 134 that provides user interfaces and logic to take high level descriptions of scenarios that the user wishes to explore, i.e., hypothetical scenarios, and translate those high-level descriptions to modifications in hyperparameters and/or operational parameters of the epidemiological computer model 110. An instance of the epidemiological computer model 110 with the modified hyperparameters may be generated and executed on the data from the RIDP database 160 for the region of interest in order to generate a prediction of disease/population state under the assumptions and conditions of the hypothetical scenario.

The hypothetical scenario engine 134 may comprise logic that performs similarity analysis between the infectious disease data, population data, inflection point data, and knowledge bases specifying interventions implemented in the various regions. This similarity analysis may be achieved through clustering logic, similar to clustering logic 128 described above, where the clustering of regions may be performed based on similarities of infectious disease data and population data to identify regions having similar disease states and population states. In some illustrative embodiments, if such clustering has already been performed with regard to clustering logic 128, the clusters generated may be retrieved by the hypothetical scenario engine 134 from the RIDP database 160 and used to perform hypothetical scenario prediction and analysis.

With regard to the clustering of similar regions, for example, regions having similar numbers of infected individuals, and similar demographic statistics of the population, may be assumed to have similarities in responses to interventions. For those similar regions, evaluation of the inflection points and corresponding interventions implemented in the similar regions may be used as a basis for determining modifications to hyperparameters and operational parameters of the epidemiological computer model 100 in response to hypothetical scenarios involving such interventions. For example, a user may want to know what the affect would be on the spread of an infectious disease if the bar/restaurant capacity were increased from 25% to 50%. The hypothetical scenario engine 134 may find, through clustering of regions, a similar region where a lifting of bar/restaurant capacity was performed and the data for that similar region indicated an inflection point at a particular time point after implementing the lifting of the intervention, e.g., 2 weeks later the infection rate increased by X %. This increase in infection rate in the similar region may be used to modify the hyperparameters or operational parameters of a hypothetical, or "what-if", scenario instance of the epidemiological computer model 110 to be similar to the similar region and then model the current region based on this "what-if" scenario instance. As a result, the "what-if" scenario instance will generate predictions of disease state and population state based on potential modifications of interventions or other changes. Thus, observations of patterns in data for similar regions may be leveraged to make predictions in a current region should similar interventions, or lifting of interventions, or other changes be employed.

Thus, with the hyperlocal epidemiological computer model framework 100 of the illustrative embodiments, improvements to the way in which data is conditioned and staged for training and/or runtime processing by an epidemiological computer model 110 are provided. These improvements include providing computer executed logic that specifically configures the data processing system(s) implementing the data staging engine 120 to obtain case report data and population data, e.g., mobility data, preprocess the received input data to perform data cleaning and smoothening, clustering, and identification of inflection points in the cleaned and smoothened, and possibly clustered, data. The improvements further provide computer executed logic that specifically configures the data processing system(s) to correlate these inflection points with information obtained from knowledge bases, such as from source computing systems 172 and/or 174, which specify changes in policies affecting the population of the given region, interventions instituted or lifted in the region, etc. Based on these correlations, changes in hyperparameters and/or operational parameters of the epidemiological computer model 110 may be automatically instituted for the current and/or future time frames, where the future time frames may be set based on knowledge regarding lag times with regard to infectious disease spread and/or efficacy of interventions or the like. These improvements may be applied to various types of input data, e.g., daily case report data, cumulative case report data, daily/cumulative death data, daily mobility data, etc. These improvements may also be applied for various hyperparameters and/or operational parameters of the epidemiological computer model 110.

In addition to the preprocessing mechanisms and inflection point detection and correlation, the data staging engine 120 further provides logic for clustering similar regions and determining whether regions, or clusters of regions, have sufficient changes in incidents, fatalities, or mobility data to warrant performing infectious disease dynamics modeling via the epidemiological computer model 110. The illustrative embodiments may then automatically initiate execution of the epidemiological computer model 110 in response to determining that sufficient changes in incident data, fatality data, or mobility data is present to warrant the generation of new infectious disease dynamics predictions.

The illustrative embodiments further provide improvements in the manner by which the training and re-training of the epidemiological computer model are performed. The illustrative embodiments provide computer executed logic that specifically configures the data processing system(s) providing the AI-ML learner engine 130 to determine whether to execute machine learning training of the epidemiological computer model 110 and select a set of epidemiological computer model hyperparameters and/or operational parameters using a grid search or other optimization process based on a set of initializers, such as by performing parallel execution of instances of the epidemiological computer model 110 using different hyperparameter/parameter values and evaluating the different instances to determine which provides a best performance, such that the set the hyperparameter/parameter values for that instance are selected for use in performing infectious disease dynamics predictions, e.g., daily incidents and/or death predictions for predetermined periods of time in the future. The best or optimal set of hyperparameter/parameter values may be stored for future use. The grid search or other optimization may be based on a set of initializers, which may specify ranges of potential values for hyperparameter/parameter values.

The illustrative embodiments also continuously monitor the performance of the epidemiological computer model 110 to determine if it is generating predictions that are significantly different from previous recent predictions generated by the epidemiological computer model 110. If there is a significant difference, this difference may be due to a shifting of the hyperparameters based on changes in conditions that would cause the underlying assumptions used to select the hyperparameter values to be no longer accurate, e.g., introduction of new interventions, vaccines, changes in mobility, etc., and thus, may require a retraining of the epidemiological computer model. The illustrative embodiments automatically detect when such hyperparameter shifting occurs and automatically initiates a retraining of the epidemiological computer model 110 using current up to date data in the RIDP database 160.

Moreover, the illustrative embodiments provide mechanisms that generate reports of infectious disease dynamics based on the predictions generated by the epidemiological computer model 100, where such reports provide mechanisms for posing high level descriptions of hypothetical scenarios for investigation. The illustrative embodiments provide mechanisms for converting the high-level descriptions to modifications in hyperparameter and/or operational parameter values for generating an instance of the epidemiological computer model 110 that is configured with the modified hyperparameter and/or operational parameter values. The instance of the epidemiological computer 110 may then be executed to generate predictions based on this hypothetical, or "what-if", scenario to provide results to a user specifying what would happen if the hypothetical scenario were to occur.

The converting of the high-level descriptions to modifications in hyperparameter and/or operational parameter values may be based on a clustering of similar regions and analysis of other similar region data to determine similar "what-if" conditions that previously were present in these other similar regions, e.g., introduction of similar interventions in these similar regions. The historical data for these similar regions may be analyzed to identify the resulting values of the hyperparameters and/or operational parameters that most closely matched the real-world conditions seen as a result of these "what-if" conditions, e.g., similar region B instituted a shelter-in-place order which resulted in a reduction of the infection rate by 25% approximately 2 weeks after the order was in place and thus, in order to model a similar shelter-in-place order for region A, the infection rate hyperparameter should be reduced by 25%.

The evaluation of the hypothetical, or "what-if", scenario using the modified instance of the epidemiological computer model 110 may further include executing an instance of the epidemiological computer model 110 where the "what-if" conditions are not implemented, i.e., a "null hypothesis" instance of the epidemiological computer model, for comparison purposes. That is, by modeling the infectious disease dynamics and generating predictions for both the hypothetical scenario, and an absence of the hypothetical scenario, an evaluation of how the "what-if" conditions will affect the infectious disease dynamics is made possible.

The improvements provided by the mechanisms of the illustrative embodiments will be described in greater detail in the following sections.

Data Staging Engine

Figure 2:
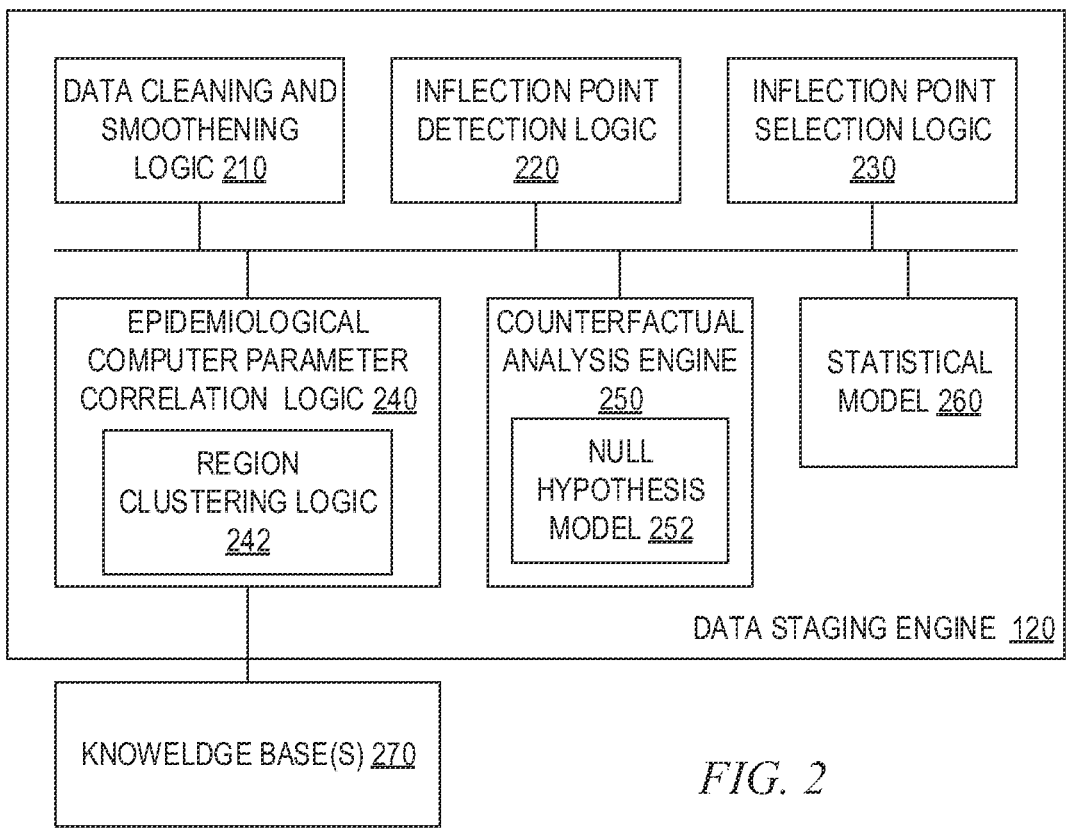
FIG. 2 is an example block diagram of the data staging engine in greater detail showing the primary operational logic elements of the data staging engine in accordance with one illustrative embodiment.

As described above, the data staging engine 120 operates to obtain case report data for an infectious disease, such as incident data and fatality data, and may further obtain population data, which may include mobility data, from various source computing systems 172 and 174. FIG. 2 is an example block diagram of the data staging engine 120 in greater detail showing the primary operational logic elements of the data staging engine 120 in accordance with one illustrative embodiment. As shown in FIG. 2, the data staging engine 120 comprises a pre-processor 124 with data cleaning and smoothening logic 210. The data cleaning and smoothening logic 210 may comprise various algorithms and filters for cleaning data, as previously described above, and for applying smoothening filters, such as the adaptive-degree polynomial filter, Savitzky-Golay filter, and/or moving average smoothing filters, for example, to the input data, such as case reports of incidents, fatalities, and population characteristic data, such as mobility data or the like. The smoothening may be applied to the input data 121-123 prior to inflection point detection and may also be applied to the parameter transitions after inflection point detection so as to provide a smooth transition from one set of epidemiological computer model parameters to another corresponding to sub-sections of infectious disease progression in response to interventions.

In some illustrative embodiments, the data cleaning and smoothening logic 210 may apply algorithms to clean the data to correct for negative data, as previously mentioned above. For example, in some illustrative embodiments, an isotonic regression defined by the following may be applied to the data:

$$\min \Sigma_{i=1}^{n} w_i(x_i - a_i)^2 \text{ subject to } x_i \leq x_j \text{ for all } (i,j) \in E$$

The application of the isotonic regression involves finding a weighted lease-squares fit $x \in \mathbb{R}^n$ to a vector $a \in \mathbb{R}^n$ with weights vector $w \in \mathbb{R}^n$ subject to a set of non-contradictory constraints of the kind $x_i \leq x_j$.

The data staging engine 120 further comprises inflection point detection logic 220, inflection point selection logic 230, and epidemiological computer model parameter correlation logic 240. These elements 220-240 perform operations to automatically detect points, e.g., inflection points, in the smoothened data where the data indicates the influence of an external influence on the spread of the infectious disease, such as an intervention, lifting of a restriction, or the like, that may be cause for modifying epidemiological computer model hyperparameters and/or operational parameters. These elements 220-240 further perform operations to align epidemiological computer model parameters, e.g., hyperparameters and/or operational parameters, with the identified inflection points and smooth the transitions of the parameters between sub-sections of the data demarcated by these inflection points. The result is a set of parameter values, within the initializer ranges constraining the possible parameter values, of an epidemiological computer model for the various sub-sections of the infectious disease progression reflected in the smoothened infectious disease data patterns. The initializer ranges may be used to set initial values for the parameters of the epidemiological computer model for training purposes, i.e., the set of the ranges to specify the limits of the values for transmission rate, such that the hyperparameters and/or initial learnable operational parameter values for the epidemiological computer model are set to values within the specified ranges and then machine learning may be performed to learn the final state of the operational parameter values. The particular values to which the parameters are set within these initializer ranges may be part of a grid search operation, as discussed with regard to the learning engine hereafter.

The initializers, with regard to the hyperparameters, specify hyperparameter values reflecting assumptions of dynamics of the infectious disease and/or assumptions regarding population characteristics, e.g., mobility data, and/or interventions. For example, the initializers may specify the initial assumption on the correctness of the reported day 0 infected numbers, initial assumption on asymptomats to infectious people, etc. (i.e., the day 0 compartment values). The hyperparameters affect the parameters, i.e., parameters such as transmission rates of the infectious disease, infectious mortality rate, etc. It should be noted that although the parameter values may be different for each sub-section of the infectious disease and data patterns, the initializers (hyperparameter) are not time varying once fitted.

For example, during the course of the spread of an infectious disease, such as an epidemic or pandemic, the infection trajectory, i.e., the trajectory of numbers of incidents, numbers of fatalities, etc., may receive a series of "shocks" due to external interference to the course of infection, i.e., interventions, example of which includes various government policies, improved compliance of preventative measures like better hygiene practices, wearing masks in the case of air and aerosol borne infections, distribution of a vaccine, etc. Source data processing systems, e.g., 172 and/or 174 in FIG. 1, may provide databases of non-pharmaceutical interventions (NPIs), including date/time information, types of NPIs implemented, geospatial or geopolitical area of effect, and the like. It should be appreciated that not all interventions will necessarily be documented in these sources of NPI data, e.g., interventions such as changes in mobility pattern, improved civic sense to maintain physical distance and reduced interactions, etc., and the NPI data does not itself correlate the NPIs with "shocks" in the infectious disease data. As a result, epidemiological computer models only fit one set of parameters to capture the entire trend of the infectious disease and cannot accommodate discontinuities in the data, i.e., the epidemiological computer models assume an exponential growth curve.

Recognizing this deficiency in epidemiological computer models, the illustrative embodiments solve this issue by dividing the graph of infectious disease data patterns, i.e., curves, into "pieces", such that parameters corresponding to each piece represent the underlying characteristics of the disease progression during the corresponding time interval. The mechanisms of the illustrative embodiments detect the "shocks" in the infectious disease data patterns, and thus the boundaries of the "pieces", by analyzing the graph of infectious disease data patterns, or curves, to identify the inflection points in the curves, consolidate nearby "valleys" and "peaks", and finally filter these inflection points to retain only those that represent a change in the curve and not a momentary aberration, as well as retain only a predetermined number of these inflection points as specified in configuration data. The result is that the graph of the infectious disease data pattern is separated into sub-sections or "pieces" with the boundary of the sub-sections or pieces corresponding to points in time where an intervention is likely to have occurred.

The mechanisms of the illustrative embodiments then adapt the time sensitive parameters of the epidemiological computer model, such as transmission rate, case reporting rate, etc., to match the start and end time of these identified sub-section, i.e., the identified "discontinuities," and fit the data within each sub-section. The illustrative embodiments provide smoothening mechanisms, as previously described, that ensure that when these individual pieces or sub-sections of the fitted data are combined, the change in the epidemiological computer model parameters is a continuous and smooth transition from one sub-section to the next. In other words, there is a smoothening function around the curve discontinuities to ensure that the there is no sharp or abrupt changes in the epidemiological computer model parameters corresponding to the sub-sections of the graph for the infectious disease data patterns.

In particular, the inflection point detection algorithms implemented by the inflection point detection logic 220 operate on the smoothened input data to identify "knee" and "elbow" points in the smoothened input data, as previously described above. These inflection points may be identified by analyzing the data points in the smoothened input data curve to identify trends, e.g., slopes, in the curve representing abrupt changes in direction, e.g., negative slope to positive slope (elbow) or positive slope to negative slope (knee). The knee and elbow points represent discontinuities in the input data which are indicative of external influences on case reporting. These discontinuities may specify changes in numbers of incidents, changes in fatalities, changes in population mobility, etc., essentially changes in data for any graphs of the particular types of input data received from source computing systems, where these discontinuities are most likely caused by some other outside influence other than the infectious disease itself, i.e., interventions. For example, an abrupt reduction in incidents and/or mobility of the population may coincide with government mandates being imposed that restrict movement of the population, e.g., shelter in place orders. Moreover, a change in incidents may be due to imposing/lifting of closure requirements for bars/restaurants or other gatherings of individuals. Thus, by identifying inflection points in the cleaned/smoothened data, and correlating those inflection points with data specifying interventions and/or other outside influences, such as may be obtained from other knowledge databases, publicly available computing systems, or the like, the correlations may indicate which of the operational hyperparameters of the epidemiological computer model 110 may need to be modified and corresponding dynamic updating of the hyperparameters (e.g., transmission rates of the disease) and/or operational parameters of the epidemiological computer model 110 may be performed in an automated manner.

Figure 3:
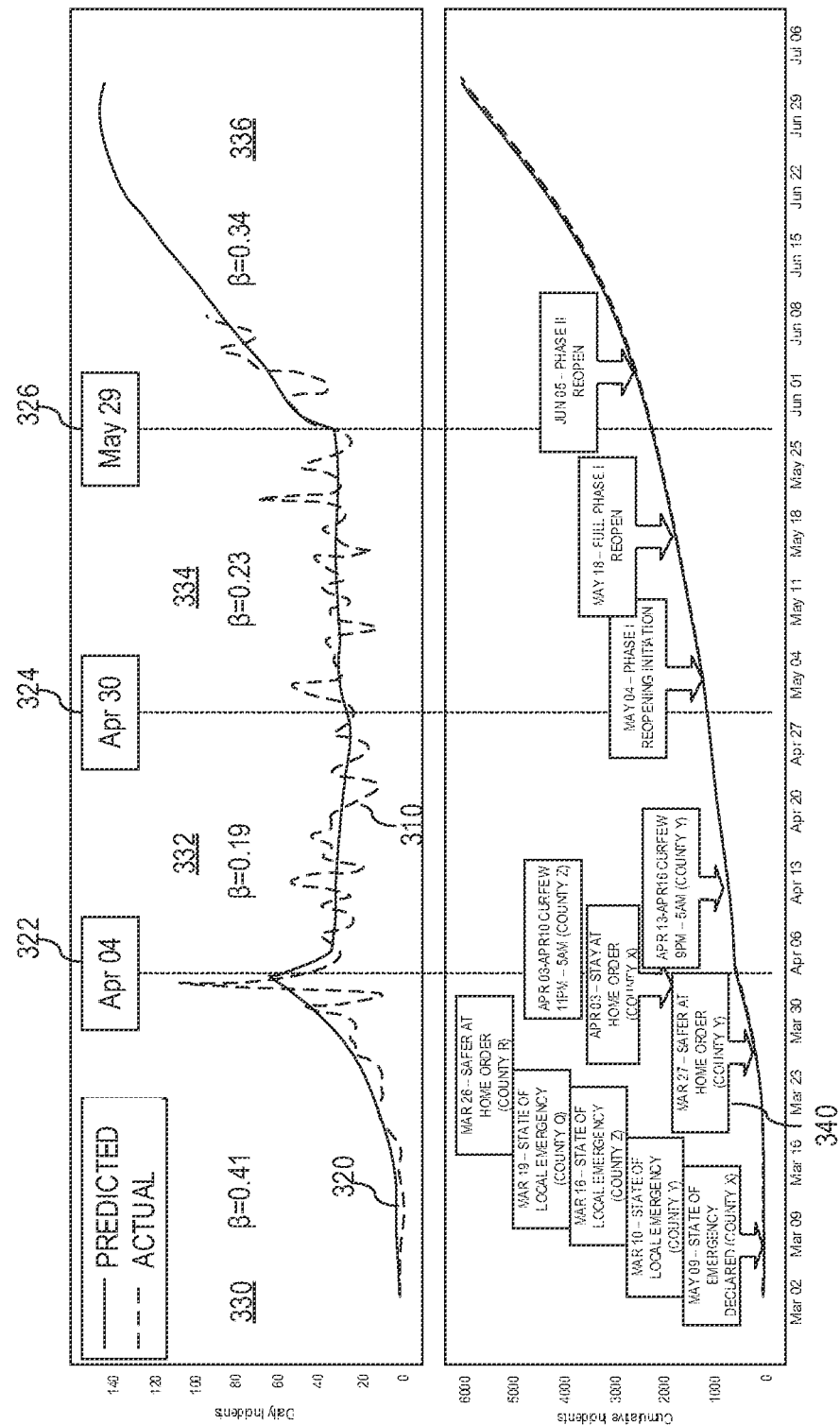
FIG. 3 is an example diagram depicting graphs of infectious disease data illustrating inflection points and corresponding interventions in accordance with one illustrative embodiment.

FIG. 3 is an example diagram depicting graphs of infectious disease data illustrating inflection points and corresponding interventions in accordance with one illustrative embodiment. FIG. 3 has two graphs of infectious disease data representing a spread of an infectious disease within a given region, which in this case is the geopolitical region of "County X". The top graph represents daily incidents of the infectious disease reported by health organizations within the region, where the vertical axis is the number of incidents and the horizontal axis is time. The bottom graph represents the cumulative incidents, which may be a rolling sum of the daily incidents. For each of these graphs, interventions experienced by the region are shown as boxed text and inflection points are shown as vertical lines at specified time points (along the horizontal axis). It should be appreciated that such graphs as shown in FIG. 3 may be provided as output to users via one or more user interfaces and thus, can graphically convey to users the inflection points, correlations of inflection points with particular types of interventions experienced by the region, and correlations of these types of interventions with particular epidemiological computer model parameters.

As shown in FIG. 3, the initial input data received, represented by curve 310, may have noise present in the data due to various factors, which causes the curve to have the many jagged portions depicted. Cleaning and smoothening algorithms and filters may be applied to this noisy data to generate a cleaned and smoothened curve 320 where the jagged portions are smoothed by removing spurious spikes in the data. While this data has been smoothened, significant changes in trends of the curves are maintained and are shown as inflection points 322 and 326 in the smoothened curve 320. An additional inflection point 324 is added to the representation of the graph based on epidemiologically curated rules applied to the data based on the identification of inflection points 322 and 326, e.g., based on rules specifying effective time ranges in which initializer ranges are appliable, which may in turn be based on time lags, efficacy time ranges, etc. between introduction of an intervention and when initializers are applicable and/or should be modified. Moreover, inflection points may be removed due to application of heuristic rules identifying conditions under which inflection points are most likely to represent external influences, e.g., no inflection points within 21 days of the presumed start of the infectious disease are retained, inflection points must be separated by at least 30 days, etc.

In addition, it should be appreciated that while the depiction in FIG. 3 is for a single county, the mechanisms of the illustrative embodiments may also utilize clustering of neighboring regions (counties) to generate a cluster or region group due to mobility of the population, such as may be determined from U.S. Census Bureau information or the like, regional healthcare institutions servicing multiple neighboring regions, sparsity of data in neighboring regions, or the like. Thus, in some illustrative embodiments, mechanisms are provided to generate an adjacency matrix data structure based on mobility data and the like, and this adjacency matrix may then be subjected to clustering to cluster neighboring regions where the individuals of the regions travel back and forth between the regions according to the mobility data, such that clusters or region groups are generated.

With regard to the types of inflection points shown in FIG. 3, inflection point 322 represents an "knee" inflection point as it has an initial positive slope with an abrupt downward slope on April $4^{th}$. Inflection point 326 represents an "elbow" inflection point as it has an initial negative or zero slope, and then an abrupt positive slope on May $29^{th}$. Inflection point 324 may also be considered an "elbow" inflection point on April $30^{th}$, but is not as abrupt as inflection point 326 and may be an inflection point inserted between inflection points 322 and 324 in accordance with epidemiologically curated rules as well as configuration data specifying a number of inflection points to maintain. As shown in FIG. 3, each inflection point 322-326 has associated interventions 340 that occur at time points corresponding to the inflection point. For example, an intervention 340 on April 3rd of "Stay-at-home order" occurs in a time frame close to inflection point 322.

The intervention data is obtained from source computing systems and has the timestamp data for when the intervention was enacted and potentially the duration of the intervention if the intervention has one. In addition, the inflection points 322-326 have corresponding timestamps associated with them such that they may be correlated with the interventions. Various rules may be executed to perform the actual correlation between the interventions and inflection points. For example, rules may specify that an intervention is associated with an inflection point as long as the intervention happened prior to the inflection point and within a specified period of time of the inflection point. There may be multiple interventions associated with the same inflection point.

Each sub-section 330-336 of the curve 320, defined as the sections of the curve 320 between inflection points or between an inflection point and an end of the graph, has a set of hyperparameter and/or operational parameter values, e.g., transmission rate or the like, that may be set according to specified initializer ranges. For ease of explanation, in the depicted example, a single parameter value, i.e., the transmission rate $\beta$, is represented in each of the sub-sections 330-336 of the curve 320. However, it should be appreciated that additional or replacement operational parameters (or simply "parameters") may be provided in a similar manner to that of the depicted transmission rate $\beta$. The parameter values prior to the first inflection point 330 may be default values used for modeling a particular infectious disease based on initial assumptions. The parameter values after the first inflection point 330 may be set according to clustering of similar regions and the initializers associated with similar interventions corresponding to the inflection points. For example, it may be determined based on historical analysis of similar regions that when a "Stay-at-Home Order" intervention occurred in a similar region, the infection rate increased by 0.04 and thus, the infection rate $\beta$ for 334 is increased from 0.19 in section 332 to 0.23 in section 334.

Returning to FIG. 2, initial configuration of the data staging engine 120 may specify the number of inflection points to maintain for epidemiological modeling. The inflection point selection logic 230 executes a set of epidemiologically curated rules for selecting inflection points from those identified by the inflection point detection logic 220 if more inflection points are identified than are permitted to be maintained by the configuration data. These rules may select inflection points to be maintained, for example, based on observed lag times for interventions and/or infectious disease dynamics to be represented in collected infectious disease data from source computing systems, e.g., a lag time from when infections occur and when cases are first reported, lag times from when interventions are introduced to when they have actual efficacy, and other periods of observed temporal conditions on the interventions, for example, changes in transmission rate may be sustained for three weeks, interventions do not occur in the early stages of the infectious disease spread, or the like. Thus, for example, if an inflection point occurs within 3 days of the first data point in the infectious disease data pattern, then this inflection point may be discarded as being in the early stages of the infectious disease and thus, interventions are unlikely, and the inflection point is most likely spurious. Similarly, inflection points that are at least three weeks between each other may be selected, but inflection points that are within three weeks of a previously selected inflection point may be discarded since it is known that transmission rates are sustained for three weeks (in the above example). Such epidemiologically curated rules may be manually defined and automatically applied by the inflection point selection engine 230. The inflection point selection logic 230 implements these epidemiologically curated rules in order to ensure that the assumptions and hyperparameter/operational parameter values are more epidemiologically reasonable to what is actually observed in response to interventions that may cause discontinuities in the infectious disease and/or population data.

The maintained set of inflection points generated by the inflection point selection logic 230 may be provided to the epidemiological computer model parameter correlation logic 240 which correlates the inflection points with information obtained from knowledge bases that maintain information regarding interventions that have been implemented on a regional basis. That is, one or more knowledge bases 270, such as may be maintained governmental or health organizations, may specify particular interventions that have been instituted for different regions (municipalities, counties, etc.) or clusters of regions (states, countries, etc.), time stamp information for the introduction of such interventions or observation of such interventions, and information specifying the regions affected by the interventions. For example, the knowledge bases 270 may comprise, in one illustrative embodiment, a plurality of government computing systems, each being associated with a different region or cluster of regions, such as local government computing systems or the like. The knowledge base 270 information may be accessed by the epidemiological computer model parameter correlation logic 240 via one or more interfaces (not shown) and used to correlate the interventions with the inflection points identified in the infectious disease data patterns and/or population data.

For example, the time stamp information for the interventions may be correlated with the time information for the inflection points to determine which interventions are most likely associated with the inflection points and the section of the curve after the inflection point. Thus, for example, if an inflection point is detected and maintained for time point t1, and an intervention has been recorded in the knowledge base 270 for a time point that is within t1-n, where n is a predetermined threshold time window, then that intervention may be associated with the inflection point.

The epidemiological computer model parameter correlation logic 240 may correlate the types of interventions corresponding to the inflection points with particular initializer ranges and/or model parameter values. The particular parameter values, within the initializer ranges, associated with a type of intervention may be determined by region clustering logic 242 of the epidemiological computer model parameter correlation logic 240 that clusters similar regions and determines interventions and corresponding hyperparameters/operational parameters used to model infectious disease progression with regard to these similar regions. For example, the region clustering logic 242 may cluster regions based on similarities in infectious disease data and/or population data to thereby identify regions having similar spread of the infectious disease and/or similar demographics and/or mobility with regard to the region's associated population. Those regions clustered together based on similarities of specified infectious disease characteristics and/or population characteristics may be further evaluated by the epidemiological computer model parameter correlation logic 240 to identify which similar regions experienced interventions of a same predefined type as the type correlated with the inflection point of interest, e.g., similar regions that experienced a "Stay-at-Home Order" intervention, where "Stay-at-Home Order" is the predetermined type, with examples of other predetermined types being "Phase 1 Reopening Initiation", "Full Phase 1 Reopen", "State of Emergency Declared", and the like (see further examples in FIG. 3). The corresponding model parameter values for the epidemiological computer model for the similar region at the specified time point may then be retrieved and used to adjust the parameter values for the current (target) region with regard to the inflection point.

The parameter values are determined from a specified initializer ranges of values for each of the hyperparameters and/or operational parameters according to a set of assumptions. For example, characteristics regarding the initial infected population, susceptible population, and disease characteristics may be assumed and specified in terms of the initializers in which the hyperparameters corresponding to these various characteristics are given a range of potential values. In some illustrative embodiments, the sets of initializers may be automatically generated based on historical analysis of previously observed trends in case reports and corresponding initializers found to generate accurate compartmental computer model predictions.

The clustering of similar regions by the region clustering logic 242 may also be used to make determinations as to whether or not the epidemiological computer model should be utilized for a given region. That is, the clusters may be evaluated by one or more statistical significance analysis computer models (see definition of "statistical significance" above) or the like, that determine whether the pre-processed input data for a region indicates sufficient case reporting trends, changes in trends, changes in applicable policies or other interventions, or the like, to warrant utilization of the predictive results of the epidemiological computer model based on the regions' data. If the one or more statistical models indicate that predictive modeling by the epidemiological computer model should be utilized, then clustering of regional data may be performed for sparsely populated regions or regions with sparsely occurring cases, based on workplace to residence transit data, mobility data, statistical areas like measurement statistical analysis (MSA) or core-based statistical area (CBSA), denoting groups of geo-units with intercity commute based on high business activity, or the like.

The determination of whether or not to utilize the modeling by the epidemiological computer model may be based on an evaluation of results of the epidemiological computer model 110 and a null hypothesis model 252 by a statistical significance analysis model 260. The statistical significance analysis model 260 performs operations to evaluate the results generated by the epidemiological computer model 110 based on the smoothened curve and the detected inflection points corresponding to inflections and assumes that there is community spread of the infectious disease, while the null hypothesis model 252 generates predictions based on an assumption that there is no community spread of the infectious disease and no implementation of additional interventions.

This use of the statistical significance computer model 260 on the predictions of the epidemiological computer model 110 and the null hypothesis model 252 is to perform a counterfactual analysis based on the observation that infectious disease dynamics are stochastic, i.e., have a random probability distribution or pattern that may be analyzed statistically but may not be predicted precisely. Before the start of a community spread in a region, imported cases from neighboring regions will show up and be reported, such as in case reports from source computing systems, e.g., 172 in FIG. 1. This leads to a time-series with stochastic case reports that arise not just from reporting noise, but also reporting the infection process itself, such as shown in FIG. 3 above. If the case report data is fitted to a known epidemiological computer model that includes the force of infection, i.e. the community spread of the infectious disease, these known epidemiological computer models will predict exponential growth and a future epidemic wave but will not properly account for transient "burnout", as imported cases are treated without triggering local community spread in the corresponding region. That is, these transient cases do not cause infectious disease spread in the region and effectively "burnout" without long term effect.

The solution, presented in the counterfactual analysis engine 250, is to test the counter hypothesis, or "background noise" model, e.g., the null hypothesis, that assumes a background imported infection rate=time average of the noise signal. That is, the counterfactual analysis engine 250 executes a "background noise model", which is similar in configuration to the epidemiological computer model, but which assumes that there is no community spread (null hypothesis) in the population of the region, and that reported cases are due to importation of the cases into the region. This background noise model is executed on the case report data to generate predictions if incidents and/or fatalities for the region based on this assumption of no community spread. The prediction results are compared to ground truth data that is gathered for the same time period as the prediction, e.g., if the prediction is a prediction of incidents/fatalities for the next day, then after the next day's case report data is received from the source computing systems, this newly received case report data for the target region may be used as a ground truth for comparison to the background noise model's predictions that were previously generated. This ground truth data may be actual case report data received from source computing systems for the same time period as the prediction results and are used as a check of the accuracy of the background noise model prediction results. That is, the fitted error of the background noise model is determined along with other statistical measures of accuracy, such as the predicted mean absolute percentage error, or the like.

In accordance with one illustrative embodiment, the fitted error and predicted mean absolute percentage error (MAPE), determined by comparing the prediction results of the counter hypothesis, or background noise, computer model to a ground truth comprising the actual case report data for the same time period as the prediction results, are evaluated to determine if they are lower for the background noise model than for the epidemiological computer model with community spread disease dynamics (force of infection), i.e., the fitted error and MAPE for the epidemiological computer model executed on the same case report data is used as a threshold value against which the fitted error and MAPE of the background noise model is compared. If so, then the framework, via the statistical significance computer model 260, continues to select the background noise model and its predictions, i.e., the null hypothesis computer model 252, for reporting of prediction results. In response to evidence of exponential growth in the case report data, i.e., community spread is occurring in the target region, leading to an equal or lower MAPE and an equal or lower fitted error for the epidemiological computer model, i.e., the epidemiological computer model with community spread disease dynamics has an equal or lower MAPE and equal or lower fitted error than the background noise model, does the framework switch, or utilize, via the statistical significance computer model 260, the epidemiological computer model 110 and its predictions for reporting model predictions, i.e., the model assuming community spread of the infectious disease is selected as it is more accurate to the real world data being reported.

Figure 4:
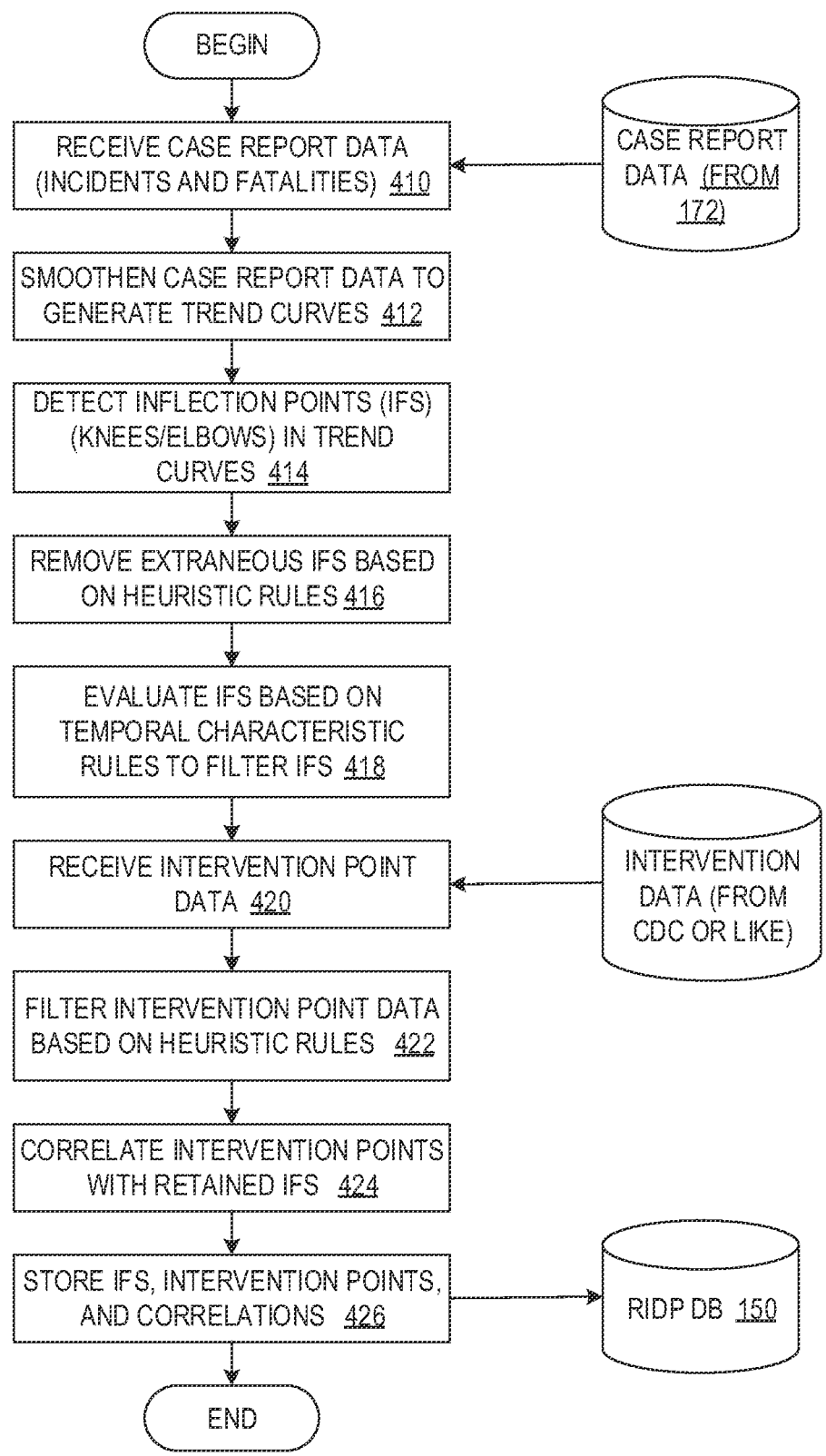
FIG. 4 is a flowchart outlining an example operation of a data staging engine with regard to correlating inflection points in input data with interventions in accordance with one illustrative embodiment.

FIG. 4 is a flowchart outlining an example operation of a data staging engine with regard to correlating inflection points in input data with interventions in accordance with one illustrative embodiment. The operation outlined in FIG. 4 may be implemented, for example, by logic and mechanisms of the data staging engine described above with regard to FIGS. 1 and 2. As shown in FIG. 4, the operation starts by receiving case report data specifying incidents, e.g., new detections of individuals being infected with the infectious disease, and fatalities (step 410). This case report and fatality data may come from source computing systems, such as source computing systems 172 in FIG. 1, for example. The incidents and fatalities are referred to collectively herein as case report data.

As shown in FIG. 4, the case report data is smoothened to generate trend curves (step 412) and inflection point detection is then executed to identify inflection points in the trend curves (step 414). Extraneous inflection points are then filtered out based on heuristic rules (step 416). The retained inflection points are then evaluated based on temporal characteristic rules and configuration data specifying characteristics of the inflection points to maintain, such as a predetermined number of inflection points to retain (step 418). The temporal characteristic rules may specify time periods where if an inflection point is present within that time period, the inflection point is discarded, e.g., within 7 days of the assumed infectious disease start, inflection points that are within 30 days of each other, etc.

The operation further receives intervention data to identify intervention points (step 420), such as from source computing systems, such as the CDC databases or computing systems, local government databases, health organization computing systems, or the like. The intervention point data may be filtered based on heuristic rules (step 422) to identify the interventions that are of interest. The intervention data comprises timestamp information which is then used to correlate the intervention points with the retained inflection points based on heuristic rules (step 424). The correlations between the inflection points and the interventions may then be stored in the RIDP database (step 426) for further use.

Figure 5A:
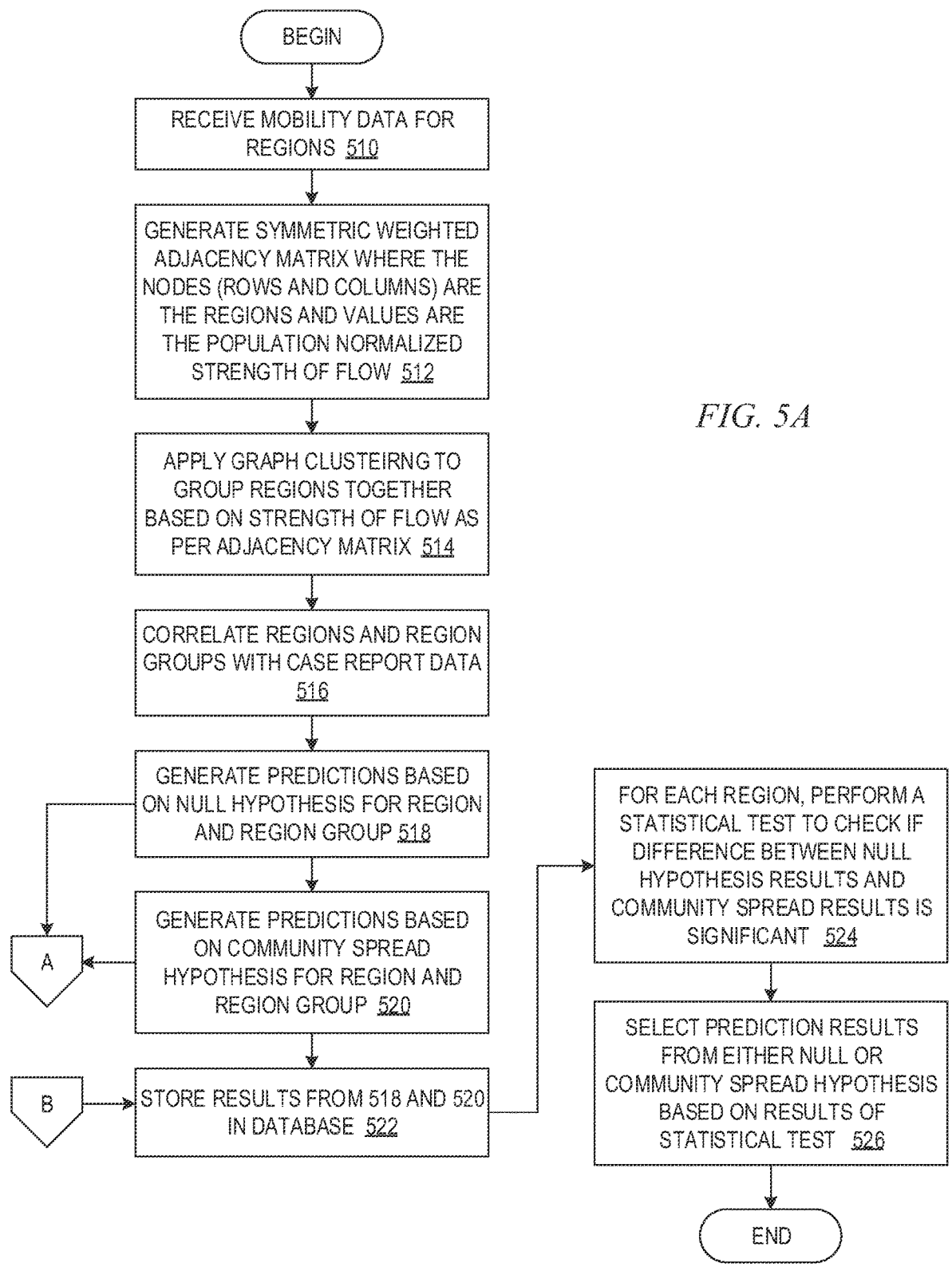
FIGS. 5A and 5B are a flowchart outlining an example operation of a data staging engine with regard to performing counterfactual analysis in accordance with one illustrative embodiment.
Figure 5B:
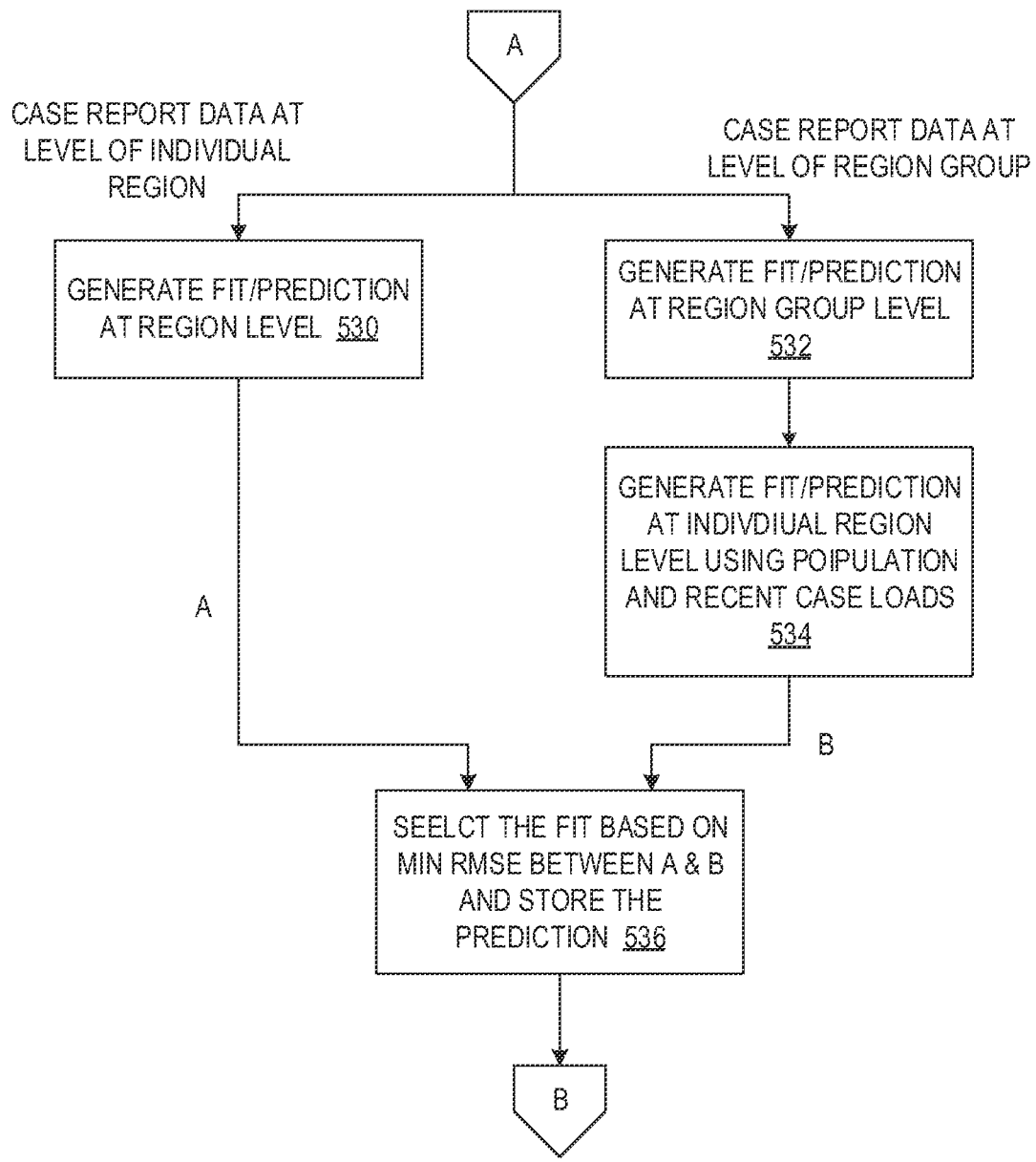

FIGS. 5A and 5B depict a flowchart outlining an example operation of a data staging engine with regard to performing counterfactual analysis in accordance with one illustrative embodiment. The operation outlined in FIG. 5 may be implemented, for example, by logic and mechanisms of the data staging engine described above with regard to FIGS. 1 and 2. As shown in FIG. 5A, the operation starts by receiving mobility data for regions (step 510). This data may have already been collected from source computing systems, such as mobility tracking services and the like, and stored in the RIDP database 160 and retrieved from the RIDP database 160 as part of the operation of step 510. In some illustrative embodiments, the mobility data may be obtained from the census bureau or other source computing system of a similar type, and may include mobility data specifying locations for home and work for individuals, whether the individuals commute to work and home, etc., such that clustering of regions may be performed.

Having received the mobility data for the regions 510, in order to determine whether to cluster regions and then actually perform the clustering, the operation generates a symmetric weighted adjacency matrix for the target region, where the nodes (rows and columns) are the regions, and the values are the population normalized strength of flow (step 512). Thus, the adjacency matrix identifies for a target region, the other regions to which the population travels. The adjacency matrix may be a symmetric matrix to represent commuting from one region to another and vice versa. The adjacency matrix facilitates the clustering or grouping of regions based on where individuals travel to get to work and go home. In some illustrative embodiments, with greater granularities of mobility data indicating other regions where individuals travel, e.g., for shopping, entertainment, to obtain services, and the like, this matrix may take into consideration additional regions other than just home and work regions for the individuals of a target region.

A graph clustering algorithm is applied to the adjacency matrix to group regions together based on the strength of flow (step 514). The resulting regions and region groups are then correlated with case report data to thereby generate case report data for individual regions and for region groups (step 516). For example, if a target region is the Bronx, New York, it may be the case that individuals commute to other boroughs of New York City to work, e.g., to Brooklyn, Manhattan, Queens, and Staten Island. The adjacency matrix specifies the strength of flow of the population of the Bronx to these other boroughs and the clustering algorithm determines based on this adjacency matrix, which of these boroughs (regions) should be clustered together with the Bronx.

Thereafter, predictions are generated based on a null hypothesis (step 518) and based on a community spread hypothesis (step 520) for the regions and region groups. The operation for performing these predictions is similar, as shown in FIG. 5B, but is performed under different hypotheses and thus, using different models. For example, the null hypothesis uses a "flat line" model in which it is assumed that there is no community spread of the infectious disease and thus, the number of infections over time stays constant. The community spread hypothesis assumes that individuals are mixing at a rate determined based on the mobility data for the population and thus, there is a growth rate in the number of infections. The community spread hypothesis uses the epidemiological computer model to generate predictions of numbers of infections, cumulative numbers of infections, and fatalities. The null hypothesis uses a statistical model assuming no growth rate.

Going to FIG. 5B, whether for the null hypothesis or the community spread hypothesis, the operation performs parallel paths of operation, one for case report data at the level of the individual region (path A), and one for case report data at the level of the region group (path B). For path A, the operation generates a prediction at the region level, i.e. using case report data for the individual region and the corresponding model, e.g., epidemiological computer model or statistical model based on no growth, and determines the fit of the prediction to the ground truth (step 530), e.g., generates the root mean square error (RMSE) for the prediction relative to the ground truth, which in this case is the actually reported number of incidents, cumulative incidents, and fatalities for the particular time point being modeled.

For path B, the operation generates a prediction using the case report data for the region group, and the corresponding model, and determines the fit of the prediction to the ground truth (step 532). In addition, path B determines the prediction and fit for the individual region level using the population and recent case load information for that region, from the prediction/fit of the region group level (step 534). For example, the ratio of population and case load for the individual region may be used to estimate the regional level prediction and fit from the region group level prediction and fit. This is done so that the fit/prediction for the region and the region group can be accurately compared in step 536 so that the fit having the minimum RMSE between paths A and B can be selected and stored for use (step 536). It should be appreciated that while the flow states that the selected fit/prediction is stored, as all 3 predictions/fits are generated in steps 530-534, all for these may be stored for later use with one of them being selected as the best prediction for the region. Thus, the operation in FIG. 5B determines which is better for a particular region, evaluating the region alone or within a regional group with other neighboring regions. Performing these operations for both the community spread and the null hypothesis assists in determining whether or not community spread more accurately represents the real-world dynamics of the infectious disease for the region, e.g., the infectious disease is in fact spreading with the region or region group, or whether the instances of cases in the region are due to transient portions of the population and thus, the null hypothesis is more accurately reflective of the real-world dynamics.

Returning to FIG. 5A, the results from steps 518 and 520, represented in FIG. 5B, are stored in the RIDP database (step 522). For each region, a statistical significance test is performed to determine if the difference between the null hypothesis results and a ground truth, or the difference between the community spread results and the ground truth, is significant (step 524). Based on the results of the statistical significance test, prediction results and the model to be used for the region are selected, e.g., the model that does not exhibit a statistically significant difference from the ground truth is selected (step 526). The operation then terminates.

It should be appreciated that while the above description of the performed operations is provided as being part of the epidemiological computer model data generation engine, some of the operations may in fact be performed by the learner engine 130 in FIG. 1 either alone or in concert with the epidemiological computer model data generation engine. For example, in some illustrative embodiments, the operations of FIG. 5B may in fact be performed as part of the grid search 123 in FIG. 1. Moreover, steps 524-526 may in fact be performed as part of the selection logic 124 of the learner engine 130. As shown in FIG. 1, the grid search logic 123 works in conjunction with the epidemiological computer model 110 which may also include the null hypothesis model as a model instance with a null hypothesis set of assumptions being implemented. Based on the selection of which models provide better results, e.g., community spread versus null hypothesis, and region level versus region group level, the corresponding model parameter values may be selected and stored in the RIDP database 160 as a best set of parameters for modeling the region using the model 110.

Epidemiological Computer Model

As mentioned previously, the epidemiological computer model 110 of FIG. 1, in some illustrative embodiments, may be a compartmental computer model, such as a SIR, SEIR, or other compartmental computer model. In some illustrative embodiments, the epidemiological computer model 110 may be a compartmental computer model that has been augmented to take into consideration the isolation of the population as determined from mobility data, where this mobility data may be data that is not necessarily tied to the infectious disease modeling, e.g., the mobility data may be data collected for other purposes but which is integrated into the modeling of the infectious disease via an augmented compartmental computer model.

When the epidemiological computer model is invoked to generate predictions as to infectious disease state, the instance of the epidemiological computer model invoked may be initialized according to a corresponding set of initializer ranges and parameter values selected from these initializer ranges, and may operate on infectious disease data (e.g., incident data from case reports) and population data (e.g., mobility data) stored in the RIDP database 160 in FIG. 1. In accordance with the inflection points identified by the data staging engine and stored in the RIDP database 160, the initializers may be modified over the time period modeled by the epidemiological computer model so as to more accurately reflect the disease state and generate more accurate predictions for future disease states. The inflection points indicate where the disease dynamics have changed. This allows the framework to adjust the parameters of the epidemiological computer model dynamically around those time points to get the best fit curves or trends for infectious disease dynamic characteristics and project such trends for future predictions. If there were no inflection point detection according to the illustrative embodiments, the framework would fit one transmission rate for the entire period of the infectious disease spread, e.g., for the entire time period of a pandemic. This would not only result in an inaccurate, or "bad", fit of the trend curves, but is also epidemiologically incorrect as the underlying disease dynamics continuously evolve over time. Changing the parameters daily may provide a good fit, but will not give a good prediction as the parameters learned may be in a state of flux and the curve fitting will be fitting noisy data, or "chasing the noise." Thus, being able to identify inflection points indicative of when infectious disease dynamics actually have changed and automatically adapting to the new disease dynamics parameters, in accordance with the illustrative embodiments, solves this issue by not modifying the parameters too often, and at an arbitrarily determined time interval, and not modifying the parameters at too infrequent a time period causing inaccurate assumptions of infectious disease dynamics, but instead dynamically adapting to the actual changes in infectious disease dynamics.

Figure 6:
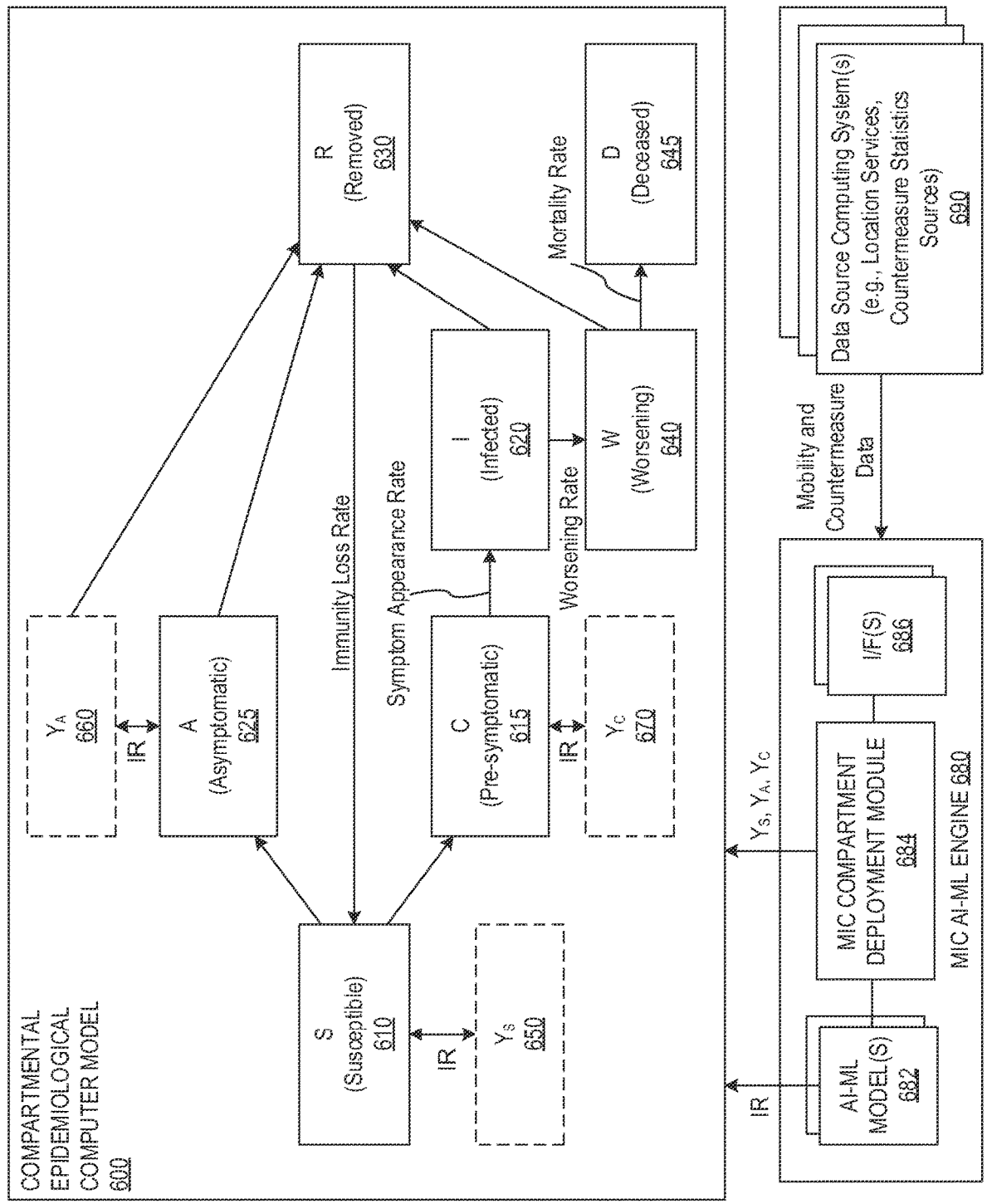
FIG. 6 is an example block diagram of a compartmental epidemiological computer model in accordance with one illustrative embodiment.

FIG. 6 is an example block diagram of a compartmental epidemiological computer model in accordance with one illustrative embodiment. The epidemiological computer model is shown as a set of connected boxes representing different compartments, where each compartment has a population of individuals whose state, with regard to the progression of the infectious disease being modeled, corresponds to a pre-defined state of progression of the disease, e.g., susceptible, asymptomatic, pre-symptomatic, infected, recovered/removed, worsening, deceased, etc. Connections between the boxes represent the flow, or transitions, from one state to another, with each connection having a transition rate indicating the amount of flow over time of individuals in a first connected compartment into a second connected compartment. Each of the connected boxes have corresponding computing logic associated with them for modeling the population of the compartment and the transitions to/from the compartment.

The particular compartmental epidemiological computer model shown in FIG. 6 represents a computer model representation of Corona Virus Disease 2019 (COVID-19). However, it should be appreciated that this is only an example, and the mechanisms of the illustrative embodiments may be implemented with an epidemiological computer model for any infectious disease that is the subject of computer modeling, such as influenza, west Nile virus, the common cold, severe acute respiratory syndrome (SARS), or any of a plethora of other infectious diseases. Moreover, the depicted computer model has specific compartments and transitions between compartments that are for an example implementation of the COVID-19 epidemiological computer model and other epidemiological computer models may have different compartments from those shown in FIG. 6, yet are intended to be within the spirit and scope of the present invention.

As shown in FIG. 6, similar to the SIR model discussed previously above, the example illustrative embodiment in FIG. 6 has compartments 610, 620, and 630 for susceptible individuals (S), infected individuals (I), and recovered/removed individuals (R), respectively. In addition, compartments 615 and 625 are provided to represent the pre-symptomatic individuals (C) and the asymptomatic individuals (A). The susceptible individuals (S) 610 represent the portion of the population P that have not been determined to be infected and thus, are not asymptomatic (yet infected), pre-symptomatic (yet infected), infected, or have been removed/recovered, i.e., are immune to the infectious disease. The asymptomatic individuals (A) 625 represent the portion of the population P that have been infected but are not showing any symptoms of the disease, i.e., they are asymptomatic, or are individuals that are unreported. The individuals in compartment A 625 represent potential spreaders of the infectious disease due to these individuals being infected but not knowing of the infection since they do not show symptoms.

The pre-symptomatic individuals (C) 615 represent the portion of the population P that have been infected but are not showing symptoms of the disease yet because the disease is in an incubation time frame of the disease within the individuals, e.g., some individuals may be infected, yet not show symptoms for a few days after being infected. Again, these individuals in compartment C 615 represent potential spreaders of the infectious disease due to these individuals being infected but not knowing of the infection since they are not exhibit symptoms yet.

The infected individuals (I) 620 represents the portion of the population P that have been infected and are showing symptoms of the disease. The removed/recovered individuals (R) 630 represents the portion of the population P that were infected (e.g., asymptomatic or infected) but have recovered and thus, are immune. It should be appreciated that for some diseases, such as COVID-19, there is a possibility of a loss of immunity, such as due to variants of the disease or the like, and this is represented by a transition from the removed/recovered compartment 630 back to the susceptible compartment 610.

In addition to these compartments 610-630, compartment W 640 represents a portion of the population P that is infected and whose condition is worsening. This worsening compartment W 640 represents the time delay between when an individual is infected and shows symptoms of the infection, and when the individual dies from the infectious disease, represented by the deceased (D) compartment 645. That is, there is a time period where the health of the individual worsens over time before the individual dies of the disease, and this is represented by compartment W 640.

Transitions or connections between compartments 610-645 represent a flow of portions of population from one state of the disease to another. Each of these transitions have transition rates associated with them that represent the number of individuals per time unit whose state of the disease changes from an initial state (tail of the arrow) to a changed state (head of the arrow). For example, the transition from the susceptible compartment S 610 to the asymptomatic compartment A 625 represents the number of individuals per time unit that are infected by do not show any symptoms.

As shown in FIG. 6, the compartments 610-645 may include compartments for susceptible (S) portions of the population, infected (I) portions, asymptomatic (A) portions, pre-symptomatic (C), removed/recovered (R) portions, worsening (W) portions, deceased (D) portions, and the like. As described hereafter, this compartmental computer model may further include corresponding isolation compartments (Y), also referred to herein as mobility isolation and countermeasure (MIC) compartments, that model interventions causing isolation of portions of the population. As the time scale is continuous, interpolation functions are added on any of the tertiary sources that directly control the flow, e.g., changes in mobility that controls population movement or transitions T from a first compartment, for example compartment S, to a second compartment, for example compartment Y. An example of these equations, in accordance with one illustrative embodiment, may be the following set:

$$T_{Y \to S} = \max(0, f_{mob}(t)) \quad (1)$$

$$T_{S \to Y} = \max(0, -1 * f_{mob}(t)) \quad (2)$$

where $f_{mob}$ is the fitted function used to extrapolate mobility data to get likely mobility values in the future. The compartment flow rates may be defined, in one illustrative embodiment, for the compartments, as the following:

$$\frac{dS}{dt} = -\beta * \frac{S*(I+A+C)}{N} + \rho*R + \min(Y, T_{Y \to S}*(S+Y)) =$$

$$\min(S, T_{S \to Y}*(S+Y))$$

$$\frac{dY}{dt} = \min(S, T_{S \to Y}*(S+Y)) - \min(Y, T_{Y \to S}*(S+Y))$$

-continued $$\frac{dA}{dt} = (1-\xi)*\left(\beta*S*\frac{I+A+C}{N}\right) - \gamma_A*A$$

$$\frac{dC}{dt} = (\xi)*\left(\beta*S*\frac{I+A+C}{N}\right) - \alpha*C$$

$$\frac{dI}{dt} = \alpha*C - (\gamma_I + \omega)*I$$

$$\frac{dW}{dt} = \omega*I - (\mu_d + \gamma_W)*W$$

$$\frac{dR}{dt} = \gamma_I*I + \gamma_A*A + \gamma_W*W - \rho*R$$

$$\frac{dD}{dt} = \mu_d*W$$

where $\beta$ is a time varying transmission rate parameter, $\rho$ is an immunity loss rate, $\xi$ is a case reporting rate, $\omega$ is a time delay, $\gamma$ is a recovery rate from the respective compartment state, $\mu_d$ is a death rate, and the values S, I, A, C, W and Y are the populations of the corresponding compartments, and N is a total population. The transmission rate represents the likelihood that a person will be infected, and the case reporting rate represents the likelihood that a person will be tested for the infectious disease if not showing symptoms. This is just an example of one set of differential equations that may be used to model aspects of an infectious disease using a compartmental model, and are not intended to be limiting on the illustrative embodiments. Many modifications may be made to these examples without departing from the spirit and scope of the present invention.

The data needed to determine the transition rate from S 610 to A 625 may be obtained, for example, from case reporting performed by health and/or governmental organizations which collect such data, such as the Centers for Disease Control (CDC), World Health Organization (WHO), hospital networks, state and local government organizations, or the like. As an example, the transition rate from compartment S 610 to compartment A 625 for COVID-19 may be determined from historical statistical data gathered by one or more data collection source computing systems, such as data gathered and reported by the CDC and/or WHO, which specifies case reports where the individual reported no symptoms but tested positive for the virus. Such data may be obtained from source computing systems 172 in FIG. 1, for example.

Similarly, such statistical data from case reporting data gathering and reporting computing systems, such as the CDC and/or WHO computing systems, may also specify individuals that tested positive and then showed symptoms as well as the time delay between testing positive and showing symptoms, which indicates the incubation time of the disease and can be used to determine the transition rate from compartment S 610 to compartment C 615, and then from compartment C 615 to compartment I 620. The transition from compartment C 615 to compartment I 620 represents the symptom appearance rate. Moreover, such statistical data from case report gathering and reporting computing systems may include other data specifying statistics as to immunity loss of recovered/removed individuals, numbers of infected individuals that die from the disease, and timing, such as numbers of days between infection and death/recovery. The various rates associated with the transitions may be determined from these statistics and gathered case report data in a manner readily apparent to those of ordinary skill in the art.

It can be appreciated from the above description that the portions of the population P that are present in the various compartments 610-645 at any one time is dependent upon the modeling of the spread of the disease based on the transitions between compartments 610-645, which in turn is based on the time dependent case reporting and time dependent determined transmission rate of the disease, i.e., how much an infected person will infect the population P over a given period of time. The transmission rate of the disease is determined based on an assumption that the population is not restricted in its mobility and thus, each individual has the same amount of opportunity to infect the same amount of the population P over a given period of time. However, when compared to the reality of mobility restrictions, such as lockdowns, self-isolation, and the like, such assumptions render the modeling of the disease inaccurate. Moreover, various countermeasures that may be employed by individuals within the population P may lessen the ability of the infectious disease to spread throughout the population P, e.g., reduction in public transport, reduced store hours, wearing masks, social distancing, etc.

In accordance with the illustrative embodiments, as touched upon above, additional mobility isolation and countermeasure (MIC) compartments 650-670 are provided to model a realistic adjustment to the portions of the population P that are present in selected compartments 610-645 of the compartmental epidemiological computer model 600. For example, in the depicted compartmental epidemiological computer model 600, MIC compartment $Y_S$ 650 is connected with compartment S 610, MIC compartment $Y_A$ 660 is connected with compartment A 625, and MIC compartment $Y_C$ 670 is connected with compartment C 615. Thus, MIC compartment 650 represents the portion of the population of S that is not mobile (e.g., currently under a lockdown order from the government, perform self-isolation due to co-morbidities, or the like) and/or is implementing countermeasures to the disease (e.g., washing hands, wearing masks, social distancing, etc.) as determined from real-world data, as discussed hereafter. Transitioning a portion of the population of compartment S 610 to MIC compartment 650 takes that portion of the population out of the flow from compartment S to compartment A or compartment C as those individuals are not susceptible to infection by the disease due to them not being exposed to the infectious disease through assumed free mingling with other individuals in the population. It should be appreciated that the connection between compartment S 610 and MIC compartment 650 is a two-way connection since the transition is time dependent, e.g., lockdown orders are imposed/lifted, intensified, etc., and individuals in greater/lesser numbers engage in self-isolation and countermeasures, e.g., mask mandates may be lifted and thus, individuals may stop wearing masks making them more susceptible.

Similar considerations apply to the other MIC compartments 660 and 670. MIC compartment 660 represents the portion of the population of asymptomatic individuals in compartment 625 that are not mobile or are engaged in countermeasures to help lessen the spread of the infectious disease. By transitioning a portion of the population of compartment A to MIC compartment 660, the transitioned portion represents the portion that is not spreading the disease to others. Similarly, by transitioning a portion of the population of compartment C 615 to MIC compartment 670, the transitioned portion represents the portion of pre-symptomatic individuals that are not spreading the disease to others. Thus, by moving population from compartments 615 and 625, the population transitioned does not contribute to the force of infection.

The MIC compartments 650-670 are pluggable into an existing compartmental epidemiological computer model 600 and do not require additional parameters for the compartmental epidemiological computer model 600. To the contrary, the MIC compartments 650-670 represent compartments in which a sub-portion of the populations in each of the attached compartments of the epidemiological computer model 600 are placed due to restrictions in mobility and/or countermeasures employed by the corresponding portions of the population of those epidemiological computer model compartments. Thus, in order to integrate the MIC compartments 650-670 into a compartmental epidemiological computer model 600, all that is needed is to know which compartments of the epidemiological computer model 600 are to have associated MIC compartments, e.g., compartments 610, 615, and 625 and corresponding MIC compartments, e.g., MIC compartments 650-670, may be automatically generated for these designated compartments in the compartmental epidemiological computer model.

The characteristics, e.g., transitions rates, of the transitions from and to these epidemiological computer model compartments to and from the MIC compartments 650-670 are learned through the application of trained AI-ML based computer models 682 of a MIC AI-ML engine 680 that take gathered mobility and countermeasure data from data source computing systems 690 and predict the mobility and countermeasure use of the population over time. The MIC AI-ML engine 680 comprises a MIC compartment deployment module 684 that deploys the MIC compartments, such as MIC compartments 650-670, into the compartmental epidemiological computer model 600 based on configuration information specifying which compartments of the compartmental epidemiological computer model are to have their flows modified by isolation rates determined by the trained AI-ML based computer models 682 of the MIC AI-ML engine 680, such as compartments 610, 615, and 625 of the depicted example epidemiological computer model 600. In this way, the MIC compartments 650-670 are deployed into an epidemiological computer model in a plug-in manner and do not require modification of the existing epidemiological computer model. The MIC AI-ML engine 680 further includes interfaces 686 for obtaining mobility and countermeasure data from data source computing systems 690.

The AI-ML based computer model(s) 682 may be trained, through a machine learning based process, such as supervised machine learning, based on historical mobility data and countermeasures use statistics data, to predict the transition rate to/from MIC compartments 650-670. These transition rates represent the rate at which individuals are isolated, due to externally imposed or self-imposed isolation measures, and/or the rate at which individuals isolate themselves from becoming infected or spreading the infectious disease by use of countermeasures. These transition rates are time dependent, and patterns of these transition rates may be learned over time such that timing factors may also be included in the AI-ML based computer model(s) 682, e.g., the infectious disease may not be spread as easily in warmer months of the year than in colder months of the year, the infectious disease may be spread at a higher rate over holiday weekends, etc.

The mobility data gathered from the data source computing systems 690 may be mobility data that is collected through known mobility and/or location detection and monitoring systems based on tracking of mobile computing devices associated with individuals of a monitored population, which may be an entire population or a subset of a population of a given geographical region, for example. It should be appreciated that the mobility data does not need to be tied to the spread of diseases, let alone the spread of the particular infectious disease being modeled by the compartmental epidemiological computer model. To the contrary, the mobility data may be general mobility data that is concerned with representing how mobile a given population is. For example, the mobility data may simply represent locations of mobile devices over a predetermined period of time. An individual within the mobility data may be considered "mobile" if their location changes by a predetermined amount, and the number of times that the location changes by the predetermined amount over the predetermined period of time meets or exceeds a predetermined threshold amount, e.g., the individual travels equal to or more than 5 miles at least 5 times within a week time period.

Numbers or percentages of individuals classified as mobile within the population may be tracked over time to determine how these numbers or percentages change over time such that learned associations between mobility and other time-based factors may be determined and thus, predictions of mobility based on time-based factors may be made by the trained AI-ML based computer model. Moreover, mobility may be mapped, through the AI-ML based computer model, to a transition rate for the transitions to/from the MIC compartments from/to the compartments of the epidemiological computer model. For example, it may be determined that mobility of individuals falls from one time period to another time period by 3%. Thus, a greater number of individuals, e.g., 3% more, should transition from compartment S 610 to MIC compartment 650, however in another time period the mobility may increase by 2% such that the transition from compartment S 610 to MIC compartment 650 should be reduced, e.g., reduced by 2% which, given the example 3% increase mentioned above gives a net transition from compartment S 610 to MIC compartment 650 of 1% increase over a baseline. The change in the mobility, although observed at discrete time periods (e.g., daily), is transformed into a continuous function for the AI-ML based computer model such that the mobility may be queried to get the change in the mobility at any time instance (e.g., any fraction of the day).

Thus, the AI-ML based computer model(s) 682 are trained through machine learning to identify patterns in input features indicative of different levels of isolation. These features may be extracted from data gathered from various data source computing systems 690 and may include features such as levels of mobility of individuals specified in one or more types of mobility data from data source computing systems 690 and/or countermeasure data specifying statistical measures of the population with regard to implementing one or more countermeasures for isolating individuals from being infected or infecting others, e.g., wearing masks, using hand sanitizer, washing hands, social distancing, and the like, of the population. The AI-ML based computer model(s) 682 determine or predicts an isolation rate based on the identified patterns, which is then applied to the connections between the selected compartments of the epidemiological computer model 600, e.g., compartments 610, 615, and 625 in FIG. 6, to thereby modify the populations of these compartments by transitioning individuals from the compartments 610, 615, and 625 to corresponding MIC compartments 650-670 according to the isolation rate. It should be appreciated that as individuals in the population take more measures to isolate themselves from each other and take countermeasures to reduce the spread of the infectious disease, the isolation rate increases and thus, more of the population of the compartments in the epidemiological computer model 600 transition to the MIC compartments 650-670. As individuals in the population reduce measures to isolate themselves from each other and/or relax countermeasures, the isolation rate decreases and thus, less of the population of the compartments in the epidemiological computer model 600 transition to the MIC compartments 650-670 and/or more of the population of the MIC compartments 650-670 transitions based to the corresponding compartments 610, 615, and 625 of the epidemiological computer model 600.

In some illustrative embodiments, the data source computing systems 690 comprise computing systems that gather and report mobility data of mobile devices associated with individuals of a monitored population. For example, location services, such as provided by Google™ or Apple™ in association with their mobile phone devices may be used to track movements of individuals in a population, given authorization of these individuals to such tracking of movements. Such mobility data may be used to determine statistical representations of the amount and degree of mobility of the monitored population which may then be used with the AI-ML based computer model 680 to predict isolation rates for transitioning populations in compartments of an epidemiological computer model into and out of MIC compartments 650-670 which model the isolation of the population.

It should be appreciated that the mobility data is not limited to mobility data gathered from the tracking of movement of mobile computing devices by mobility and/or location tracking services. Other mobility data that may be used includes vehicular traffic information that may be gathered and reported by highway management organizations, toll road management organizations, airline reservation systems, or any other source of data indicative of the general mobility of a population. Various different types of mobility data may be used together to obtain a representation of the mobility of a given population or at least a subset of the population. For example, features extracted from each type of mobility data may be provided as inputs to the AI-ML computer model(s) 682 as input features in which the AI-ML computer model(s) 682 identify patterns for correlating with different levels of isolation and predicted isolation rates.

The same is true of countermeasures data which may comprise various types of countermeasure data such as statistics on mask wearing, statistics on hand washing, statistics on hand sanitizer usage, statistics on social distancing, etc. Features extracted from each of these different types of countermeasure data may be input to the AI-ML computer model(s) 682 as separate countermeasure features in which the AI-ML computer model(s) 682 identifies patterns and for correlating with different levels of isolation and predicted isolation rates.

Moreover, in some illustrative embodiments, the AI-ML computer model(s) 682 may comprise a plurality of differently trained AI-ML computer models 682 for separately processing mobility data and countermeasure data. In other illustrative embodiments, the AI-ML computer model(s) 682 may comprise a single AI-ML computer model 682 that receives a combination of feature inputs of both mobility and countermeasure data as input upon which the single AI-ML computer model 682 operates to predict an isolation rate. In the case of an illustrative embodiment in which a plurality of differently trained AI-ML computer models 682 are utilized, the AI-ML computer models 682 may further include aggregation logic that aggregates the isolation rate predictions generated by the other AI-ML computer models 682 in the plurality. The particular function for aggregating the predictions may be implementation dependent and may also be trained using a machine learning of empirical methodology. For example, the function may be a weighted aggregation function that applies different learned weight values, learned through machine learning or empirical evaluation, to different ones of the isolation rate predictions generated by the other AI-ML computer models 682.

Thus, the illustrative embodiments provide an additional AI-ML computer model mechanism that augment and improve compartmental epidemiological computer models. The mechanisms of the illustrative embodiments provide for granular modeling of adjustments to flow parameters according to temporal changes in isolation features of a population, e.g., features indicating the mobility of the population and countermeasures instituted by individuals of the population. It should be appreciated that this granular and temporal modeling of isolation features may be performed for various levels of geographic regions. For example, different AI-ML computer models 680 may be provided for different populations for different geographical regions, such as cities, counties, states, countries, territories, continents, etc., i.e., any desired population.

The mechanism of the illustrative embodiments provide additional AI-ML computer model logic that provides for automatic tuning of flow parameters governing flows of portions of a population between compartments of a compartmental epidemiological computer model. In some illustrative embodiments, the automatic tuning is implemented by providing MIC compartments which model the relative isolation of individuals of the population due to restrictions on mobility and/or countermeasures instituted. As new data is gathered and reported by data source computing systems 690, the flow parameters are automatically updated by the AI-ML computer model logic which predicts isolation rates based on identified patterns in features extracted from the gathered and reported data. Such modeling may also predict for a future time what the likely isolation rate will be based on expected input features at that time, as determined from historical data. For example, temporal features may be input to the AI-ML computer model 680 which, having learned from historical data patterns of isolation rates increase/decrease during different times, may use these temporal features to determine a timing for the prediction and, along with other input features, such as those extracted from current mobility data and countermeasure data, predict an isolation rate for a future time.

By incorporating realistic mobility and countermeasures data into the modeling of infectious diseases via compartmental epidemiological computer models through the implementation of the isolation rate prediction mechanisms and MIC compartment mechanisms of the illustrative embodiments, improved accuracy in the epidemiological projections are made possible. That is, the inaccuracies in epidemiological computer models due to the unrealistic assumptions of a freely interacting population when isolation measures and countermeasures are implemented by individuals of the population. Thus, for example, for any given time point, the portions of a population that are present in each compartment of the epidemiological computer model may be determined, e.g., indicating how much of the population is susceptible, infected, asymptomatic, pre-symptomatic, recovered, worsening, deceased, etc., and these values will be more accurate than existing epidemiological computer models since the improved computer modeling of the illustrative embodiments takes into consideration the actual mobility of the population and actual implementation of countermeasures by the population, factors which both affect the flow of portions of the population into and out of compartments of the epidemiological computer model.

Figure 7:
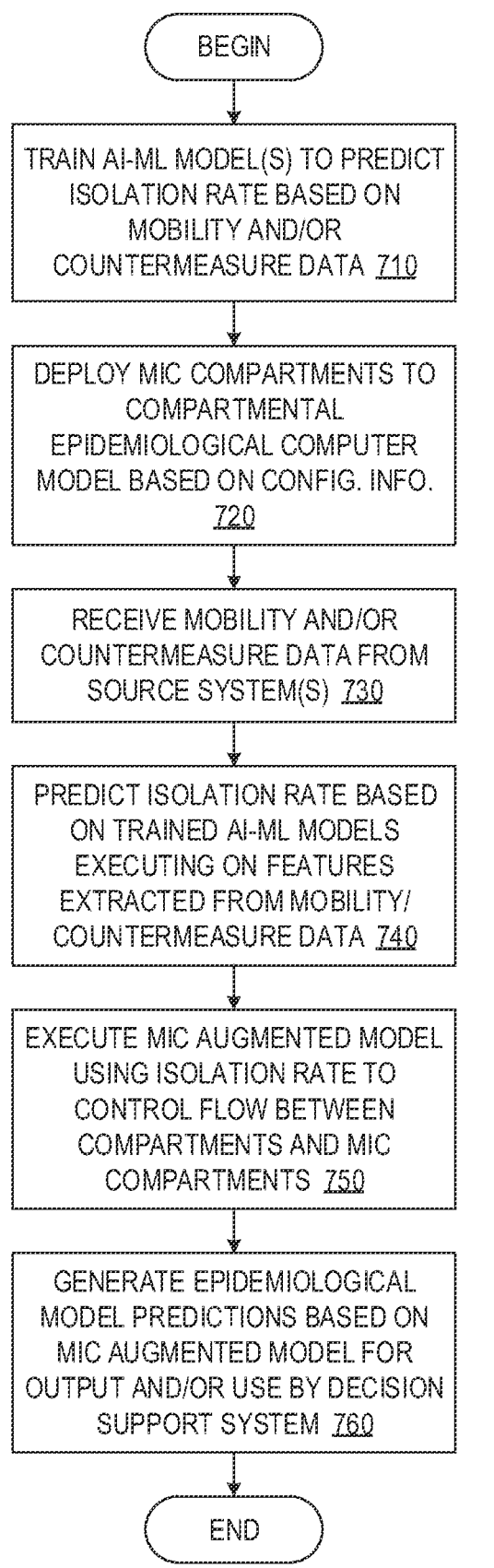
FIG. 7 is a flowchart outlining an example operation of a mobility isolation and countermeasures augmented epidemiological computer model in accordance with one illustrative embodiment.

FIG. 7 is a flowchart outlining an example operation of a mobility isolation and countermeasures augmented epidemiological computer model in accordance with one illustrative embodiment. The operation outlined in FIG. 7 may be implemented by a mobility isolation and countermeasures (MIC) artificial intelligence-machine learning (AI-ML) based engine in accordance with one illustrative embodiment, such as MIC AI-ML engine 780 in FIG. 6, for example. It should be appreciated that the operations outlined in FIG. 7 are specifically performed automatically by an improved computer tool of the illustrative embodiments and are not intended to be, and cannot practically be, performed by human beings either as mental processes or by organizing human activity. To the contrary, while human beings may initiate the performance of the operation set forth in FIG. 7 and may make use of the results generated as a consequence of the operations set forth in FIG. 7, the operations in FIG. 7 themselves are specifically performed by the improved computing tool in an automated manner.

As shown in FIG. 7, the operation starts by training, through a machine learning process, AI-ML computer model(s) to predict isolation rates based on mobility and/or countermeasure data (step 710). The machine learning operation may include the use of training data and known, i.e., ground truth, data indicating correct results to be generated by a fully trained AI-ML computer model. The training data is input to the AI-ML computer model, processed to generate a prediction of isolation rates, and the prediction is compared to the ground truth to determine an error or loss between the prediction generated and the correct prediction. The operational parameters of the AI-ML computer model that contributed to the prediction are then adjusted to attempt to reduce this error to or below an acceptable level as defined by a threshold error value. This process is repeated through multiple epochs until the AI-ML computer model converges, i.e., error is equal to or below the threshold, or a predetermined number of epochs are performed. At this point, the AI-ML computer model is determined to be trained. The AI-ML computer model may then be tested or verified using a testing/verification data set, and if the performance of the AI-ML computer model is satisfactory, the AI-ML computer model is deployed for runtime use.

Step 710 in FIG. 7 is intended to cover this process, the result of which is a set of one or more trained AI-ML computer model(s) that are able to generate predictions of isolation rates based on a set of features input to the model, where these features may include features extracted from mobility and/or countermeasure data, such as previously described above. In some illustrative embodiments, the one or more trained AI-ML computer model(s) may be a single trained AI-ML computer model that operates on both features extracted from mobility and countermeasure data, while in other illustrative embodiments separate AI-ML computer models are used for mobility and countermeasure data features. In some illustrative embodiments, only one or the other of mobility and/or countermeasure data may be utilized to predict isolation rates.

It should also be appreciated that other input features may be utilized as well, such as temporal input features, that provide additional basis for pattern recognition in the input features and corresponding prediction of isolation rates. During runtime processing, such additional features may be obtained from parameters of the compartmental epidemiological computer model that is being executed. For example, the compartmental epidemiological computer model may be executed for a future time in order to predict the state of an infectious disease with regard to a given population at this future time. The future time, as well as other parameters, may be provided as additional input features to the trained AI-ML computer model(s) which may use the training of the AI-ML computer model(s) based on historical patterns of progression of an infectious disease and patterns of mobility and/or countermeasure use over time as an additional factor in predicting isolation rates.

Based on configuration information for the deployment of mobility isolation and countermeasure (MIC) compartments into a given compartmental epidemiological computer model, MIC compartments are deployed into the compartmental epidemiological computer model to simulate portions of populations that are isolated due to lack of mobility and/or implementation of countermeasures (step 720). That is, portions of the population are not freely intermingling with other portions of the population, or are taking precautions that effectively isolate them from the other individuals of the population with regard to spreading of an infectious disease. Thus, these individuals are simulated by the MIC compartments and the isolation rates. The deployment of MIC compartments may comprise generating the MIC compartments and providing an interface between the computer logic of the MIC compartments and the computer logic of the compartments to which the MIC compartments are connected in the compartmental epidemiological computer model. The particular compartments in the compartmental epidemiological computer model to which the MIC compartments are connected may be specified in the configuration information for the deployment.

Having deployed the MIC compartments, mobility and/or countermeasure data is obtained from data source computing systems, such as location services computing systems, government reporting computing systems, and the like, and features are extracted from the received data for use by the trained AI-ML computer model(s) (step 730). The extracted features are input to the trained AI-ML computer model(s) which generate isolation rate predictions based on the features (step 740). The generated isolation rates are then used in the execution of the MIC compartment augmented epidemiological computer model to control the flow of portions of population into/out of the MIC compartments (step 750). The compartmental epidemiological computer model augmented with the MIC compartments executes to generate predictions of infectious disease and population state which may then be output for use by a human user, e.g., a display of the results may be generated, or output to a decision support computing system (AI computing system) which may perform additional operations based on the predictions (step 760). For example, in illustrative embodiments where the output is provided to a decision support computing system, the decision support computing system may automatically generate recommendations for curtailing the predicted spread of the infectious disease. The operation then terminates.

It should be appreciated that the illustrative embodiments specifically utilize AI-ML computer models that are trained through machine learning processes to predict an isolation rate based on features from mobility and/or countermeasure data. The specific AI-ML computer models utilized will depend on the desired implementation and may be of various types. For example, the AI-ML computer models may be convolutional neural networks (CNNs), deep neural networks (DNNs), Support Vector Machines (SVMs), random forest computer models, rules-based engines with machine learning used to learn parameters of the rules, or any other currently known or later developed machine learning based computer model used to implement artificial intelligence operations.

It should as be appreciated that while the primary illustrative embodiments are directed to modeling infectious diseases with regard to human populations, the illustrative embodiments are not limited to such. To the contrary, the epidemiological computer models with which the mechanisms of the illustrative embodiments may be implemented may be used to model infectious diseases for any biological organism, such as the spread of viruses within animal populations or the like.

Report Generation and Scoring Engine

The epidemiological computer model operates to generate predictions of infectious disease state, e.g., numbers of incidents, cumulative number of incidents, fatalities, etc., based on the case report data and population data from the various source computing systems. Moreover, the epidemiological computer model operates based on initializer ranges setting model parameters (initial hyperparameter and/or operational parameter values) specified for various time points corresponding to interventions associated with inflection points in the input data as described previously. The epidemiological computer model generates predicted results, such as predictions of numbers of individuals classified into the various compartments of the compartmental computer model of FIGS. 6 and 7 above. Thus, by modeling the infectious disease, taking into account mobility data, and taking into account changes to hyperparameters and/or operational parameters of the model based on interventions, the epidemiological computer model may identify numbers of susceptible persons, numbers of infected persons, numbers of recovering/removed persons, numbers of fatalities, etc. for a future time point. These results may be presented to a user via the report generation and scorer engine 130 in FIG. 1, for example. In addition, the report generation and scorer engine 130 may provide logic for implementing hypothetical scenario investigations and providing recommendations to users based on these hypothetical scenario investigations.

Figure 8:
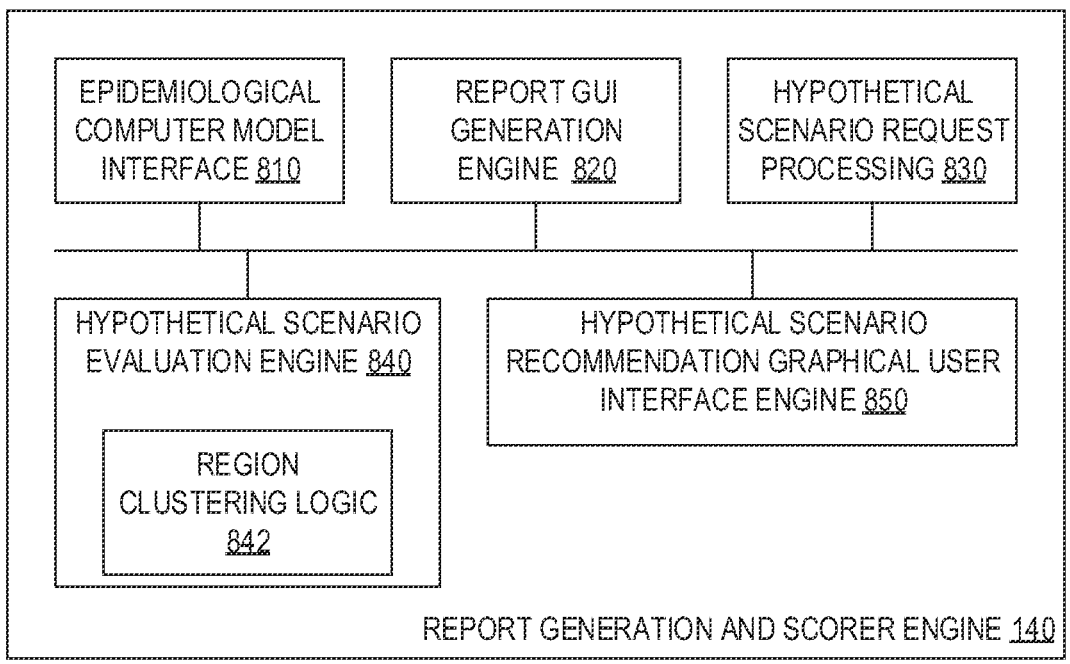
FIG. 8 is an example block diagram of a report generation and scorer engine in accordance with one illustrative embodiment.

FIG. 8 is an example block diagram of a report generation and scorer engine in accordance with one illustrative embodiment. As shown in FIG. 8, the report generation and scorer engine 130 comprises an epidemiological computer model interface 810, a report graphical user interface generation engine 820, a hypothetical scenario request processing engine 830, a hypothetical scenario evaluation engine 840 comprising region clustering engine 842, and a hypothetical scenario recommendation graphical user interface engine 850. The epidemiological computer model interface 810 provides a data communication interface through which results data from the epidemiological computer model may be received for report generation, and through which requests may be sent to the epidemiological computer model for executing the model to generate predictions with particular modifications corresponding to hypothetical scenarios.

With regard to report generation, the epidemiological computer model may provide predicted results, such as previously described above with regard to FIGS. 6 and 7, and these results may be reported in one or more graphical user interfaces (GUIs) for viewing by a user. While a visual GUI is assumed for purposes of this description, it should be appreciated that the output of the report generation and scorer engine 130 may comprise graphical, textual, audible, and in some illustrative embodiments, tactile output, such as in the case of output for visually impaired persons. The reports may include data in a graphical format similar to that shown in FIG. 3 previously, with graphical representations of predicted infection disease dynamics, representations of subsets of the population with regard to the various defined compartments of the epidemiological computer model, predicted statistics and trend information for the infectious disease, timelines and corresponding intervention information, and/or the like. The results data comprising the various predictions that are generated by the epidemiological computer model are received via the interface 810 and processed by the report GUI generation engine 820 to generate a report output that may be presented to a user, such as via a user interface (not shown). The report and GUI may take various different forms depending on the desired implementation, but in general may provide graphical representations of trends and predictions based on the trends, provide textual descriptions, graphical user interface elements for receiving user input, such as virtual buttons, text fields, user selectable options for defining hypothetical scenarios, desired views of the data, graphical user elements for drilling down into the data represented by the textual, graphical portions of the report, etc. Moreover, in some illustrative embodiments, the graphical user interface may further be paired with audible outputs, video output, or the like. Any suitable manner for outputting a representation of the results generated by the epidemiological computer model instance(s) and providing a mechanism for receiving user input may be used without departing from the spirit and scope of the present invention.

In addition to the ability to present reports of predictions generated by the epidemiological computer model, the report generation and scorer engine 130 also provides logic for performing hypothetical scenario evaluation. For example, the report GUI generation engine 820 may output a report GUI with user interface elements allowing a user to specify conditions of a hypothetical scenario that the user wishes to model to determine how changes in interventions and/or infectious disease state will modify predictions generated by the epidemiological computer model. Such hypothetical scenarios may assist users in decision making with regard to interventions that should be considered to modify infectious disease spread within a given population, e.g., the population of the modeled region or cluster of regions. Evaluation of these hypothetical scenarios, in accordance with some illustrative embodiments, leverages historical data corresponding to similar regions to determine how hyperparameters and/or operational parameters of the epidemiological computer model should be modified to model the hypothetical scenario.

For example, during the course of an epidemic or pandemic, regions are going from one infectious disease spread wave to another, in some cases accompanied by similar or different interventions imposed by governments, or in some cases with similar or different behavior of people. There are a number of important questions that various stakeholders may ask in order to plan for the future. For example, a hospital in a region may want to know, without any government intervention, what is going to be the duration and the magnitude of the second wave of the infectious disease so that they can plan for life saving equipment ahead of time. As another example, a vaccine trial company may want to know where to plan for locations with future high incidence and low prevalence for trial of vaccine several months ahead of time. In still another example, a county official may want to know what would be the likely impact of a planned large event in the region, or the impact of certain vaccination rates on the trajectory of the disease, or even how to achieve certain reductions in infectious disease spread by enacting certain interventions and which interventions to enact, or the consequences of lifting restrictions.

The illustrative embodiments provide a solution that learns changes in historical epidemiological parameters derived from an epidemiological computer model instance for a similar region during different phases of the infectious disease (e.g., epidemic or pandemic) and applies these historical epidemiological parameters to an instance of the epidemiological computer model for the current region to generate predictions for the current region should similar interventions be implemented and/or lifted in the current region. Moreover, the illustrative embodiments provide mechanisms to perform counterfactual analysis to study possible future trajectories of disease evolution.

Via the report GUI generated by the report GUI generation engine 820, the illustrative embodiments may present to the user, such as in the form of a set of rules that user can try out, options for defining hypothetical scenarios for the epidemiological computer model to model and generate predictions. Alternatively, an unstructured text input box may be presented via the GUI such that the user can enter free-form text requests that may be processed by natural language processing (NLP) logic of the hypothetical scenario request processing engine 830, to extract natural language features specifying the conditions of the hypothetical scenario and match those features to historical data maintained in the RIDP database 160 or the like.

The predefined options presented via the GUI may mimic past situations or allow a user to override those conditions. For example, the illustrative embodiments may present to the user a set of historical changes in the transmission rate parameters when the pandemic was growing slowly, e.g., transmission rate went up from 0.15 to 0.35 indicating rapid increase if there are no restrictions. The illustrative embodiments may present the user with a set of historical changes in the transmission rate parameters when other interventions were introduced, but may have been lifted, e.g., previously an occupancy restriction of 25% was introduced which reduced the transmission rate by X, and then the occupancy restriction was lifted to 50% which increased the transmission rate by Y. These options may be presented in a selectable manner such that the user can define a hypothetical scenario in which similar interventions, lifting of restrictions, or the like, are implemented based on the current data for the target region or region group.

Whether input through GUI based selections, or freeform textual input, or the like, the user is able to define, via the reports generated by the report GUI generation engine 820, a hypothetical scenario comprising a set of characteristics of the infectious disease state, interventions, and population state, that they wish to explore. The hypothetical scenario request processing engine 830 may receive this definition of the hypothetical scenario and automatically convert the hypothetical scenario definition into a set of epidemiological computer model parameters for an instance of the epidemiological computer model that models the hypothetical scenario. The hypothetical scenario request processing engine 830 maps the user input to scenario characteristics, which may require natural language processing of any unstructured textual requests to extract features which may then be mapped to scenario characteristics. For example, if the user enters text of the sort, "how do I reduce transmission rate by 50%", the hypothetical scenario request processing engine 830 may use natural language processing to extract features of "reduce", "transmission rate", and "50%" and use these features to perform a lookup operation in a database of previous interventions used to achieve a desired result.

For example, the RIDP database 160 may store, for each region, historical data specifying interventions and their corresponding results for the regions. The hypothetical scenario request processing engine 830 may perform a lookup operation in the RIDP database 160 entries for interventions that resulted in a reduction of the transmission rate by 50% or more. This may be done with regard to the target region as well as similar regions, where similar regions may be determined based on a similarity analysis of region infectious disease state and population state characteristics as previously mentioned above, e.g., regions having similar demographics of population, similar infectious disease spread, and the like. These similar regions need not be neighboring regions and may in fact be remotely located from one another, but still has similar characteristics. The similarity of regions may be determined by the region clustering logic 842 of the hypothetical scenario evaluation engine 840 which performs clustering of regions based on specified characteristics, such as population age, population gender, population ethnicity, population economic level, transmission rate of infectious disease, fatalities, etc.

The parameters used to configure the epidemiological computer model for these regions given the interventions/lifted restrictions specified in the entries found through the lookup operation may be modeled by the hypothetical scenario evaluation engine 840 by executing instances of the epidemiological computer model configured with parameters corresponding to the target region or the similar regions, but executed on data for the target region. The best performing, e.g., least RMSE, set of parameters for the epidemiological computer model may be selected. The best performing model parameters may be used to then configure the instance of the epidemiological computer model that provides predictions for the hypothetical scenario, and may be executed on the target region data to generate predictions and recommendations regarding the particular policies (interventions) that can be implemented and which one(s) are the best performing and the results of implementing these policies. These predictions and recommendations may be presented to the user via the hypothetical scenario recommendation graphical user interface engine 850.

Hence, the user is able to specify the hypothetical scenario at a high level of abstraction, e.g., "tell me what intervention I should use to reduce region A's transmission rate by 50%", and the mechanisms of the illustrative embodiment translate this request into model parameters. The user is not required to know anything about how to set model parameters or what changes to make to evaluate a what-if or hypothetical scenario. The user need only select or enter the characteristics of the scenario they wish to investigate from a high level, not a model parameter level, and the predictions are made using the best performing model parameters from historical data for the target region and similar regions.

Figure 9:
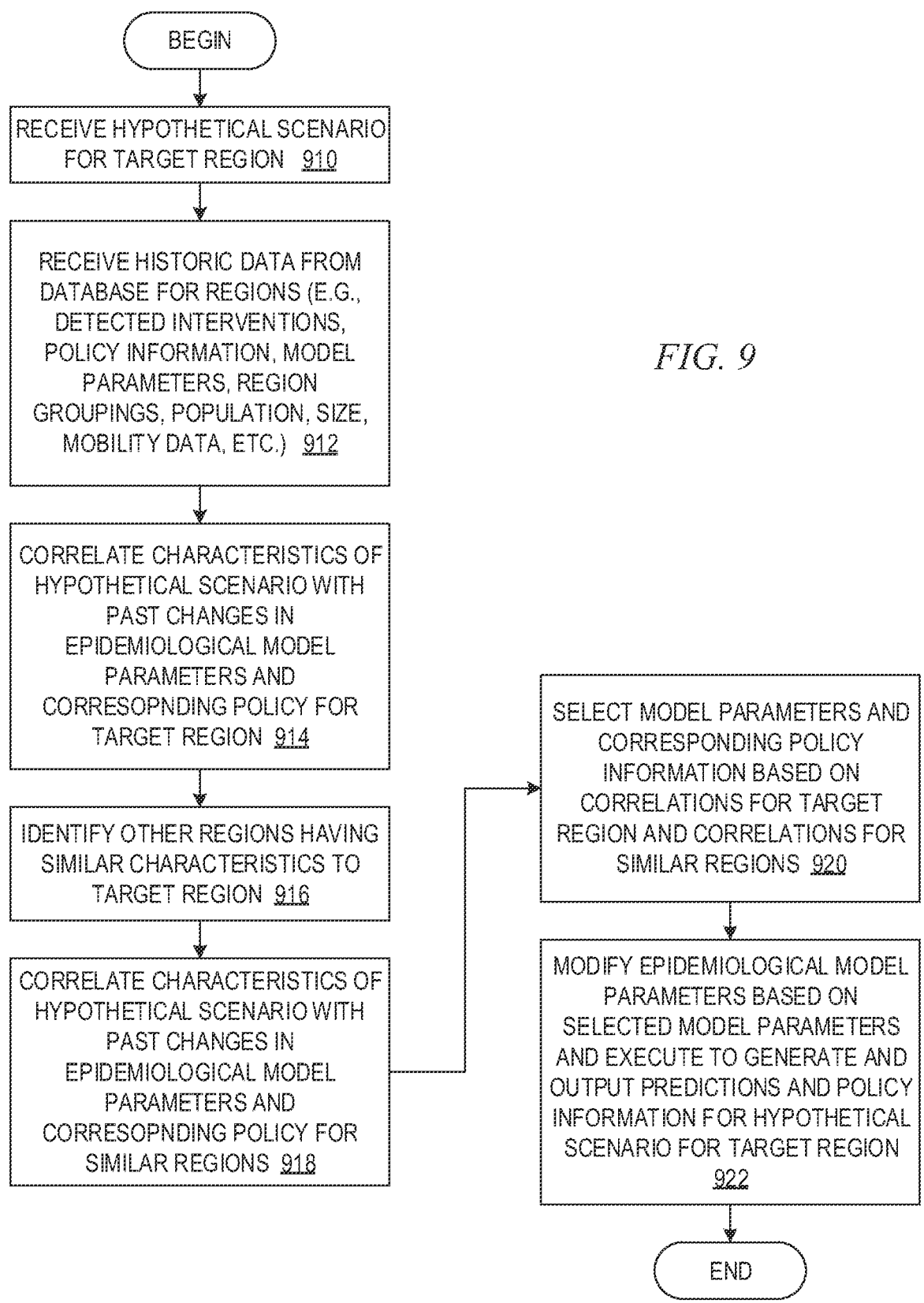
FIG. 9 is a flowchart outlining an example operation of a report generation and scorer engine with regard to performing hypothetical scenario evaluations in accordance with one illustrative embodiment.

FIG. 9 is a flowchart outlining an example operation of a report generation and scorer engine with regard to performing hypothetical scenario evaluations in accordance with one illustrative embodiment. As shown in FIG. 9, the operation starts by receiving a hypothetical scenario for a target region (step 910). The historic data regions are retrieved from the RIDP database (step 912). The characteristics of the hypothetical scenario are the correlated with past changes in the epidemiological model parameters and corresponding policy for the target region (step 914). Other regions having similar characteristics to the target region are determined, such as through the region clustering discussed above (step 916). Characteristics of the hypothetical scenario are correlated with past changes in epidemiological computer model parameters and corresponding policy for similar regions (step 918). Model parameters are then selected based on the corresponding policies for the target and similar regions (step 920). The epidemiological model parameters are then modified based on the selected model parameters and executed to generate and output predictions and policy information for the hypothetical scenario for the target region (step 922). The operation then terminates.

Continuous Monitoring Engine

As described previously with regard to FIG. 1, the illustrative embodiments provide mechanisms that operate to automatically and continuously monitor the predictions and performance of the epidemiological computer model 110 to determine when retraining of the epidemiological computer model 110 needs to be performed. The continuous monitoring engine 150 provides automatically executed computer logic to monitor the predictions and performance of the epidemiological computer model 110 both with regard to continuous adjustment of the model parameter values within the initializer ranges specified for the epidemiological computer model 110, as well as determining when an update to these initializer ranges needs to be made because assumptions used to set the bounds of these initializer ranges are no longer accurate to the real-world conditions of the infectious disease spread. By employing these automated computer tools to perform continuous updating, the epidemiological computer model is continuously maintained as accurate as possible to the observed real-world conditions such that it can make accurate predictions and generate results that are the basis of accurate recommendations to decision makers.

With regard to the continuous monitoring of the epidemiological computer model 110 to adjust parameter values for the epidemiological computer model 110 within the initializer ranges, the continuous monitoring engine 150 comprises automatically executed computer logic that compares the prediction results generated by the epidemiological computer model 110, and provided to the report generation and scoring module 140, to a ground truth to determine if the prediction results are, or are not, tracking with real-world observations. In this evaluation, the ground truth represents the actual reported data from the source computing systems 172 for the time point or period, e.g., the actual observed numbers of incidents, cumulative incidents, and/or fatalities. Thus, the continuous monitoring looks at the predictions generate and compares them to the actual data to determine how well the epidemiological computer model 110 did in predicting the actual data.

The continuous monitoring engine 150 executes statistical test logic to determine if the deviation between the predictions generated by the epidemiological computer model 110 and the actual observed real-world data reported by the source computing systems 172 is statistically significant. For example, the statistical test of significance performed by the statistical test logic may be a t-test or the like, as previously described above, whose corresponding p-value would indicate if the result of the test is significant or not for a predetermined threshold, e.g., 95%, 99% or the like. This evaluation may be performed for each prediction and adjustments of model parameters within the initializer ranges may be triggered each time there is a statistically significant deviation detected. In other illustrative embodiments, this evaluation may be performed for each prediction and a count of statistically significant deviations may be generated such that once a predetermined threshold number of statistically significant deviations are determined to have occurred, automatic adjustment of model parameters within the initializer ranges may be performed and the count reset. This alternative embodiment may be used in cases where it is desired to make sure that a statistically significant deviation is not due to an aberration.

In response to determining that one or more of the deviations in the predictions of the epidemiological computer model 110 from the reported real-world data from the source computing systems 172 is statistically significant, an operation for adjusting epidemiological computer model parameters, e.g., hyperparameters and/or operational parameters, is automatically executed by the continuous monitoring engine 150. This process involves generating multiple instances of the epidemiological computer model 110, each configured with a different set of model parameters according to a grid search type operation, such as depicted in 133 of FIG. 1, where the values of the model parameters are constrained by the initializer ranges defined for the epidemiological computer model. These instances of the epidemiological computer model 110 involves training the instances via the learner engine 130 to generate separate trained instances of the epidemiological computer model 110, including the original parameter values but with retraining of the model 110.

The instances of the epidemiological computer model 110 may be executed as new real-world data is received from the source computing systems 172 to evaluate the performance of the instances of epidemiological computer model 110 relative to the new real-world data (which is implemented as the ground truth). The performance of the instances relative to the ground truth may again be determined using the statistical tests for significance and assigning scores to each of the instances corresponding to the deviations. For example, a higher score may be assigned to an instance for instances that generate greater deviations from the real-world data (ground truth), relative to other instances and their corresponding deviations. Scores that are greater than a predetermined threshold, or top X number of scoring instances may be eliminated from further use. That is, the instances of the epidemiological computer model 110 having the highest statistically significant deviations may be discarded. The remaining instances may have their predictions combined in a weighted manner so as to generate a single prediction for the newly received data. The weights assigned to each remaining instance may be based on the scoring of the instance, i.e., the historical tracking of how well that instance generates predictions relative to the real-world data. The weights may be calculated based on a combination of a previously assigned weight and an adjustment function based on the current scoring of the instance.

In this way, the instances of the epidemiological computer model 110 may be pruned in an iterative manner to eliminate instances that generate statistically significant deviations from the actual real-world data until a single instance is selected as the final retrained instance of the epidemiological computer model 110. This final retrained instance of the epidemiological computer model 110 is then used as the new baseline instance of the epidemiological computer model 110 from which other instances are generated, such as for hypothetical scenario evaluation, grid searches, or the like. Hence, the illustrative embodiments provide automated computing tools to continuously maintain the epidemiological computer model parameters to be accurate to the actual observed real-world data and thus, provide more accurate predictions as to the spread of the infectious disease.

While these mechanisms allow for automatic adjustment of the epidemiological computer model parameters within the given initializer ranges, it is recognized that in some instances, the initializer ranges themselves may become inaccurate. That is, the initializer ranges are initially set based on a set of assumptions. These assumptions are necessary at the early stages of a spread of an infectious disease precisely because not all characteristics of the infectious disease are known until the spread is tracked from some period of time. Moreover, it should be appreciated that as the infectious disease is investigated over time, more revelations about the infectious disease itself, as well as the manner by which the infectious disease spreads within a population, are acquired, which may indicate that previous assumptions were not accurate or are no longer accurate due to dynamic changes in the infectious disease or other factors affecting the infectious disease, e.g., interventions employed.

Thus, not only is it important to continuously monitor the performance of the epidemiological computer model parameters within a given set of initializer ranges, but it is also important to verify that the initializer ranges themselves are accurate, i.e., the boundaries of the ranges are accurate. Inaccuracies in the boundaries of initializer ranges are referred to as a shift or drift of the assumptions and the corresponding initializer ranges, e.g., for hyperparameters of the epidemiological computer model, the inaccuracies are referred to as hyperparameter shifting or drift.

To combat this shift or drift, the illustrative embodiments provide automated computer tools to compare the current predictions generated by the epidemiological computer model 110 to one or more previous predictions generated by the same epidemiological computer model 110 to determine if there is a statistically significant deviation between the predictions. If there is a statistically significant deviation, it may mean that the assumptions under which the epidemiological computer model 110 was configured may no longer hold. Hence, a retraining of the epidemiological computer model 110 may be warranted.

In order to determine new initializer ranges, the illustrative embodiments may look to similar regions and identify the characteristics of the infectious disease spread, the population, and the interventions implemented in the various regions, such as through a clustering operation similar to that described above, or using the results of the previously performed clustering to identify similar regions, so as to identify the initializer ranges used for modeling these other similar regions. For the similar regions, a grid search operation may be performed on the boundaries of the initializer ranges for these similar regions to identify a best fit of parameter values from the grid search. That is, instances of the epidemiological computer model may be generated where each instance is configured with corresponding ones of the initializer ranges for the similar regions, and each instance may be executed on the data for the target region. The resulting predictions may then be compared to the ground truth (actual observed data for the target region) to determine the instance providing the best fit to the actual data. The initializer range settings for the best fit instance may then be used as the new set of initializer ranges for the epidemiological computer model.

Thus, not only does the continuous monitoring engine 150 provide improved automated computing tools for automatically maintaining the optimal model parameters for the epidemiological computer model, but also provides automated computing tools for automatically modifying the initializer ranges as assumptions shift or drift. It should be appreciated that it is assumed that such adjustment for shifting or drift may occur more often early in the modeling of the infectious disease, but should lessen over time since as more data is acquired, the inaccuracies of the early assumptions are compensated for and thus, additional shifting/drift will tend not to happen.

Figure 10:
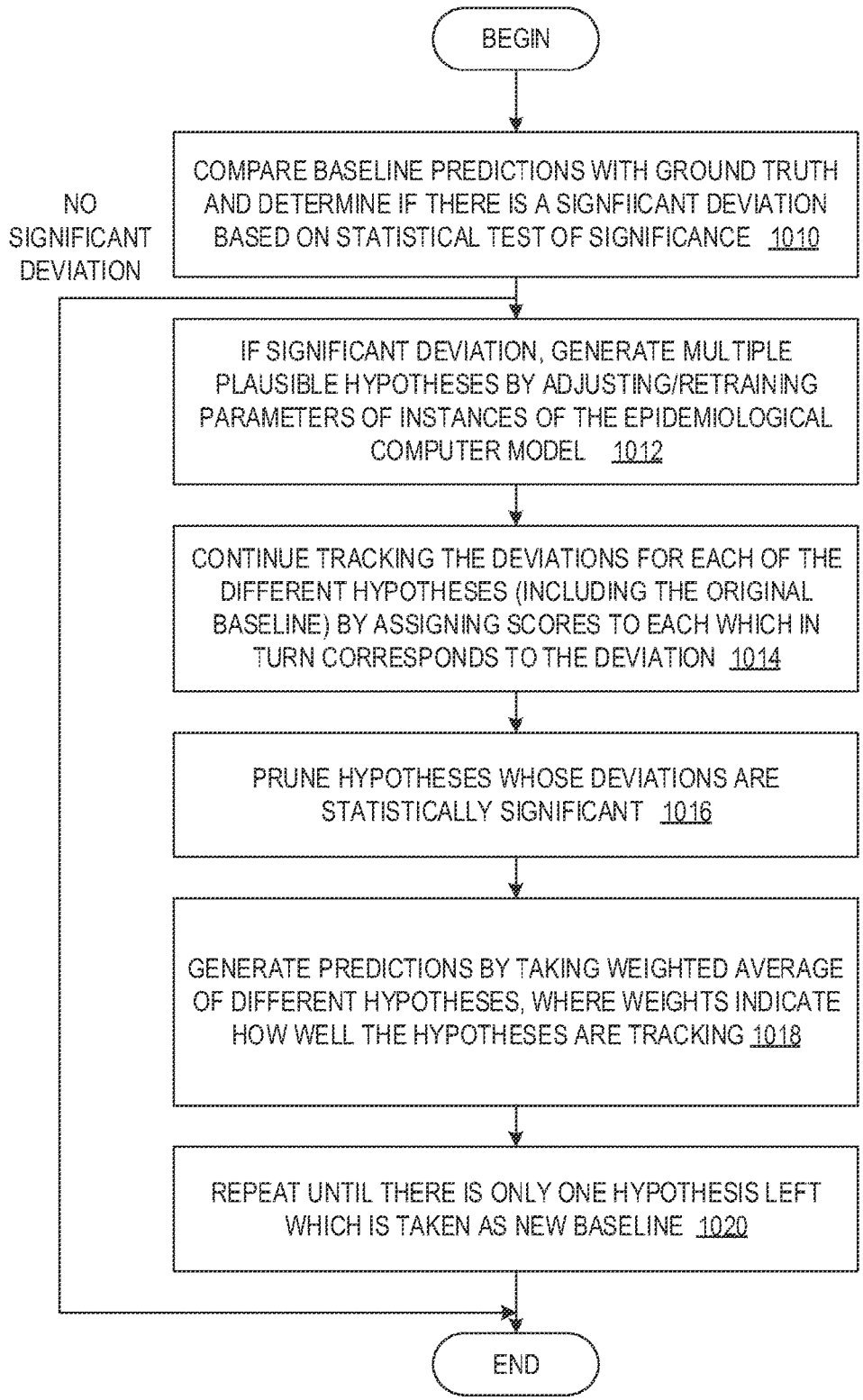
FIG. 10 is a flowchart outlining an example operation of a continuous monitoring engine with regard to continuous selection of optimal model parameter values within initializer ranges in accordance with one illustrative embodiment.

FIG. 10 is a flowchart outlining an example operation of a continuous monitoring engine with regard to continuous selection of optimal model parameter values within initializer ranges in accordance with one illustrative embodiment. The operation outlined in FIG. 10 may be performed by an improved computing tool of the continuous monitoring engine 150 in FIG. 1, for example, which operates to automatically, and continuously, monitor the performance of the epidemiological computer model as it generates predictions of infectious disease dynamics, e.g., numbers of incidents, cumulative numbers of incidents, numbers of fatalities, and the like. The operation automatically performs the monitoring operations and the automatic modification of model parameters based on results of this monitoring.

As shown in FIG. 10, the operation starts by comparing baseline (current) predictions with ground truth data to determine if there is a statistically significant deviation based on a statistical test of significance (step 1010). If there is not a significant deviation, the operation terminates and may be performed again at another trigger time, such as when the epidemiological computer model generates new predictions. Assuming that there is a significant deviation, multiple plausible different hypotheses are generated by generating instances of the epidemiological computer model with adjusted/retrained parameters configuring those instances and executing those instances on the data for the target (current) region (step 1012). What is meant by "plausible" is that the values of the parameters do not violate any predetermined rules indicating situations that are not realistic and which fall within the initializer ranges specified for the epidemiological computer model.

The instances of the epidemiological computer model, both the baseline and the other instances generated for the different hypotheses, are executed on the case report data for the target region to generate predictions which may be compared against a ground truth, i.e., the actual reported cases, such as incidents and fatalities, for a particular time point or time period, to generate deviations. These deviations may be scored such that the scores correspond to the amount of deviation, e.g., relatively higher deviations being given relatively higher scores (step 1014). Based on the scores associated with the instances, the hypotheses are pruned by discarding the instances of the epidemiological computer model that generate less accurate results, i.e., have greater deviations (step 1016). The remaining instances have their predictions combined through a weighted function, such as a weighted averaging, where the weights correspond to the historical accuracy of the instance's predictions (step 1018). Thus, if an instance has been maintained over multiple iterations, its weight will be greater than other instances. Moreover, if the instance has generated more accurate predictions, its weight will be greater than other instances as well. Instances having lower accurate predictions will have lower weights than other instances that are maintained but which generate more accurate predictions. This process may be repeated until only one hypothesis, and thus, corresponding instance of the epidemiological computer model, remains, which is then taken as the new baseline model generating new baseline predictions (step 1020). The operation then terminates. It should be appreciated that while the flowchart shows a termination, this process may be repeated periodically or continuously with the new baseline being selected and a new set of iterations performed with the new baseline.

The operation outlined in FIG. 10 provides an operation for continuously, and automatically, monitoring the performance of the epidemiological computer model and automatically adjusting the model parameters within the initializer ranges so as to maintain the accuracy of the model. In addition, as noted above, it is important to check the initializer ranges to ensure that the assumptions used to define these initializer ranges have not shifted or drifted such that they are no longer accurate.

Figure 11:
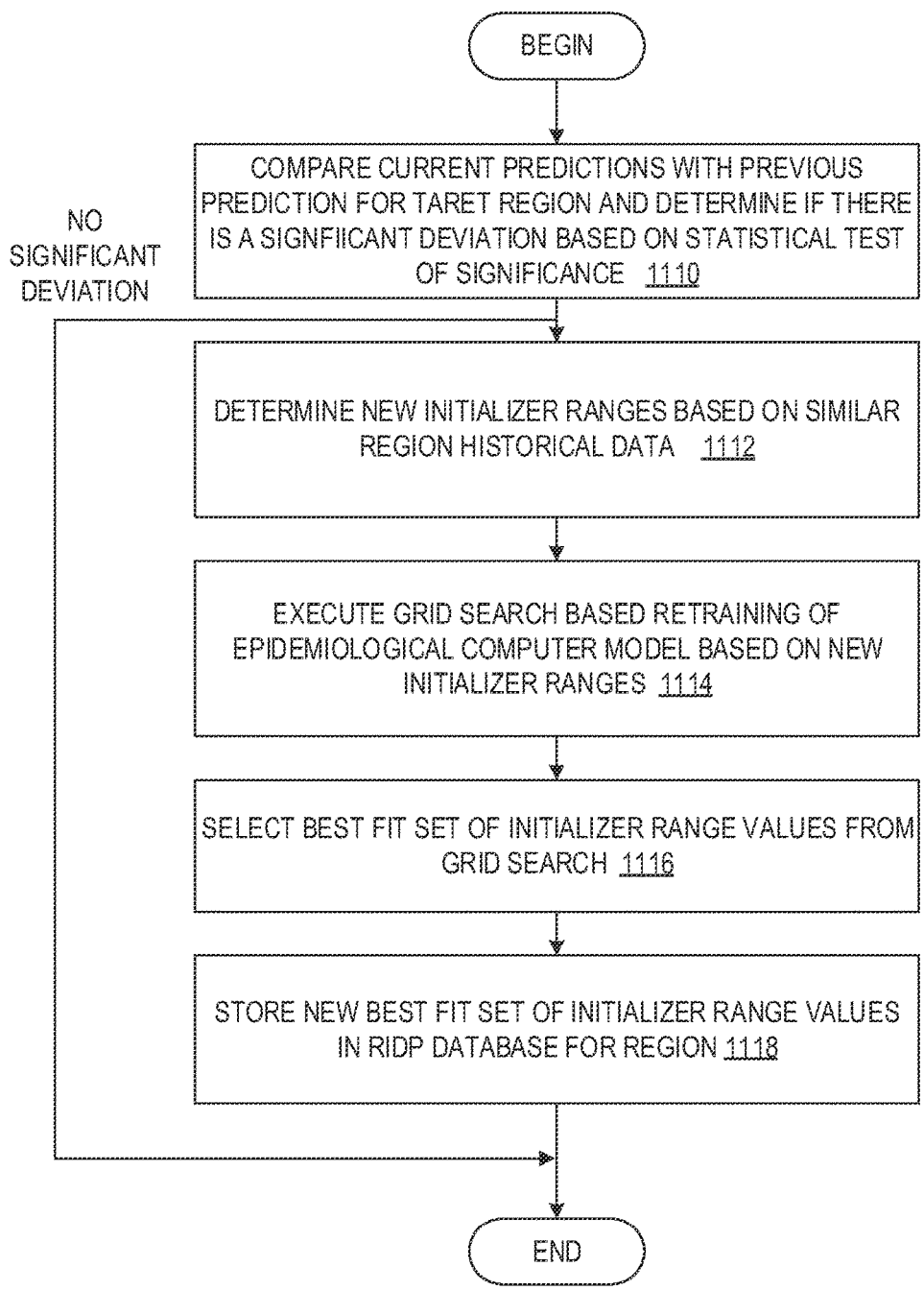
FIG. 11 is a flowchart outlining an example operation of a continuous monitoring engine with regard to detecting shifting of assumptions and corresponding hyperparameters and initializer ranges in accordance with one illustrative embodiment.

FIG. 11 is a flowchart outlining an example operation of a continuous monitoring engine with regard to detecting shifting of assumptions and corresponding hyperparameters and initializer ranges in accordance with one illustrative embodiment. The operation outlined in FIG. 11 may be performed by an improved computing tool of the continuous monitoring engine 150 in FIG. 1, for example, which operates to automatically, and continuously, monitor the performance of the epidemiological computer model as it generates predictions of infectious disease dynamics, e.g., numbers of incidents, cumulative numbers of incidents, numbers of fatalities, and the like. The operation automatically performs the monitoring operations and the automatic modification of initializer ranges based on results of this monitoring and detection that a potential shifting or drift of assumptions, and thus the corresponding initializer ranges, has occurred.

As shown in FIG. 11, the operation starts by comparing the current predictions of the epidemiological computer model with one or more previous predictions generated by the same instance of the epidemiological computer model for the target region (step 1110). This comparison determines if there is a statistically significant deviation based on a statistic test for significance. If there is no statistically significant deviation, the operation terminates. However, assuming that there is a statistically significant deviation, new initializer ranges are determined based on evaluating similar region historical data (step 1112). As noted above, this process may involve performing a clustering operation, or using a previously generated clustering of regions based on similar characteristics, to identify similar regions. Based on the similar regions identified, the corresponding initializer ranges associated with the epidemiological computer model instances used to model these other similar regions may be used as a basis for performing a grid search operation and retraining of instances of the epidemiological computer model for the target region (step 1114). That is, instances of the epidemiological computer model are generated with different sets of initializer ranges based on the grid search of initializer ranges for similar regions. The resulting instances are executed on data for the target region and predictions are generated which are compared to the ground truth. The comparison identifies which instances more accurately predict the actual data specified in the ground truth.

The best fit set of initializer range values are selected from the results of this grid search (step 1116). The best fit set of initializer range values are then stored in the RIDP database in association with the target region so that they may be used to configure instances of the epidemiological computer model used to predict infectious disease dynamics for the target region (step 1118). The operation then terminates. It should be appreciated that while the flowchart shows a termination, this process may be repeated periodically or continuously with each new prediction generated by the epidemiological computer model.

Distributed Data Processing System Environment

Figure 12:
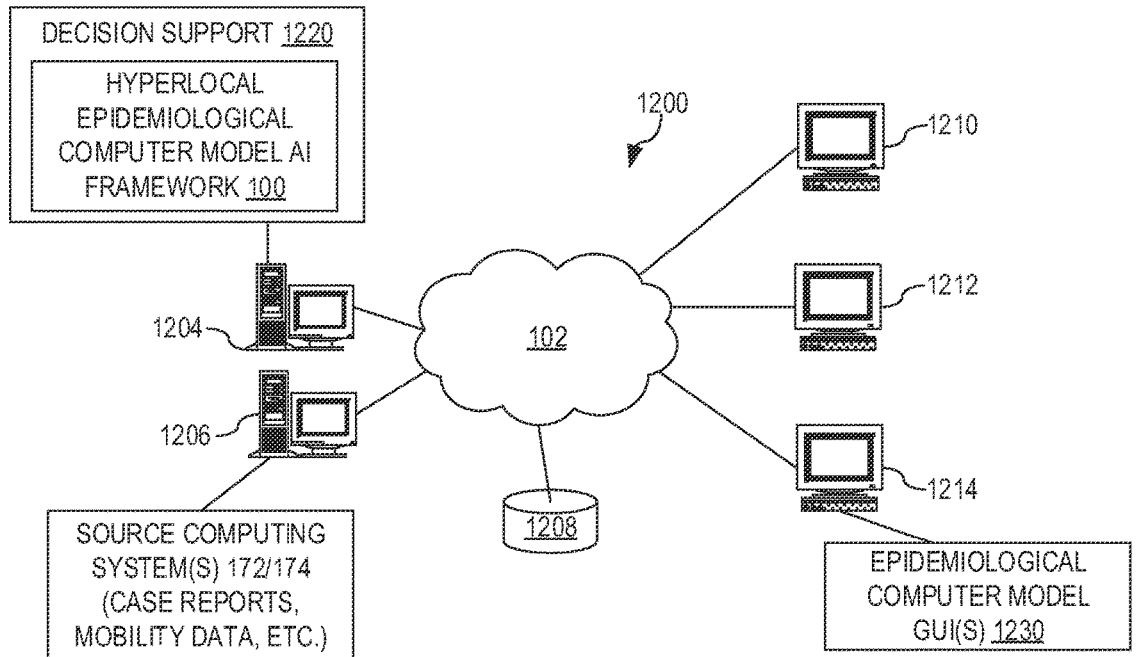
FIG. 12 is an example diagram of a distributed data processing system in which aspects of the illustrative embodiments may be implemented.
Figure 13:
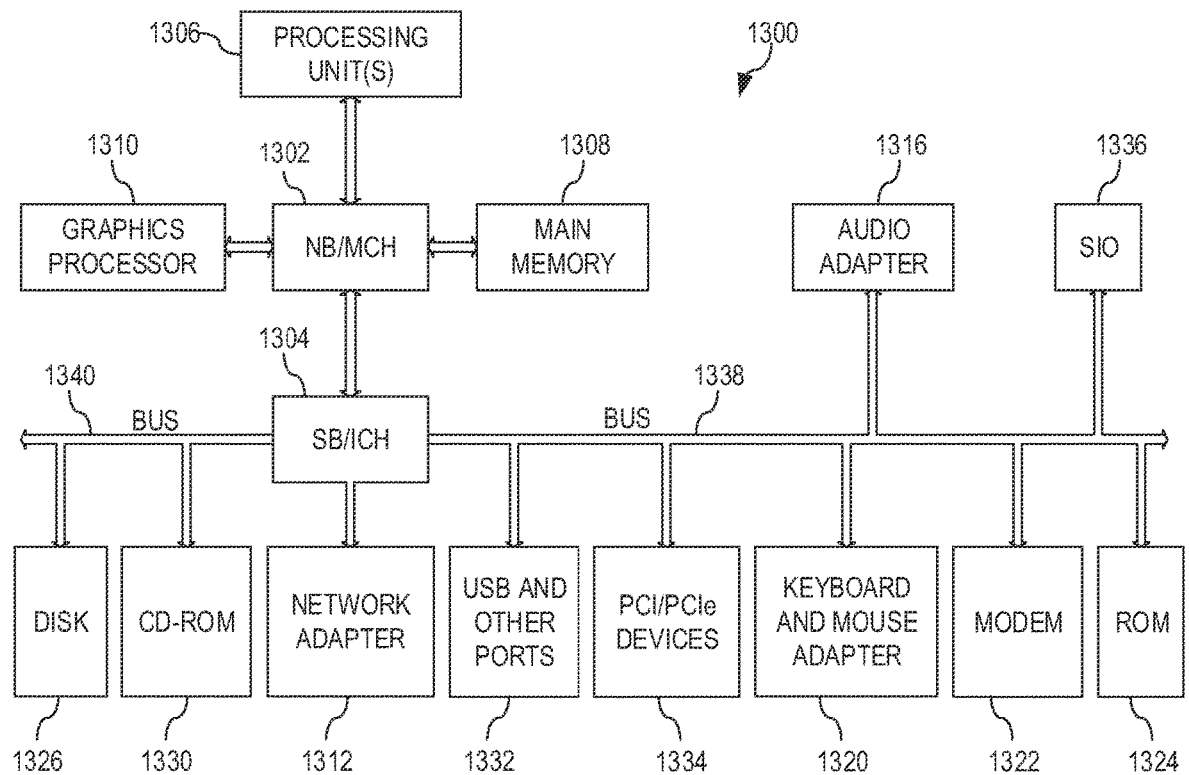
FIG. 13 is an example block diagram of a computing device in which aspects of the illustrative embodiments may be implemented.

From the above descriptions of the various mechanisms of various illustrative embodiments, it is apparent that the illustrative embodiments are directed to a specific improved computing tool that improves the way in which epidemiological computer models, employing artificial intelligence and machine learning, operate. Thus, the illustrative embodiments are specifically directed to computer technology and improving computer technology. In particular in accordance with one or more of the illustrative embodiments, computer specific mechanisms are provided for infectious disease modeling on a hyperlocal level, where these mechanisms are implemented in a distributed data processing system. FIGS. 12 and 13 are provided hereafter as example environments in which aspects of the illustrative embodiments may be implemented. It should be appreciated that FIGS. 12 and 13 are only examples and are not intended to assert or imply any limitation with regard to the environments in which aspects or embodiments of the present invention may be implemented. Many modifications to the depicted environments may be made without departing from the spirit and scope of the present invention.

FIG. 12 depicts a pictorial representation of an example distributed data processing system in which aspects of the illustrative embodiments may be implemented. Distributed data processing system 1200 may include a network of computers in which aspects of the illustrative embodiments may be implemented. The distributed data processing system 1200 contains at least one network 1202, which is the medium used to provide communication links between various devices and computers connected together within distributed data processing system 1200. The network 1202 may include connections, such as wire, wireless communication links, or fiber optic cables.

In the depicted example, server 1204 and server 1206 are connected to network 1202 along with storage unit 1208. In addition, clients 1210, 1212, and 1214 are also connected to network 1202. These clients 1210, 1212, and 1214 may be, for example, personal computers, network computers, or the like. In the depicted example, server 1204 provides data, such as boot files, operating system images, and applications to the clients 1210, 1212, and 1214. Clients 1210, 1212, and 1214 are clients to server 1204 in the depicted example. Distributed data processing system 1200 may include additional servers, clients, and other devices not shown.

In the depicted example, distributed data processing system 1200 is the Internet with network 1202 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 1200 may also be implemented to include a number of different types of networks, such as for example, an intranet, a local area network (LAN), a wide area network (WAN), or the like. As stated above, FIG. 12 is intended as an example, not as an architectural limitation for different embodiments of the present invention, and therefore, the particular elements shown in FIG. 12 should not be considered limiting with regard to the environments in which the illustrative embodiments of the present invention may be implemented.

As shown in FIG. 12, one or more of the computing devices, e.g., server 1204, may be specifically configured to implement a decision support artificial intelligence computing system 1220 having a hyperlocal epidemiological computer model artificial intelligence framework, such as framework 100 in FIG. 1, configured in accordance with one or more of the above-described illustrative embodiments. The framework 100 may operate based on data obtained from source computing systems, such as computing systems 172 and 174 in FIG. 1, and may interface with users via one or more epidemiological computer model graphical user interfaces 1230 generated and output on one or more of the client computing devices 1210-1214. The configuring of the computing device, or data processing system, may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 1204, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general-purpose computing device. Moreover, as described herein, the implementation of the mechanisms of the illustrative embodiments improves the functionality of the computing device and provides a useful and concrete result that facilitates hyperlocal modeling of infectious disease dynamics and provides improved computing tools for continuous and automatic modification of epidemiological computer models based on real-world observed data in order to maintain the accuracy of the epidemiological computer model and compensate for shifting of assumptions used to configure the epidemiological computer model. Furthermore, the illustrative embodiments provide mechanisms for leveraging similarities between hyperlocal regions to facilitate evaluating hypothetical scenarios regarding interventions or lifting of restrictions with regard to modeling the infectious disease using the epidemiological computer model, so as to provide accurate predictions facilitating better decision making by authorities.

It should also be appreciated that while FIG. 12 shows the framework 100 and decision support AI computing system 1220, and the source computing systems 172, 174, being associated with a single server computing device 1204, 1206, this is merely for illustration purposes. In actual implementation, these computing systems may each include a plurality of different computing devices and/or data processing systems that together implement the various components of the decision support artificial intelligence computing system 1220, the hyperlocal epidemiological computer model artificial intelligence framework 100, the source computing systems 172, 174, as well as other components needed to support the operations of these elements described above with regard to one or more of the illustrative embodiments.

As noted above, the mechanisms of the illustrative embodiments utilize specifically configured computing devices, or data processing systems, to perform the operations for implementing a hyperlocal epidemiological computer model artificial intelligence framework. These computing devices, or data processing systems, may comprise various hardware elements which are specifically configured, either through hardware configuration, software configuration, or a combination of hardware and software configuration, to implement one or more of the systems/subsystems described herein. FIG. 13 is a block diagram of just one example data processing system in which aspects of the illustrative embodiments may be implemented. Data processing system 1300 is an example of a computer, such as server 1204 in FIG. 12, in which computer usable code or instructions implementing the processes and aspects of the illustrative embodiments of the present invention may be located and/or executed so as to achieve the operation, output, and external effects of the illustrative embodiments as described herein.

In the depicted example, data processing system 1300 employs a hub architecture including north bridge and memory controller hub (NB/MCH) 1302 and south bridge and input/output (I/O) controller hub (SB/ICH) 1304. Processing unit 1306, main memory 1308, and graphics processor 1310 are connected to NB/MCH 1302. Graphics processor 1310 may be connected to NB/MCH 1302 through an accelerated graphics port (AGP).

In the depicted example, local area network (LAN) adapter 1312 connects to SB/ICH 1304. Audio adapter 1316, keyboard and mouse adapter 1320, modem 1322, read only memory (ROM) 1324, hard disk drive (HDD) 1326, CD-ROM drive 1330, universal serial bus (USB) ports and other communication ports 1332, and PCI/PCIe devices 1334 connect to SB/ICH 1304 through bus 1338 and bus 1340. PCI/PCIe devices may include, for example, Ethernet adapters, add-in cards, and PC cards for notebook computers. PCI uses a card bus controller, while PCIe does not. ROM 1324 may be, for example, a flash basic input/output system (BIOS).

HDD 1326 and CD-ROM drive 1330 connect to SB/ICH 1304 through bus 1340. HDD 1326 and CD-ROM drive 1330 may use, for example, an integrated drive electronics (IDE) or serial advanced technology attachment (SATA) interface. Super I/O (SIO) device 1336 may be connected to SB/ICH 1304.

An operating system runs on processing unit 1306. The operating system coordinates and provides control of various components within the data processing system 1300 in FIG. 13. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 1300.

As a server, data processing system 1300 may be, for example, an IBM eServer™ System P® computer system, Power™ processor-based computer system, or the like, running the Advanced Interactive Executive (AIX®) operating system or the LINUX® operating system. Data processing system 1300 may be a symmetric multiprocessor (SMP) system including a plurality of processors in processing unit 1306. Alternatively, a single processor system may be employed.

Instructions for the operating system, the object-oriented programming system, and applications or programs are located on storage devices, such as HDD 1326, and may be loaded into main memory 1308 for execution by processing unit 1306. The processes for illustrative embodiments of the present invention may be performed by processing unit 1306 using computer usable program code, which may be located in a memory such as, for example, main memory 1308, ROM 1324, or in one or more peripheral devices 1326 and 1330, for example.

A bus system, such as bus 1338 or bus 1340 as shown in FIG. 13, may be comprised of one or more buses. Of course, the bus system may be implemented using any type of communication fabric or architecture that provides for a transfer of data between different components or devices attached to the fabric or architecture. A communication unit, such as modem 1322 or network adapter 1312 of FIG. 13, may include one or more devices used to transmit and receive data. A memory may be, for example, main memory 1308, ROM 1324, or a cache such as found in NB/MCH 1302 in FIG. 13.

As mentioned above, in some illustrative embodiments the mechanisms of the illustrative embodiments may be implemented as application specific hardware, firmware, or the like, application software stored in a storage device, such as HDD 1326 and loaded into memory, such as main memory 1308, for executed by one or more hardware processors, such as processing unit 1306, or the like. As such, the computing device shown in FIG. 13 becomes specifically configured to implement the mechanisms of the illustrative embodiments and specifically configured to perform the operations and generate the outputs described herein with regard to the framework 100 and decision support artificial intelligence system 1220, for example.

Those of ordinary skill in the art will appreciate that the hardware in FIGS. 12 and 13 may vary depending on the implementation. Other internal hardware or peripheral devices, such as flash memory, equivalent non-volatile memory, or optical disk drives and the like, may be used in addition to or in place of the hardware depicted in FIGS. 12 and 13. Also, the processes of the illustrative embodiments may be applied to a multiprocessor data processing system, other than the SMP system mentioned previously, without departing from the spirit and scope of the present invention.

Moreover, the data processing system 1300 may take the form of any of a number of different data processing systems including client computing devices, server computing devices, a tablet computer, laptop computer, telephone or other communication device, a personal digital assistant (PDA), or the like. In some illustrative examples, data processing system 1300 may be a portable computing device that is configured with flash memory to provide non-volatile memory for storing operating system files and/or user-generated data, for example. Essentially, data processing system 1300 may be any known or later developed data processing system without architectural limitation.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method, in a data processing system comprising at least one processor and at least one memory coupled to the at least one processor and having instructions executed by the at least one processor to specifically configure the at least one processor to execute the method comprising:

executing, by a machine learning engine, a machine learning training of an infectious disease computer model on regional infectious disease and population (RIDP) database data for a set of predefined regions, to thereby train the infectious disease computer model to predict at least one characteristic of an infectious disease spread, wherein the RIDP database data comprising initializer ranges for hyperparameters of the infectious disease computer model and population data for the regions in the set of predefined regions, wherein the infectious disease computer model is a neural network computer model, and wherein the machine learning training comprises iteratively:
  processing, by the infectious disease computer model, input features from the RIDP database data based on a configuration of hyperparameters of the infectious disease computer model according to the initializer ranges, to generate a prediction of at least one characteristic of an infectious disease spread,
  comparing the predicted characteristic of the infectious disease spread to a ground truth for the characteristic of the infectious disease spread to determine an error, and
  modifying at least one operational parameter of the infectious disease computer model based on the error, wherein the processing, comparing, and modifying operations are repeated iteratively until the error is equal to or below a predetermined threshold error or a predetermined number of iterations have occurred;
receiving, via a user interface of the data processing system, a user definition of a hypothetical scenario for a target region, in the set of predefined regions, wherein the definition of the hypothetical scenario specifies one or more scenario features affecting the infectious disease spread amongst a population within the target region;
identifying one or more other predefined regions, in the set of predefined regions, having second region characteristics corresponding to first region characteristics of the target region at least by executing clustering computer logic on region characteristics of the set of predefined regions to generate a plurality of clusters of regions based on one or more distance valuation algorithms applied to the region characteristics, and identifying a cluster associated with the target region that comprises the one or more other predefined regions;
identifying one or more attributes of the one or more other predefined regions corresponding to the one or more scenario features based on learned changes in historical data corresponding to the one or more other predefined regions;
deriving at least one modified model parameter for the trained infectious disease computer model based on the identified one or more attributes that correspond to the one or more scenario features, wherein the at least one modified model parameter comprises at least one hyperparameter of the infectious disease computer model;
configuring an instance of the trained infectious disease computer model with the at least one modified model parameter;
executing the instance of the trained infectious disease computer model on case report data for the target region to generate at least one prediction for the infectious disease spread in the target region according to the hypothetical scenario; and
outputting the at least one prediction in a report output to a user computing device.

2. The method of claim 1, wherein the user definition is a natural language definition, and wherein processing the user definition comprises performing natural language processing on the natural language definition to extract natural language features of the natural language definition that are mapped to at least one of infectious disease characteristics or characteristics of interventions that affect infectious disease characteristics.

3. The method of claim 1, wherein the one or more attributes of the one or more other predefined regions comprise attributes corresponding to implementation or relaxing of interventions in corresponding predefined regions of the one or more other predefined regions.

4. The method of claim 1, wherein the one or more attributes of the one or more other predefined regions are levels of infectious disease characteristics corresponding to hypothetical levels of infectious disease state characteristics or transmission characteristics corresponding to the one or more scenario features.

5. The method of claim 1, wherein deriving at least one modified model parameter for the trained infectious disease computer model based on the identified one or more attributes comprises, for the one or more other predefined regions:
  generating a time ordered curve of case report data for the one or more other predefined regions;
  identifying one or more inflection points in the time ordered curve;
  correlating the one or more inflection points in the time ordered curve with one or more intervention entries specified in time stamped infectious disease intervention data for the one or more other predefined regions, the one or more intervention entries specifying interventions implemented by authorities to control spread of the infectious disease in the one or more other predefined regions; and
  identifying the at least one modified model parameter based on results of correlating the one or more inflection points with the one or more intervention entries.

6. The method of claim 5, wherein the at least one modified model parameter comprises at least one hyperparameter of the trained infectious disease computer model specifying at least one of a transmission rate of the infectious disease or a mobility of a population of the target region.

7. The method of claim 1, wherein the one or more scenario features are scenario features specifying a potential implementation or relaxing of an intervention to control spread of the infectious disease in the target region.

8. The method of claim 1, wherein the infectious disease computer model is a compartmental computer model comprising a plurality of compartments, each compartment corresponding to a state of the infectious disease and having a corresponding set of one or more differential equations modeling a portion of a population associated with the corresponding compartment, and wherein the compartmental computer model comprises one or more mobility isolation and countermeasure (MIC) compartments associated with corresponding other compartments of the compartmental computer model, and wherein the MIC compartments model an isolation of a portion of a population of a corresponding other compartment, based on mobility data for the population.

9. A computer program product comprising a computer readable storage medium having a computer readable program stored therein, wherein the computer readable program, when executed in a data processing system, causes the data processing system to:
  execute, by a machine learning engine, a machine learning training of an infectious disease computer model on regional infectious disease and population (RIDP) database data for a set of predefined regions, to thereby train the infectious disease computer model to predict at least one characteristic of an infectious disease spread, wherein the RIDP database data comprising initializer ranges for hyperparameters of the infectious disease computer model and population data for the regions in the set of predefined regions, wherein the infectious disease computer model is a neural network computer model, and wherein the machine learning training comprises iteratively:
processing, by the infectious disease computer model, input features from the RIDP database data based on a configuration of hyperparameters of the infectious disease computer model according to the initializer ranges, to generate a prediction of at least one characteristic of an infectious disease spread,
comparing the predicted characteristic of the infectious disease spread to a ground truth for the characteristic of the infectious disease spread to determine an error, and
modifying at least one operational parameter of the infectious disease computer model based on the error, wherein the processing, comparing, and modifying operations are repeated iteratively until the error is equal to or below a predetermined threshold error or a predetermined number of iterations have occurred;
receive, via a user interface of the data processing system, a user definition of a hypothetical scenario for a target region, in the set of predefined regions, wherein the definition of the hypothetical scenario specifies one or more scenario features affecting the infectious disease spread amongst a population within the target region;
identify one or more other predefined regions, in the set of predefined regions, having second region characteristics corresponding to first region characteristics of the target region at least by executing clustering computer logic on region characteristics of the set of predefined regions to generate a plurality of clusters of regions based on one or more distance valuation algorithms applied to the region characteristics, and identifying a cluster associated with the target region that comprises the one or more other predefined regions;
identify one or more attributes of the one or more other predefined regions corresponding to the one or more scenario features based on learned changes in historical data corresponding to the one or more other predefined regions;
derive at least one modified model parameter for the trained infectious disease computer model based on the identified one or more attributes that correspond to the one or more scenario features, wherein the at least one modified model parameter comprises at least one hyperparameter of the infectious disease computer model;
configure an instance of the trained infectious disease computer model with the at least one modified model parameter;
execute the instance of the trained infectious disease computer model on case report data for the target region to generate at least one prediction for the infectious disease spread in the target region according to the hypothetical scenario; and
output the at least one prediction in a report output to a user computing device.

10. The computer program product of claim 9, wherein the user definition is a natural language definition, and wherein processing the user definition comprises performing natural language processing on the natural language definition to extract natural language features of the natural language definition that are mapped to at least one of infectious disease characteristics or characteristics of interventions that affect infectious disease characteristics.

11. The computer program product of claim 9, wherein the one or more attributes of the one or more other predefined regions comprise attributes corresponding to implementation or relaxing of interventions in corresponding predefined regions of the one or more other predefined regions.

12. The computer program product of claim 9, wherein the one or more attributes of the one or more other predefined regions are levels of infectious disease characteristics corresponding to hypothetical levels of infectious disease state characteristics or transmission characteristics corresponding to the one or more scenario features.

13. The computer program product of claim 9, wherein deriving at least one modified model parameter for the trained infectious disease computer model based on the identified one or more attributes comprises, for the one or more other predefined regions:
generating a time ordered curve of case report data for the one or more other predefined regions;
identifying one or more inflection points in the time ordered curve;
correlating the one or more inflection points in the time ordered curve with one or more intervention entries specified in time stamped infectious disease intervention data for the one or more other predefined regions, the one or more intervention entries specifying interventions implemented by authorities to control spread of the infectious disease in the one or more other predefined regions; and
identifying the at least one modified model parameter based on results of correlating the one or more inflection points with the one or more intervention entries.

14. The computer program product of claim 13, wherein the at least one modified model parameter comprises at least one hyperparameter of the trained infectious disease computer model specifying at least one of a transmission rate of the infectious disease or a mobility of a population of the target region.

15. The computer program product of claim 9, wherein the one or more scenario features are scenario features specifying a potential implementation or relaxing of an intervention to control spread of the infectious disease in the target region.

16. A data processing system, comprising:
at least one processor; and
at least one memory coupled to the at least one processor, wherein the at least one memory comprises instructions which, when executed by the at least one processor, cause the at least one processor to:
execute, by a machine learning engine, a machine learning training of an infectious disease computer model on regional infectious disease and population (RIDP) database data for a set of predefined regions, to thereby train the infectious disease computer model to predict at least one characteristic of an infectious disease spread, wherein the RIDP database data comprising initializer ranges for hyperparameters of the infectious disease computer model and population data for the regions in the set of predefined regions, wherein the infectious disease computer model is a neural network computer model, and wherein the machine learning training comprises iteratively:
processing, by the infectious disease computer model, input features from the RIDP database data based on a configuration of hyperparameters of the infectious disease computer model according to the initializer ranges, to generate a prediction of at least one characteristic of an infectious disease spread, comparing the predicted characteristic of the infectious disease spread to a ground truth for the characteristic of the infectious disease spread to determine an error, and modifying at least one operational parameter of the infectious disease computer model based on the error, wherein the processing, comparing, and modifying operations are repeated iteratively until the error is equal to or below a predetermined threshold error or a predetermined number of iterations have occurred;

receive, via a user interface of the data processing system, a user definition of a hypothetical scenario for a target region, in the set of predefined regions, wherein the definition of the hypothetical scenario specifies one or more scenario features affecting the infectious disease spread amongst a population within the target region;

identify one or more other predefined regions, in the set of predefined regions, having second region characteristics corresponding to first region characteristics of the target region at least by executing clustering computer logic on region characteristics of the set of predefined regions to generate a plurality of clusters of regions based on one or more distance valuation algorithms applied to the region characteristics, and identifying a cluster associated with the target region that comprises the one or more other predefined regions;

identify one or more attributes of the one or more other predefined regions corresponding to the one or more scenario features based on learned changes in historical data corresponding to the one or more other predefined regions;

derive at least one modified model parameter for the trained infectious disease computer model based on the identified one or more attributes that correspond to the one or more scenario features, wherein the at least one modified model parameter comprises at least one hyperparameter of the infectious disease computer model;

configure an instance of the trained infectious disease computer model with the at least one modified model parameter;

execute the instance of the trained infectious disease computer model on case report data for the target region to generate at least one prediction for the infectious disease spread in the target region according to the hypothetical scenario; and output the at least one prediction in a report output to a user computing device.

17. The method of claim 1, wherein deriving at least one modified model parameter for the trained infectious disease computer model comprises:

executing a plurality of different instances of the trained infectious disease computer model on data for the target region, wherein each instance of the trained infectious disease computer model is configured with different modified model parameters corresponding to the one of the one or more other predefined regions; and selecting one of the plurality of different instances of the trained infectious disease computer model based on corresponding performance metrics for the different instances of the trained infectious disease computer model, wherein the at least one modified parameter comprises a parameter corresponding to the selected instance of the trained infectious disease computer model.

18. The method of claim 1, wherein the one or more scenario features affecting an infectious disease spread amongst a population within the target region comprises at least one of an intervention to be enacted on a population of the target region to affect the infectious disease spread, or a previously enacted intervention that is to be modified to a different level of enactment on the population of the target region, wherein the at least one prediction for an infectious disease spread in the target region according to the hypothetical scenario comprises a prediction of infectious disease spread due to enacting, or modifying the level of enactment, of the intervention on the population of the target region.

19. The method of claim 1, wherein receiving the user definition of the hypothetical scenario for the target region comprises:

receiving a user definition of a desired infectious disease spread result to be achieved;

performing a lookup operation, in a database of previous interventions, based on the desired infectious disease spread result to identify a previous intervention having an infectious disease spread result corresponding to the desired infectious disease spread result; and selecting the previous intervention as a scenario feature in the one or more scenario features.

20. The method of claim 19, wherein the lookup operation is performed only with regard to the target region and the one or more other predefined regions in the cluster associated with the target region.

* * * * *